(12) United States Patent
Nguyen et al.

(10) Patent No.: US 8,747,459 B2
(45) Date of Patent: Jun. 10, 2014

(54) SYSTEM AND METHOD FOR TRANSAPICAL DELIVERY OF AN ANNULUS ANCHORED SELF-EXPANDING VALVE

(75) Inventors: Than Nguyen, Fountain Valley, CA (US); Jacques Seguin, Windsor (GB); Stan Komatsu, Laguna Hills, CA (US); Hung Nguyen, Garden Grove, CA (US); Georg Boertlein, Meudon (FR)

(73) Assignee: Medtronic CoreValve LLC, Minneapolis, MN (US)

( * ) Notice: Subject to any disclaimer, the term of this patent is extended or adjusted under 35 U.S.C. 154(b) by 819 days.

(21) Appl. No.: 11/952,080

(22) Filed: Dec. 6, 2007

(65) Prior Publication Data

US 2008/0140189 A1    Jun. 12, 2008

Related U.S. Application Data

(60) Provisional application No. 60/868,891, filed on Dec. 6, 2006.

(51) Int. Cl.
   *A61F 2/24*    (2006.01)
(52) U.S. Cl.
   USPC ................ 623/2.11; 623/1.11; 623/1.12
(58) Field of Classification Search
   USPC ............... 623/2.11, 1.11, 1.12; 606/108, 194
   See application file for complete search history.

(56) References Cited

U.S. PATENT DOCUMENTS

| | | | |
|---|---|---|---|
| 3,657,744 A | 4/1972 | Ersek | |
| 3,671,979 A | 6/1972 | Moulopoulos | |
| 3,755,823 A | 9/1973 | Hancock | |
| 4,056,854 A | 11/1977 | Boretos et al. | |
| 4,222,126 A | 9/1980 | Boretos et al. | |
| 4,501,030 A | 2/1985 | Lane | |
| 4,574,803 A | 3/1986 | Storz | |
| 4,580,568 A | 4/1986 | Gianturco | |
| 4,592,340 A | 6/1986 | Boyles | |

(Continued)

FOREIGN PATENT DOCUMENTS

| CN | 2007-100074433 | 1/2007 |
|---|---|---|
| DE | 3640745 | 6/1987 |

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Melanie Tyson
*Assistant Examiner* — Todd J Scherbel

(57) ABSTRACT

A prosthetic valve assembly for use in replacing a deficient native valve comprises a replacement valve supported on an expandable prosthesis frame. The valve may be delivered transluminally or transmyocardially using a thorascopic or other limited access approach using a delivery catheter. Preferably, the initial partial expansion of the valve is performed against the native valve annulus to provide adequate anchoring and positioning of the valve as the remaining portions of the valve expand. The valve may be delivered using a retrograde or antegrade approach. When delivered using a retrograde approach, a delivery catheter with a pull-back sheath may be used, while antegrade delivery is preferably performed with a delivery catheter with a push-forward sheath that releases the proximal end of the valve first.

14 Claims, 53 Drawing Sheets

(56) References Cited

U.S. PATENT DOCUMENTS

| | | | |
|---|---|---|---|
| 4,612,011 A | 9/1986 | Kautzky | |
| 4,662,885 A | 5/1987 | DiPisa, Jr. | |
| 4,681,908 A | 7/1987 | Broderick et al. | |
| 4,710,192 A | 12/1987 | Liotta et al. | |
| 4,787,899 A | 11/1988 | Lazarus | |
| 4,787,901 A | 11/1988 | Baykut | |
| 4,796,629 A | 1/1989 | Grayzel | |
| 4,819,751 A | 4/1989 | Shimada et al. | |
| 4,834,755 A | 5/1989 | Silvestrini et al. | |
| 4,872,874 A | 10/1989 | Taheri | |
| 4,878,495 A | 11/1989 | Grayzel | |
| 4,878,906 A | 11/1989 | Lindemann et al. | |
| 4,883,458 A | 11/1989 | Shiber | |
| 4,909,252 A | 3/1990 | Goldberger | |
| 4,917,102 A | 4/1990 | Miller et al. | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,078,720 A * | 1/1992 | Burton et al. | 606/108 |
| 5,201,757 A * | 4/1993 | Heyn et al. | 606/198 |
| 5,272,909 A | 12/1993 | Nguyen et al. | |
| 5,295,958 A | 3/1994 | Shturman | |
| 5,327,774 A | 7/1994 | Nguyen et al. | |
| 5,332,402 A | 7/1994 | Teitelbaum et al. | |
| 5,350,398 A | 9/1994 | Pavcnik et al. | |
| 5,370,685 A | 12/1994 | Stevens | |
| 5,397,351 A | 3/1995 | Pavcnik et al. | |
| 5,411,552 A | 5/1995 | Andersen et al. | |
| 5,415,633 A | 5/1995 | Lazarus et al. | |
| 5,421,826 A | 6/1995 | Crocker et al. | |
| 5,431,676 A | 7/1995 | Dubrul et al. | |
| 5,443,446 A | 8/1995 | Shturman | |
| 5,449,384 A | 9/1995 | Johnson | |
| 5,489,294 A | 2/1996 | McVenes et al. | |
| 5,496,346 A | 3/1996 | Horzewski et al. | |
| 5,500,014 A | 3/1996 | Quijano et al. | |
| 5,507,767 A | 4/1996 | Maeda et al. | |
| 5,545,209 A | 8/1996 | Roberts et al. | |
| 5,545,211 A | 8/1996 | An et al. | |
| 5,545,214 A | 8/1996 | Stevens | |
| 5,554,185 A | 9/1996 | Block et al. | |
| 5,571,135 A * | 11/1996 | Fraser et al. | 623/1.12 |
| 5,575,818 A | 11/1996 | Pinchuk | |
| 5,580,922 A | 12/1996 | Park et al. | |
| 5,591,195 A | 1/1997 | Taheri et al. | |
| 5,609,626 A | 3/1997 | Quijano et al. | |
| 5,645,559 A | 7/1997 | Hachtman et al. | |
| 5,665,115 A | 9/1997 | Cragg | |
| 5,667,523 A | 9/1997 | Bynon et al. | |
| 5,674,277 A | 10/1997 | Freitag | |
| 5,702,368 A | 12/1997 | Stevens et al. | |
| 5,713,953 A | 2/1998 | Vallana et al. | |
| 5,716,417 A | 2/1998 | Girard et al. | |
| 5,746,709 A | 5/1998 | Rom et al. | |
| 5,749,890 A | 5/1998 | Shaknovich | |
| 5,766,151 A | 6/1998 | Valley et al. | |
| 5,782,809 A | 7/1998 | Umeno et al. | |
| 5,800,456 A | 9/1998 | Maeda et al. | |
| 5,800,508 A | 9/1998 | Goicoechea et al. | |
| 5,824,041 A | 10/1998 | Lenker | |
| 5,824,043 A | 10/1998 | Cottone, Jr. | |
| 5,824,053 A | 10/1998 | Khosravi et al. | |
| 5,824,056 A | 10/1998 | Rosenberg | |
| 5,824,061 A | 10/1998 | Quijano et al. | |
| 5,824,064 A | 10/1998 | Taheri | |
| 5,843,158 A | 12/1998 | Lenker et al. | |
| 5,851,232 A | 12/1998 | Lois | |
| 5,855,597 A | 1/1999 | Jayaraman | |
| 5,855,601 A | 1/1999 | Bessler et al. | |
| 5,861,028 A | 1/1999 | Angell | |
| 5,876,448 A | 3/1999 | Thompson et al. | |
| 5,888,201 A | 3/1999 | Stinson et al. | |
| 5,906,619 A | 5/1999 | Olson et al. | |
| 5,913,842 A | 6/1999 | Boyd et al. | |
| 5,925,063 A | 7/1999 | Khosravi | |
| 5,944,738 A | 8/1999 | Amplatz et al. | |
| 5,957,949 A | 9/1999 | Leonhardt et al. | |
| 5,968,068 A | 10/1999 | Dehdashtian et al. | |
| 5,980,533 A * | 11/1999 | Holman | 623/1.11 |
| 5,984,957 A | 11/1999 | Laptewicz, Jr. et al. | |
| 5,989,280 A * | 11/1999 | Euteneuer et al. | 623/1.1 |
| 5,997,573 A | 12/1999 | Quijano et al. | |
| 6,027,510 A | 2/2000 | Alt | |
| 6,027,525 A | 2/2000 | Suh et al. | |
| 6,029,671 A | 2/2000 | Stevens et al. | |
| 6,042,589 A | 3/2000 | Marianne | |
| 6,042,598 A | 3/2000 | Tsugita et al. | |
| 6,042,607 A | 3/2000 | Williamson, IV | |
| 6,051,014 A | 4/2000 | Jang | |
| 6,059,809 A | 5/2000 | Amor et al. | |
| 6,077,297 A * | 6/2000 | Robinson et al. | 623/1.11 |
| 6,110,201 A | 8/2000 | Quijano et al. | |
| 6,146,366 A | 11/2000 | Schachar | |
| 6,159,239 A | 12/2000 | Greenhalgh | |
| 6,162,208 A | 12/2000 | Hipps | |
| 6,162,245 A | 12/2000 | Jayaraman | |
| 6,171,335 B1 | 1/2001 | Wheatley et al. | |
| 6,190,406 B1 | 2/2001 | Duerig et al. | |
| 6,200,336 B1 | 3/2001 | Pavcnik et al. | |
| 6,203,550 B1 | 3/2001 | Olson | |
| 6,210,408 B1 | 4/2001 | Chandrasekaran et al. | |
| 6,218,662 B1 | 4/2001 | Tchakarov et al. | |
| 6,221,006 B1 | 4/2001 | Dubrul et al. | |
| 6,221,091 B1 | 4/2001 | Khosravi | |
| 6,241,757 B1 | 6/2001 | An et al. | |
| 6,245,102 B1 | 6/2001 | Jayaraman | |
| 6,248,116 B1 | 6/2001 | Chevilon | |
| 6,258,114 B1 | 7/2001 | Konya et al. | |
| 6,258,115 B1 | 7/2001 | Dubrul | |
| 6,258,120 B1 | 7/2001 | McKenzie et al. | |
| 6,277,555 B1 | 8/2001 | Duran et al. | |
| 6,299,637 B1 | 10/2001 | Shaolian et al. | |
| 6,302,906 B1 | 10/2001 | Goicoechea et al. | |
| 6,309,382 B1 | 10/2001 | Garrison et al. | |
| 6,309,417 B1 | 10/2001 | Spence et al. | |
| 6,338,735 B1 | 1/2002 | Stevens | |
| 6,348,063 B1 | 2/2002 | Yassour et al. | |
| 6,350,277 B1 | 2/2002 | Kocur | |
| 6,350,278 B1 * | 2/2002 | Lenker et al. | 623/1.12 |
| 6,352,708 B1 | 3/2002 | Duran et al. | |
| 6,371,970 B1 | 4/2002 | Khosravi et al. | |
| 6,371,983 B1 | 4/2002 | Lane | |
| 6,379,383 B1 | 4/2002 | Palmaz et al. | |
| 6,380,457 B1 | 4/2002 | Yurek et al. | |
| 6,398,807 B1 | 6/2002 | Chouinard et al. | |
| 6,409,750 B1 | 6/2002 | Hyodoh et al. | |
| 6,425,916 B1 | 7/2002 | Garrison et al. | |
| 6,440,164 B1 | 8/2002 | DiMatteo et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,468,303 B1 | 10/2002 | Amplatz et al. | |
| 6,475,239 B1 | 11/2002 | Campbell et al. | |
| 6,482,228 B1 | 11/2002 | Norred | |
| 6,488,704 B1 | 12/2002 | Connelly et al. | |
| 6,494,909 B2 | 12/2002 | Greenhalgh | |
| 6,503,272 B2 | 1/2003 | Duerig et al. | |
| 6,508,833 B2 | 1/2003 | Pavcnik et al. | |
| 6,527,800 B1 | 3/2003 | McGuckin, Jr. et al. | |
| 6,530,949 B2 | 3/2003 | Konya et al. | |
| 6,530,952 B2 | 3/2003 | Vesely | |
| 6,562,031 B2 | 5/2003 | Chandrasekaran et al. | |
| 6,562,058 B2 | 5/2003 | Seguin et al. | |
| 6,569,196 B1 | 5/2003 | Vesely | |
| 6,585,758 B1 | 7/2003 | Chouinard et al. | |
| 6,592,546 B1 | 7/2003 | Barbut et al. | |
| 6,605,112 B1 | 8/2003 | Moll et al. | |
| 6,613,077 B2 | 9/2003 | Gilligan et al. | |
| 6,622,604 B1 | 9/2003 | Chouinard et al. | |
| 6,635,068 B1 | 10/2003 | Dubrul et al. | |
| 6,645,240 B2 * | 11/2003 | Yee | 623/1.11 |

(56) References Cited

U.S. PATENT DOCUMENTS

| | | |
|---|---|---|
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,841 B2 | 5/2004 | Musbach et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,235,095 B2 * | 6/2007 | Haverkost et al. .......... 623/1.12 |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,331,985 B2 * | 2/2008 | Thompson et al. .......... 623/1.11 |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Schreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,682,390 B2 | 3/2010 | Seguin |
| 7,766,953 B2 * | 8/2010 | Purdy et al. .................. 623/1.12 |
| 7,780,726 B2 | 8/2010 | Seguin |
| 7,887,573 B2 * | 2/2011 | Haverkost et al. .......... 623/1.11 |
| 2001/0001314 A1 | 5/2001 | Davison et al. |
| 2001/0002445 A1 | 5/2001 | Vesely |
| 2001/0004699 A1 | 6/2001 | Gittings et al. |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |

(56) References Cited

U.S. PATENT DOCUMENTS

| | | |
|---|---|---|
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093075 A1 | 5/2004 | Kuehne |
| 2004/0097788 A1 | 5/2004 | Mourlas et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1* | 10/2004 | Seguin et al. ................ 623/2.11 |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0074484 A1 | 4/2006 | Huber |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoeffer et al. |
| 2006/0212111 A1 | 9/2006 | Case et al. |
| 2006/0247570 A1 | 11/2006 | Pokorney |
| 2006/0247763 A1 | 11/2006 | Slater |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0038295 A1 | 2/2007 | Case et al. |
| 2007/0043381 A1* | 2/2007 | Furst et al. ................ 606/108 |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0112422 A1 | 5/2007 | Dehdashtian |
| 2007/0162102 A1 | 7/2007 | Ryan et al. |

(56) References Cited

U.S. PATENT DOCUMENTS

| | | |
|---|---|---|
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0161910 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0164006 A1 | 6/2009 | Seguin et al. |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0004740 A1 | 1/2010 | Seguin et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0069852 A1 | 3/2010 | Kelley |
| 2010/0094411 A1 | 4/2010 | Tuval et al. |
| 2010/0100167 A1* | 4/2010 | Bortlein et al. ............... 623/1.11 |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0161045 A1 | 6/2010 | Righini |
| 2010/0234940 A1 | 9/2010 | Dolan |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 10 074 | 10/2001 |
| DE | 100 49 812 | 4/2002 |
| DE | 100 49 813 | 4/2002 |
| DE | 100 49 815 | 4/2002 |
| EP | 1057460 A1 | 6/2000 |
| EP | 1255510 | 11/2002 |
| EP | 1469797 | 11/2005 |
| FR | 2778217 | 12/1999 |
| FR | 2815844 | 5/2000 |
| GB | 2056023 | 3/1981 |
| GB | 2433700 | 12/2007 |
| JP | 2010-504142 | 2/2010 |
| SU | 1271508 | 11/1986 |
| WO | 95/29640 | 11/1995 |
| WO | WO9963909 | 12/1999 |
| WO | 00/44313 | 8/2000 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 2004/019825 | 3/2004 |
| WO | 2004/089250 | 10/2004 |
| WO | 2005/004753 | 1/2005 |
| WO | 2005/046528 | 5/2005 |
| WO | 2006/026371 | 3/2006 |
| WO | 2008/047354 | 4/2008 |
| WO | 2008/138584 | 11/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |

(56) References Cited

FOREIGN PATENT DOCUMENTS

| WO | 2009/111241 | 9/2009 |
|---|---|---|
| WO | 2009/140545 | 11/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Stassano et al., "Mid-term results of the valve-on-valve technique for bioprosthetic failure," Eur. J. Cardiothorac. Surg. 2000; 18:453-457.
Pavcnik et al., "Aortic and venous valve for percutaneous insertion," Min. Invas. Ther. & Allied Techol. 2000, vol. 9, pp. 287-292.
English translation of Japanese Office Action for JP 2009-540482, Sep. 18, 2012, 4 pages.

* cited by examiner

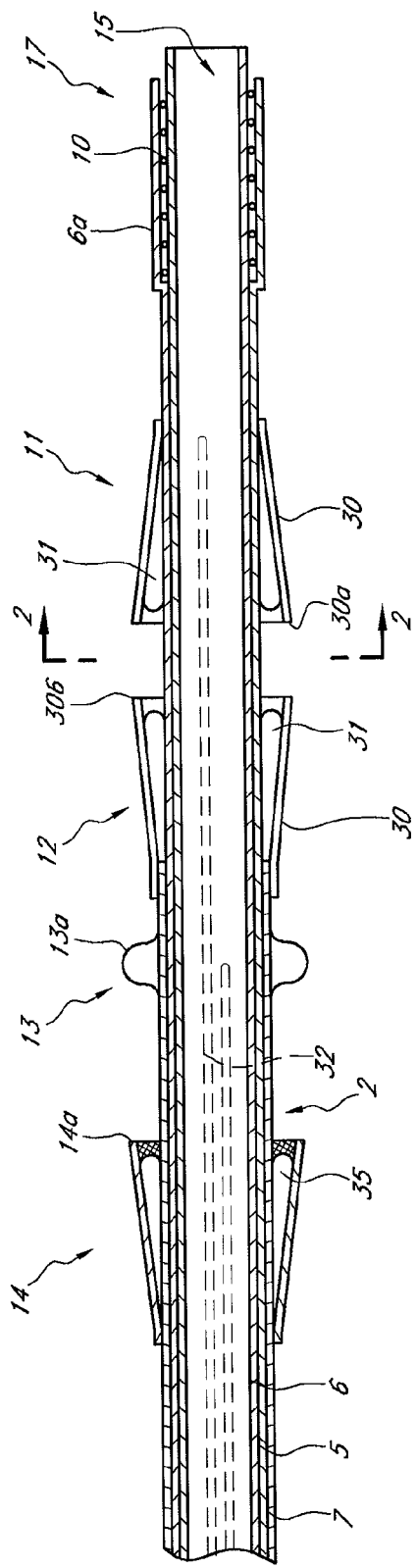
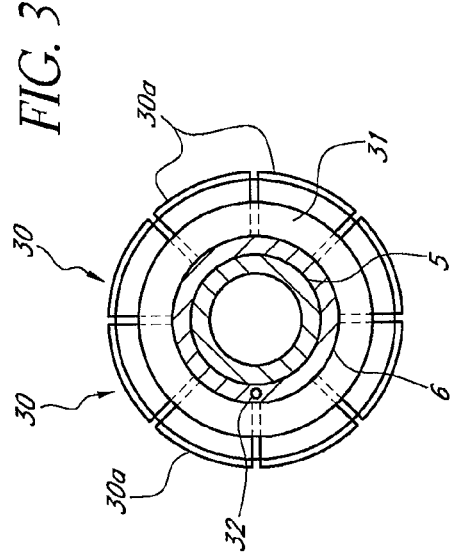
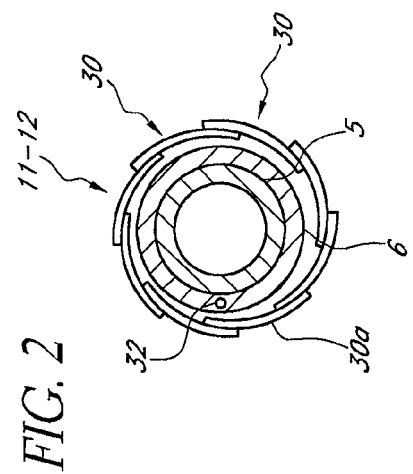
FIG. 1
FIG. 3
FIG. 2

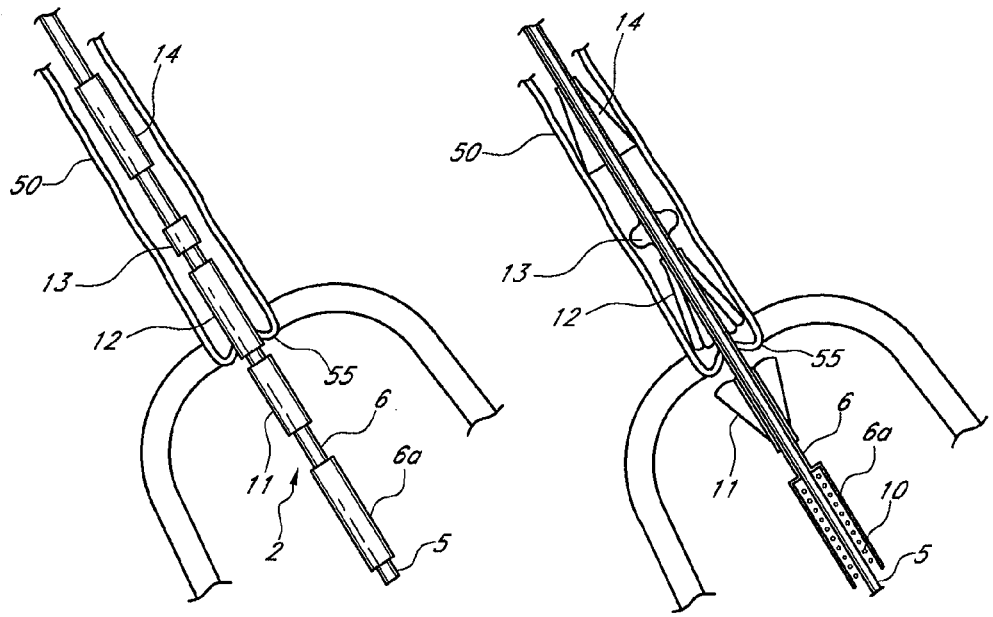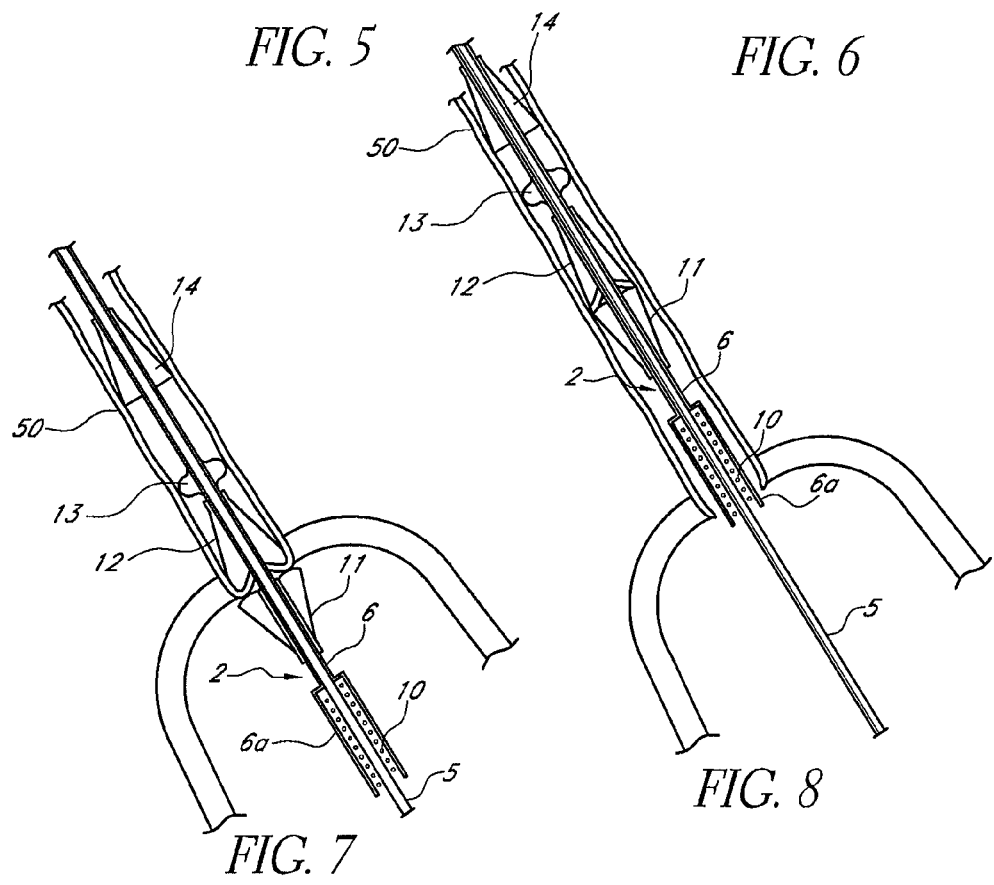
FIG. 5  FIG. 6  FIG. 7  FIG. 8

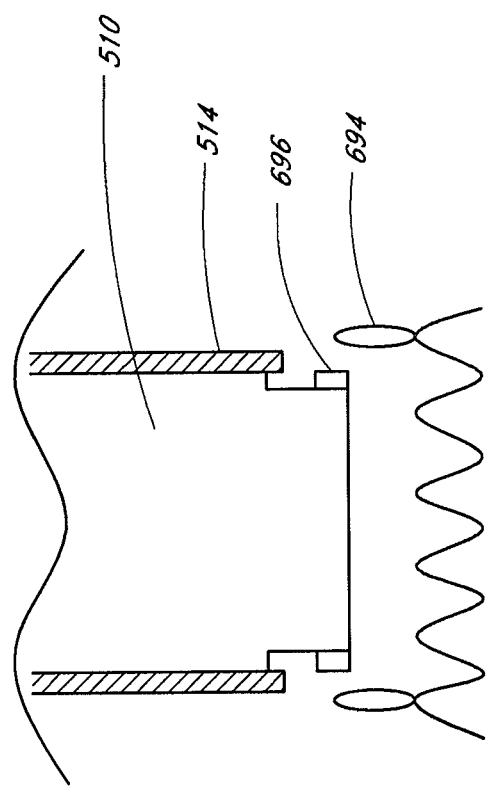

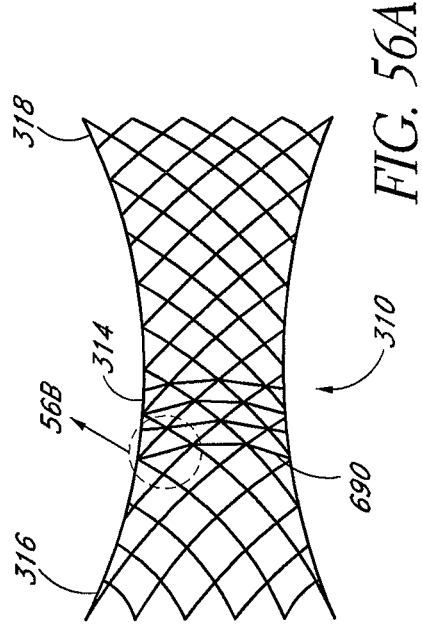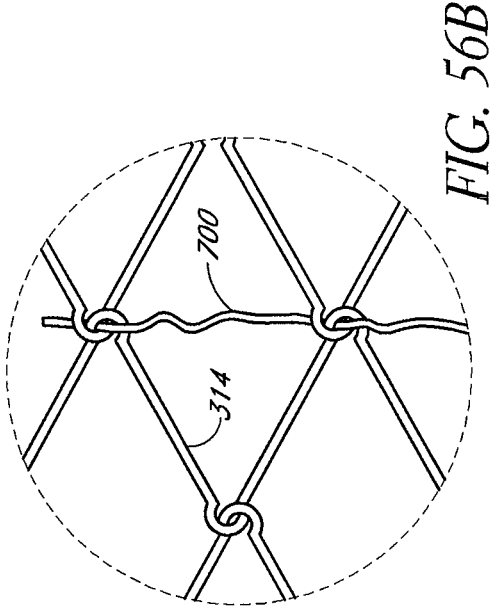
FIG. 56A
FIG. 56B

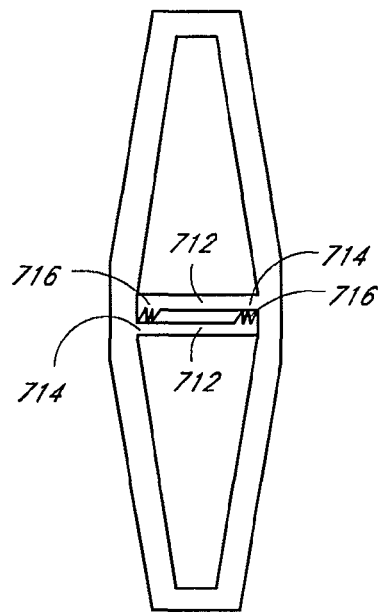
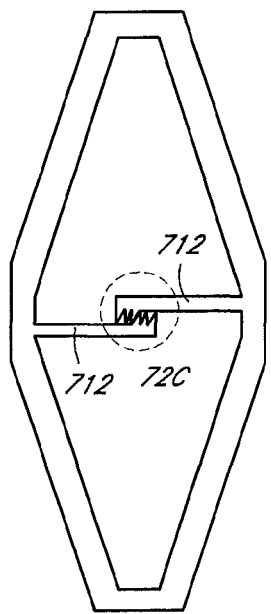
FIG. 73A            FIG. 73B
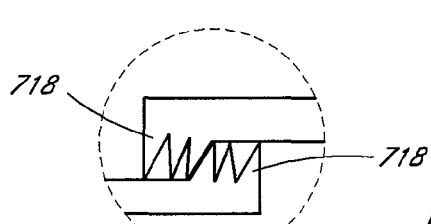
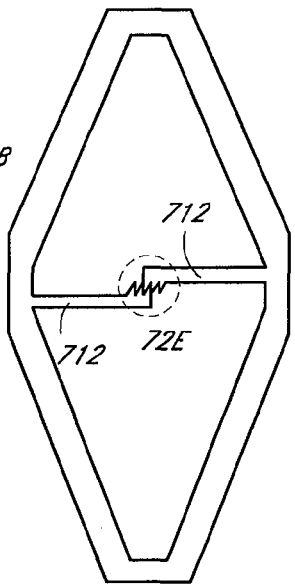
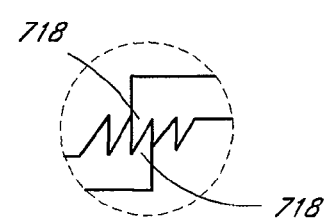
FIG. 73C
FIG. 73E
FIG. 73D

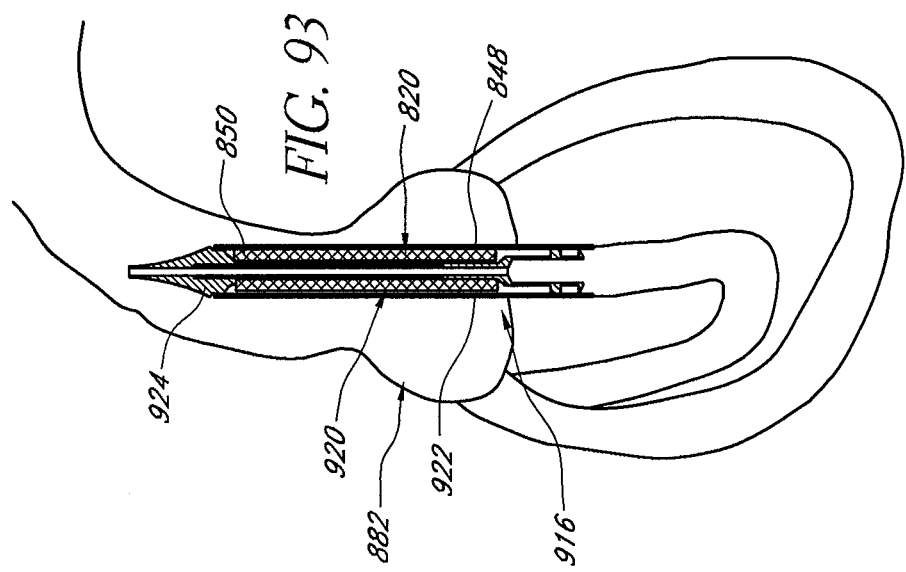
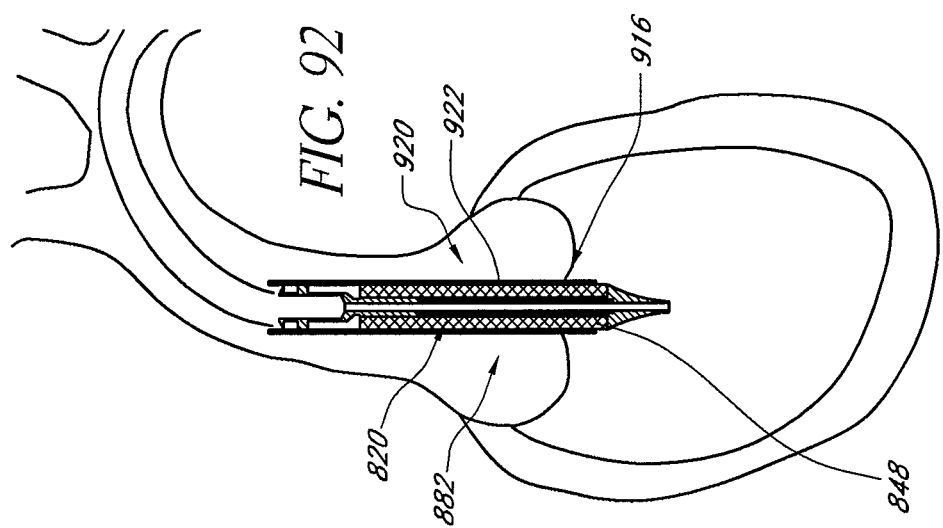

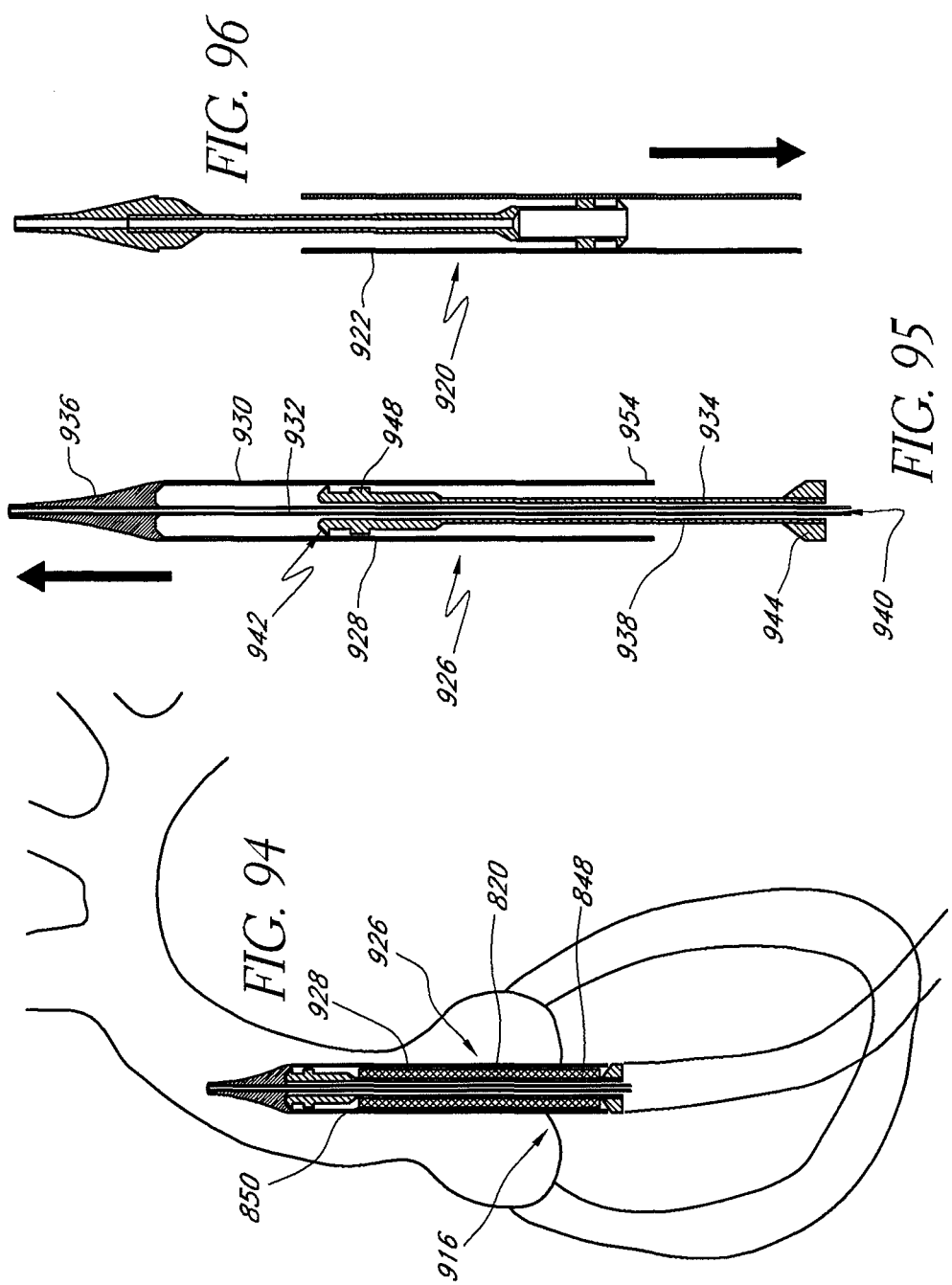

SYSTEM AND METHOD FOR TRANSAPICAL DELIVERY OF AN ANNULUS ANCHORED SELF-EXPANDING VALVE

The present application claims priority under 35 U.S.C. §119(e) to U.S. Provisional Application No. 60/868,891, filed on Dec. 6, 2006, and hereby incorporated by reference in its entirety.

FIELD OF THE INVENTION

The present invention relates to a prosthetic cardiac valve and related deployment system that can be delivered percutaneously through the vasculature, and a method for delivering same.

BACKGROUND OF THE INVENTION

Currently, the replacement of a deficient cardiac valve is often performed by opening the thorax, placing the patient under extracorporeal circulation or peripheral aorto-venous heart assistance, temporarily stopping the heart, surgically opening the heart, excising the deficient valve, and then implanting a prosthetic valve in its place. U.S. Pat. No. 4,106,129 to Carpentier describes a bioprosthetic heart valve with compliant orifice ring for surgical implantation. This procedure generally requires prolonged patient hospitalization, as well as extensive and often painful recovery. It also presents advanced complexities and significant costs.

To address the risks associated with open heart implantation, devices and methods for replacing a cardiac valve by a less invasive means have been contemplated. For example, French Patent Application No. 99 14462 illustrates a technique and a device for the ablation of a deficient heart valve by percutaneous route, with a peripheral valvular approach. International Application (PCT) Nos. WO 93/01768 and WO 97/28807, as well as U.S. Pat. No. 5,814,097 to Sterman et al., U.S. Pat. No. 5,370,685 to Stevens, and U.S. Pat. No. 5,545,214 to Stevens illustrate techniques that are not very invasive as well as instruments for implementation of these techniques.

U.S. Pat. No. 3,671,979 to Moulopoulos and U.S. Pat. No. 4,056,854 to Boretos describe a catheter-mounted artificial heart valve for implantation in close proximity to a defective heart valve. Both of these prostheses are temporary in nature and require continued connection to the catheter for subsequent repositioning or removal of the valve prosthesis, or for subsequent valve activation.

With regard to the positioning of a replacement heart valve, attaching this valve on a support with a structure in the form of a wire or network of wires, currently called a stent, has been proposed. This stent support can be contracted radially in such a way that it can be introduced into the body of the patient percutaneously by means of a catheter, and it can be deployed so as to be radially expanded once it is positioned at the desired target site. U.S. Pat. No. 3,657,744 to Ersek discloses a cylindrical, stent-supported, tri-leaflet, tissue, heart valve that can be delivered through a portion of the vasculature using an elongate tool. The stent is mounted onto the expansion tool prior to delivery to the target location where the stent and valve are expanded into place. More recently, U.S. Pat. No. 5,411,552 to Andersen also illustrates a technique of this type. In the Andersen patent, a stent-supported tissue valve is deliverable percutaneously to the native heart valve site for deployment using a balloon or other expanding device. Efforts have been made to develop a stent-supported valve that is self-expandable, using memory materials such as Nitinol.

The stent-supported systems designed for the positioning of a heart valve introduce uncertainties of varying degree with regard to minimizing migration from the target valve site. A cardiac valve that is not adequately anchored in place to resist the forces of the constantly changing vessel wall diameter, and turbulent blood flow therethrough, may dislodge itself, or otherwise become ineffective. In particular, the known stents do not appear to be suited to sites in which the cardiac wall widens on either proximally and/or distally of the valve annulus situs. Furthermore, the native cardiac ring remaining after ablation of the native valve can hinder the positioning of these stents. These known systems also in certain cases create problems related to the sealing quality of the replacement valve. In effect, the existing cardiac ring can have a surface that is to varying degrees irregular and calcified, which not only lessens the quality of the support of the stent against this ring but also acts as the source of leaks between the valve and this ring. Also, these systems can no longer be moved at all after deployment of the support, even if their position is not optimal. Furthermore, inflating a balloon on a stented valve as described by Andersen may traumatize the valve, especially if the valve is made from a fragile material as a living or former living tissue.

Also, the existing techniques are however considered not completely satisfactory and capable of being improved. In particular, some of these techniques have the problem of involving in any case putting the patient under extracorporeal circulation or peripheral aorto-venous heart assistance and temporary stopping of the heart; they are difficult to put into practice; they do not allow precise control of the diameter according to which the natural valve is cut, in view of the later calibration of the prosthetic valve; they lead to risks of diffusion of natural valve fragments, often calcified, into the organism, which can lead to an embolism, as well as to risks of perforation of the aortic or cardiac wall; they moreover induce risks of acute reflux of blood during ablation of the natural valve and risk of obstruction of blood flow during implantation of the device with a balloon expandable stent for example.

SUMMARY OF THE INVENTION

One object of the invention is a prosthetic valve assembly for use in replacing a deficient native valve comprises a replacement valve supported on an expandable prosthesis frame. The valve may be delivered transluminally or transmyocardially using a thoracscopic or other limited access approach using a delivery catheter. Preferably, the initial partial expansion of the valve is performed against the native valve annulus to provide adequate anchoring and positioning of the valve as the remaining portions of the valve expand. The valve may be delivered using a retrograde or antegrade approach. When delivered using a retrograde approach, a delivery catheter with a pull-back sheath may be used, while antegrade delivery is preferably performed with a delivery catheter with a push-forward sheath that releases the proximal end of the valve first.

In another embodiment, a method for delivering a self-expandable heart valve is provided, comprising approaching an inflow side of a cardiac valve with a valve delivery catheter comprising a proximal catheter body, a restraining sheath and a collapsed prosthetic valve having an expandable proximal end and an expandable distal end, wherein the cardiac valve comprises a valve orifice, a valve annulus and a plurality of valve leaflets; positioning the prosthetic valve across the valve orifice; expanding the proximal end of the prosthetic valve against the valve leaflets; and expanding the distal end of the prosthetic valve after expanding the proximal end of the prosthetic valve. The method may further comprise pushing the restraining sheath distally and exposing the proximal end of the prosthetic valve. The method may further comprise pushing the catheter body through the prosthetic valve and contacting the restraining sheath. The method may further comprise pulling the catheter body and the restraining sheath from the prosthetic valve while the catheter body and restraining sheath remain contacted.

In one embodiment, a replacement cardiac valve system is provided, comprising a delivery catheter comprising a catheter body, a retaining structure attached to the distal end of the catheter body and a restraining sheath movably coupled to the distal end of the catheter body; and an expandable heart valve collapsible into the restraining sheath and coupled to the retaining structure of the delivery catheter at an outflow end of the expandable heart valve; wherein the restraining sheath comprises a proximal closed position configured to restrain the expandable heart valve and a distal exposed position that exposes at least a portion of the expandable heart valve. The replacement cardiac valve system may further comprise a taper segment on the delivery catheter proximal to the restraining sheath. The restraining sheath may further comprise a release position that exposes the retaining structure.

The object of the present invention is to transluminally provide a prosthetic valve assembly that includes features for preventing substantial migration of the prosthetic valve assembly once delivered to a desired location within a body. The present invention aims to remedy these significant problems. Another objective of the invention is to provide a support at the time of positioning of the replacement valve that makes it possible to eliminate the problem caused by the native valve sheets, which are naturally calcified, thickened and indurated, or by the residues of the valve sheets after valve resection. Yet another objective of the invention is to provide a support making possible complete sealing of the replacement valve, even in case of an existing cardiac ring which has a surface which is to varying degrees irregular and/or to varying degrees calcified. Another objective of the invention is to have a device that can adapt itself to the local anatomy (i.e. varying diameters of the ring, the subannular zone, the sino-tubular junction) and maintain a known diameter of the valve prosthesis to optimize function and durability. The invention also has the objective of providing a support whose position can be adapted and/or corrected if necessary at the time of implantation.

The present invention is a prosthesis comprising a tissue valve supported on a self-expandable stent in the form of a wire or a plurality of wires that can be contracted radially in order to make possible the introduction of the support-valve assembly into the body of the patient by means of a catheter, and which can be deployed in order to allow this structure to engage the wall of the site where the valve is to be deployed. In one embodiment, the valve is supported entirely within a central, self-expandable, band. The prosthetic valve assembly also includes proximal and distal anchors. In one embodiment, the anchors comprise discrete self-expandable bands connected to the central band so that the entire assembly expands in unison into place to conform more naturally to the anatomy.

The valve can be made from a biological material, such as an animal or human valve or tissue, or from a synthetic material, such as a polymer, and includes an annulus, leaflets and commissure points. The valve is attached to the valve support band with, for example, a suture. The suture can be a biologically compatible thread, plastic, metal or adhesive, such as cyanoacrylate. In one embodiment, the valve support band is made from a single wire bent in a zigzag manner to form a cylinder. Alternatively, the valve support band can be made from a plurality of wires interwoven with one another. The wire can be made from stainless steel, silver, tantalum, gold, titanium, or any suitable tissue or biologically compatible plastic, such as ePTFE or Teflon. The valve support band may have a loop at its ends so that the valve support band can be attached to an upper anchor band at its upper end, and a lower anchor band at its lower end. The link can be made from, for example, stainless steel, silver, tantalum, gold, titanium, any suitable plastic material, or suture.

The prosthetic valve assembly is compressible about its center axis such that its diameter can be decreased from an expanded position to a compressed position. The prosthetic valve assembly may be loaded onto a catheter in its compressed position, and so held in place. Once loaded onto the catheter and secured in the compressed position, the prosthetic valve assembly can be transluminally delivered to a desired location within a body, such as a deficient valve within the heart. Once properly positioned within the body, the catheter can be manipulated to release the prosthetic valve assembly and permit it to into its expanded position. In one embodiment, the catheter includes adjustment hooks such that the prosthetic valve assembly may be partially released and expanded within the body and moved or otherwise adjusted to a final desired location. At the final desired location, the prosthetic valve assembly may be totally released from the catheter and expanded to its fully expanded position. Once the prosthetic valve assembly is fully released from the catheter and expanded, the catheter may be removed from the body.

Other embodiments are contemplated. In one such alternative embodiment, this structure comprises an axial valve support portion that has a structure in the form of a wire or in the form of a network of wires suitable for receiving the replacement valve mounted on it, and suitable for supporting the cardiac ring remaining after the removal of the deficient native valve. The embodiment may further comprise at least one axial wedging portion, that has a structure in the form of a wire or in the form of a network of wires that is distinct from the structure of said axial valve support portion, and of which at least a part has, when deployed a diameter greater or smaller than that of said deployed axial valve support portion, such that this axial wedging portion or anchor is suitable for supporting the wall bordering said existing cardiac ring. The embodiment preferably further comprises at least one wire for connecting the two portions, the wire or wires being connected at points to these portions in such a way as not to obstruct the deployment of said axial portions according to their respective diameters. The embodiment thus provides a support in the form of at least two axial portions that are individualized with respect to one another with regard to their structure, and that are connected in a localized manner by at least one wire; where this wire or these wires do not obstruct the variable deployment of the axial portion with the valve and of the axial wedging portion(s) or anchors. The anchors may be positioned distally or proximally.

The presence of a structure in the form of a wire or in the form of a network of wires in the axial valve support portion makes possible a perfect assembly of this valve with this structure, and the shape as well as the diameter of this axial portion can be adapted for supporting the existing cardiac ring under the best conditions. In particular, this axial valve support portion can have a radial force of expansion such that it pushes back ("impacts") the valve sheets that are naturally calcified or the residues of the valve sheets after valve resection onto or into the underlying tissues, so that these elements do not constitute a hindrance to the positioning of the replacement valve and also allow for a greater orifice area. This structure also makes it possible to support an optional anchoring means and/or optional sealing means for sealing the space between the existing cardiac ring and the replacement valve, as indicated below.

The configuration of each anchor portion can be adapted for supporting the cardiac wall situated at the approach to the existing cardiac ring under the best conditions. In particular, this anchor portion can have a tubular shape with a constant diameter greater than that of the axial valve support portion, or the form of a truncated cone whose diameter increases with distance from the axial valve support portion. By attaching at least one anchor portion to the axial valve support portion, the prosthetic valve assembly assumes a non-cylindrical or toroidal configuration. This non-cylindrical configuration provides an increased radial expansion force and increased diameter at both ends of the prosthetic valve assembly that may tighten the fit between the valve assembly and surrounding tissue structures. The tighter fit from a non-cylindrical configuration can favorably increase the anchoring and sealing characteristics of the prosthesis. The axial valve support portion itself may be non-cylindrical as well.

Preferably, the tubular support has an axial valve support portion in the form of at least two parts, of which at least one is suitable for supporting the valve and of which at least another is suitable for pushing back the native valve sheets or the residues of the native valve sheets after valve resection, into or onto the adjacent tissue in order to make this region able to receive the tubular support. This axial valve support portion eliminates the problem generated by these valve or cardiac ring elements at the time of positioning of the replacement valve. The radial force of this axial valve support portion, by impacting all or part of the valvular tissue or in the wall or its vicinity in effect ensures a more regular surface more capable of receiving the valve support axis. It also ensures a better connection with the wall while reducing the risk of peri-prosthetic leakage. Furthermore, such a structure permits the valve to maintain a diameter within a preset range to ensure substantial coaptivity and avoid significant leakage.

The particular method of maintaining the valve diameter within a preset range described above relates to the general concept of controlling the expanded diameter of the prosthesis. The diameter attained by a portion of the prosthesis is a function of the radial inward forces and the radial expansion forces acting upon that portion of the prosthesis. A portion of the prosthesis will reach its final diameter when the net sum of these forces is equal to zero. Thus, controlling the diameter of the prosthesis can be addressed by addressing the radial expansion force, the radial inward forces, or a combination of both. Changes to the radial expansion force generally occur in a diameter-dependent manner and can occur extrinsically or intrinsically. Resisting further expansion can occur extrinsically by using structural restraints that oppose the intrinsic radial expansion force of the prosthesis, or intrinsically by changing the expansion force so that it does not expand beyond a preset diameter. The first way, referred to previously, relates to controlling expansion extrinsically to a preset diameter to ensure coaptivity. In one embodiment configured to control diameter, a maximum diameter of at least a portion of the support structure may be ensured by a radial restraint provided along at least a portion of circumference of the support structure. The radial restraint may comprise a wire, thread or cuff engaging the support structure. The restraint may be attached to the support structure by knots, sutures or adhesives, or may be integrally formed with the support structure. The radial restraints may also be integrally formed with the support structure during the manufacturing of the support structure. The configuration of the radial restraint would depend upon the restraining forces necessary and the particular stent structure used for the prosthesis. A radial restraint comprising a mechanical stop system is also contemplated. A mechanical stop system uses the inverse relationship between the circumference of the support structure and the length of the support structure. As the support structure radially expands, the longitudinal length of the support structure will generally contract or compress as the wires of the support structure having a generally longitudinal orientation change to a circumferential orientation during radial expansion. By limiting the distance by which the support structure can compress in a longitudinal direction, or the angle to which the support structure wires reorient, radial expansion in turn can be limited to a maximum diameter. The radial restraint may comprise a plurality of protrusions on the support structure where the protrusions abut or form a mechanical stop against another portion of the support structure when the support structure is expanded to the desired diameter.

In an embodiment configured to control the expanded diameter intrinsically for a portion of the support, the radial expansion force of the valve support may be configured to apply up to a preset diameter. This can be achieved by the use of the shape memory effect of certain metal alloys like nickel titanium or Nitinol. When Nitinol material is exposed to body heat, it will expand from a compressed diameter to its original diameter. As the Nitinol prosthesis expands, it will exert a radial expansion force that decreases as the prosthesis expands closer to its original diameter, reaching a zero radial expansion force when its original diameter is reached. Thus, use of a shape memory alloy such as Nitinol is one way to provide an intrinsic radial restraint. A non-shape memory material that is elastically deformed during compression will also exhibit diameter-related expansion forces when allowed to return to its original shape.

Although both shape memory and non-shape memory based material may provide diameter-dependent expansion forces that reach zero upon attaining their original shapes, the degree of force exerted can be further modified by altering the thickness of the wire or structure used to configure the support or prosthesis. The prosthesis may be configured with thicker wires to provide a greater expansion force to resist, for example, greater radial inward forces located at the native valve site, but the greater expansion force will still reduce to zero upon the prosthesis attaining its preset diameter. Changes to the wire thickness need not occur uniformly throughout a support or a prosthesis. Wire thickness can vary between different circumferences of a support or prosthesis, or between straight portions and bends of the wire structure.

The other way of controlling diameter previously mentioned is to alter or resist the radial inward or recoil forces acting upon the support or prosthesis. Recoil forces refer to any radially inward force acting upon the valve assembly that prevents the valve support from maintaining a desired expanded diameter. Recoil forces include but are not limited to radially inward forces exerted by the surrounding tissue and forces caused by elastic deformation of the valve support. Opposing or reducing recoil forces help to ensure deployment of the support structure to the desired diameter.

Means for substantially minimizing recoil are also contemplated. Such means may include a feature, such as a mechanical stop, integral with the support structure to limit recoil. By forming an interference fit between the mechanical stop and another portion of the support structure when the support structure is expanded to its preset diameter, the support structure can resist collapse to a smaller diameter and resist further expansion beyond the preset diameter. The interference fit may comprise an intercalating teeth configuration or a latch mechanism. Alternatively, a separate stent may be applied to the lumen of the cardiac ring to further push aside the native valve leaflets or valve remnants by plastically deforming a portion of the prosthesis. This separate stent may be placed in addition to the support structure and may overlap at least a portion of the support structure. By overlapping a portion of the support structure, the separate stent can reduce any recoil force acting on the support structure. It is also contemplated that this separate stent might be applied to the native lumen before the introduction of the valve prosthesis described herein. Another alternative is to plastically deform the valve assembly diameter beyond its yield point so that the prosthesis does not return to its previous diameter.

At portions of the prosthesis where the control of the expansion force against surrounding tissue is desired, the various methods for controlling diameter can be adapted to provide the desired control of expansion force. Portions of the prosthesis may include areas used for anchoring and sealing such as the axial wedging portions previously described.

Specifically, in order to support the valve, the axial valve support portion can have a part in the form of an undulating wire with large-amplitude undulations, and a part in the form of an undulating wire with small-amplitude undulations, adjacent to said part with large amplitude undulations, having a relatively greater radial force in order to make it possible to push said valvular tissue against or into the wall of the passage. Preferably, the support according to one embodiment of the present invention has two axial wedging portions, one connected to an axial end of said valve support portion and the other to the other axial end of this same valve support portion. These two axial wedging portions thus make it possible to wedge the support on both sides of the existing cardiac ring, and consequently make possible complete wedging of the support in two opposite directions with respect to the treated site. If necessary, for example, in the case in which the passage with the valve has an aneurysm, the support according to the invention has: an axial holding portion, suitable for supporting in the deployed state the wall of the passage, and connecting wires such as the aforementioned connecting wires, connecting said axial valve support portion and said axial holding portion, these wires having a length such that the axial holding portion is situated after implantation a distance away from the axial valve support portion. This distance allows said axial holding portion to rest against a region of the wall of the passage not related to a possible defect which may be present at the approach to the valve, particularly an aneurysm. The length of the connecting wires can also be calculated in order to prevent the axial holding portion from coming into contact with the ostia of the coronary arteries. The aforementioned axial portions (valve support, wedging, holding portions) can have a structure in the form of an undulating wire, in zigzag form, or preferably a structure in diamond-shaped mesh form, the mesh parts being juxtaposed in the direction of the circumference of these portions. This last structure allows a suitable radial force making it possible to ensure complete resting of said portions against the wall that receives them.

As previously mentioned, the support according to the invention can be produced from a metal that can be plastically deformed. The instrument for positioning of the support then includes a balloon which has an axial portion with a predetermined diameter, adapted for realizing the deployment of said axial valve support portion, and at least one axial portion shaped so as to have, in the inflated state, a greater cross section than that of the passage to be treated, in such a way as to produce the expansion of the axial wedging portion placed on it until this axial wedging portion encounters the wall which it is intended to engage. The support according to this embodiment of the present invention can also be produced from a material that can be elastically deformed or even a material with shape memory, such as Nitinol, which can be contracted radially at a temperature different from that of the body of the patient and which regains its original shape when its temperature approaches or reaches that of the body of the patient.

Alternatively, the support may be made from a shape memory material that can be plastically deformed, or may be partially made from a shape memory material and partially made from a material that can be plastically deformed. With this embodiment, the support can be brought, by shape memory or plastic deformation, from a state of contraction to a stable intermediate state of deployment between the state of contraction and the state of total deployment, and then by plastic deformation or shape memory respectively, from said intermediate state of deployment to said state of total deployment. In said intermediate state of deployment, the support is preferably configured such that it remains mobile with respect to the site to be treated. The support may thus be brought to the site to be treated and then deployed to its intermediate state; its position can then possibly be adapted and/or corrected, and then the support be brought to its state of total deployment. One example of a shape memory material that can be plastically deformed may be a nickel-titanium alloy of the type called "martensitic Nitinol" that can undergo plastic deformation by means of a balloon. By using a balloon to expand and stress the alloy beyond its yield point, plastic deformation can occur. Plastic deformation by a balloon of a portion of the prosthesis that has already undergone self-expansion can also be used to compensate for any recoil that occurs.

Advantageously, the support according to the invention has some anchoring means suitable for insertion into the wall of the site to be treated, and is shaped in such a way as to be mobile between an inactive position, in which it does not obstruct the introduction of the support into the body of the patient, and an active position, in which it is inserted into the wall of the site to be treated. Substantially complete immobilization of the support at the site is thus obtained. In particular, this anchoring means can be in the form of needles and can be mounted on the support between retracted positions and radially projected positions. Advantageously, the axial valve support portion has, at the site of its exterior surface, a sealing means shaped in such a way as to absorb the surface irregularities that might exist at or near the existing cardiac ring. This sealing means can consist of a peripheral shell made from a compressible material such as polyester or tissue identical to the valve or a peripheral shell delimiting a chamber and having a radially expandable structure, this chamber being capable of receiving an inflating fluid suitable for solidifying after a predetermined delay following the introduction into said chamber. This sealing means can also include a material that can be applied between the existing cardiac ring and the axial valve support portion, this material being capable of solidifying after a predetermined delay following this application. Specifically, in this case, this material is capable of heat activation, for example, by means of a laser, through the balloon, or capable of activation by emission of light of predetermined frequency, for example, by means of an ultraviolet laser, through the balloon. Said sealing means can also be present in the form of an inflatable insert with a spool-shaped cross section in the inflated state, which can be inserted between the existing cardiac ring and the axial valve support portion, Said spool shape allows this insert to conform to the best extent possible to the adjacent irregular structures and to provide a better seal.

In one embodiment of the invention, a drug-eluting component is contemplated. This component comprises a surface coating or matrix bonding to at least a portion of support structure. Drug elution is well known to those in the art. Potential drugs may include but are not limited to antibiotics, cellular anti-proliferative and anti-thrombogenic drugs.

An assembly and method for removing the native valve is also contemplated. In particular, the invention has the objective of providing a device that gives complete satisfaction with regard to the exeresis and replacement of the valve, while allowing one to operate without opening of the thorax, stopping of the heart and/or opening of the heart, and preventing any diffusion into the circulatory system of fragments of the removed valve. In one embodiment, the assembly comprises: (a) an elongated support element; (b) a first set of elongated blades arranged around the circumference of said elongated element and connected in a pivoting manner to the elongated element at the site of their proximal longitudinal ends, each blade having a sharp edge at the site of its distal longitudinal end and configured to pivot with respect to the elongated element between a folded up (retracted) position, in which they are near the wall of the elongated element in such a way that they do not stand in the way of the introduction and sliding of the device in the body channel in which the valve is located, in particular in the aorta, and an opened out (protracted) position, in which these blades are spread out in the form of a corolla in such a way that their sharp edges are placed in extension of one another and thus constitute a sharp circular edge; (c) a second set of blades arranged consecutively to said first series of blades in the distal direction; the blades of this second set have a structure identical to that of the blades of said first set, wherein the blades of this second series are connected to the elongated element by their distal longitudinal ends and wherein each has a sharp edge at the site of its proximal longitudinal end; (d) means making it possible to bring the blades of said first and second set from their retracted position to their protracted position; (e) means for permitting axial movement of the sets of blades axially relative to one another between a spaced position in which one set of blades can be placed axially on one side of the natural valve while the other set of blades is placed axially on the other side of this valve, and a proximate position in which the sharp circular edges of the two sets of blades may be brought into mutual contact for excising the natural valve.

A method of using this assembly comprises the steps of introducing the assembly percutaneously into said body channel and delivering the assembly to a position where the first and second sets of blades are spaced on opposite sides of the natural valve using the means of identification. The method may further comprise putting in place a system of peripheral aorto-venous heart assistance, extracorporeal circulation or a blood pump through the center of the delivery system for pumping blood, in the case of an aortic valve replacement, from the left ventricle (proximal to the aortic valve) to the aorta (distal to the aortic valve) in order to facilitate the flow of the blood, for the purpose of preventing stagnation of the blood in the heart. One embodiment of a blood flow pump is described further below. After the assembly is positioned in place, the method further comprises spreading the blades of the two sets of blades out; then bringing the two sets closer together to excise the valve. The configuration of these blades makes it possible to execute this cutting in a single operation, minimizing the generation of fragments that can be diffused into the circulatory system. This configuration moreover makes possible precise control of the diameter according to which the natural valve is cut, in view of later calibration of the prosthetic valve. The blades may then be retracted for placement of the prosthetic valve.

The prosthetic valve may be deployed discretely from the assembly, in which case the method may comprise removing the assembly and then separately deploying the prosthetic valve. Preferably however, the assembly comprises a proximal prosthetic valve having an expandable support structure that may occupy a contracted position near the wall of said elongated element for transmission through the body channel, and an expanded position to replace the natural cardiac valve.

After excising the natural valve, the method further comprises sliding the assembly axially in the distal direction in order to bring the prosthetic valve to the desired site in the channel, and then expanding the prosthetic valve support into place. The assembly may then be withdrawn, recovering the excised natural valve.

Preferably, the elongated support element is a tubular catheter permitting blood to flow through it during the excision of the natural valve. The cross section of the channel of this catheter can be sufficient to allow the blood to flow through this channel with or without the help of a pump. Continued blood flow during the excision procedure may limit or eliminate the need for placing the patient under extracorporeal circulation or peripheral aorto-venous heart assistance. The catheter has a lateral distal opening in order to allow the blood to rejoin the body channel, for example the ascending aorta, this opening being arranged in such a way that the length of catheter passed through the blood is as short as possible. Alternatively, the catheter may have a small diameter to facilitate the introduction and delivery of the assembly in the body channel, but a small diameter might require the provision of peripheral circulation by an external assistance system such as an extracorporeal circulation system or peripheral aorto-venous heart assistance.

Preferably, the assembly for excising the native valve includes a distal inflatable balloon, placed at the site of the exterior surface of said elongated element; wherein the balloon is configured so as to occupy a deflated position, in which it has a cross section such that it does not stand hinder introduction and advancement of the assembly within the body channel, and an expanded position. The balloon may be inflated after the positioning of the sets of blades on both sides of the natural valve in order to prevent reflux of the blood during the ablation of the natural valve. If the elongated element is a catheter, this balloon moreover makes it possible to cause blood to flow only through the catheter. Once the prosthetic valve is positioned, the balloon is deflated to re-establish the blood flow through the body channel.

The assembly for excising the native valve may optionally include a distal filter made of flexible material placed on the exterior surface of the elongated element. The filter is configured so that it can occupy a retracted position or a contracted position. This filter serves to capture possible fragments generated by the excision of the natural valve, for removal from the blood circulation. The assembly may include means for moving the sets of blades in the axial direction relative to the balloon and/or from said filter.

The balloon and optional filter may be separate from the assembly, being mounted on an elongated support element specific to them. In case of operation on a mitral valve, this balloon or filter may be introduced into the aorta by a peripheral artery route, and the assembly is itself introduced into the heart by the peripheral venous system, up to the right atrium and then into the left atrium through the interatrial septum, up to the site of the mitral valve. The prosthetic valve can advantageously have a frame made of a material with a shape memory, particularly a nickel-titanium alloy known as "Nitinol." This same valve can have valve leaflets made of biological material (preserved animal or human valves) or synthetic material such as a polymer. When replacing an aortic valve the assembly may be alternatively introduced in a retrograde manner through a peripheral artery (femoral artery) or through a venous approach and transseptally (antegrade).

One embodiment of a system for deploying a prosthetic valve may comprise a blood pump insertable into the lumen of a catheter to facilitate blood flow across the native valve and implantation sites during the implantation procedure. When the catheter is positioned across the implantation site, a proximal opening of the delivery catheter is on one side of the implantation site and the lateral distal opening is on another side of the implantation site. By inserting the blood pump into the catheter lumen between the proximal and lateral distal cells, blood flow across the native valve and implantation sites is maintained during the procedure. One embodiment of the blood pump comprises a rotating impeller attached to a reversible motor by a shaft. When the impeller is rotated, blood flow can be created in either direction along the longitudinal axis of the catheter between the proximal and lateral distal cells to provide blood flow across the implantation site. The pump may be used during the native valve excision step if so carried out.

In one application of the present invention, the prosthetic valve may be implanted by first passing a guidewire inserted peripherally, for instance, through a vein access; transseptally from the right atrium to the left atrium and then snaring the distal end of the guidewire and externalizing the distal end out of the body through the arterial circulation. This placement of the guidewire provides access to the implantation site from both venous and arterial routes. By providing venous access to the native valve, massive valvular regurgitation during the implantation procedure may be avoided by first implanting the replacement valve and then radially pushing aside the native valve leaflets through the venous access route.

Another embodiment of the present invention comprises a prosthesis frame comprising a plurality of structural members arranged to form cells of generally repeating cell patterns throughout the frame. In the preferred embodiment, the structural members are curved to distribute the mechanical stresses associated with frame expansion throughout the axial length of the structural members, rather than concentrating the stress at the junctions between the structural members, as with traditional stent designs having straight structural members. By distributing the mechanical stress of expansion, larger expansion ratios may be achieved, while reducing the risk of mechanical failure associated with larger expansion ratios. The structural members and cell configurations of the prosthesis frame may vary in one of more characteristics within the frame. In a preferred embodiment, larger cell sizes are provided in sections of the frame having larger expansion diameters, while smaller cell sizes are provided in sections of the frame having smaller expansion diameters. The heterogeneity of the cells may be manifested by differing cell sizes, cell shapes, and cell wall configurations and cross-sections.

In a preferred embodiment of the invention, the prosthetic valve comprises a non-cylindrical prosthesis frame. Non-cylindrical frame shapes may be used to improve the anchoring and/or orientation of the prosthetic valve at the desired implantation site. In addition, a prosthesis frame may have one or more sections configured to expand to a restricted or preset diameter rather than to expand until restrained by surrounding anatomical structures. Control of the expansion diameter provides a portion of the prosthesis frame with a reproducible configuration irrespective of the surrounding anatomy. The reproducibility of valve geometry is enhanced in frames with controlled expansion diameters.

To further maintain the control of the expansion diameter of one or more portions of the prosthesis frame, mechanical effects from the variable expansion of adjacent portions of the prosthesis frame may be reduced by providing a stent with a curved outer surface that can distribute the mechanical force exerted by adjacent frame portions throughout the curved configuration and reduce any localized deformation may that result with a traditional cylindrical frame shape.

The implantation of the prosthetic valve may be performed with existing catheter and retaining sheath designs, as known in the art. To further facilitate implantation of such a device, additional delivery catheter features are also contemplated. These additional features include dual sheath withdrawal controls providing at least a slow and a fast sheath withdrawal, and an integrated introducing sheath. It is also contemplated that one or more longitudinal stiffening elements may be provided in the catheter or sheath walls to enhance the column strength and control of the delivery system, while preserving the bendability of the delivery system. To guide the tip of the catheter to a desired position, a proximally controllable steering wire may be provided on the catheter, or alternately, a separate snare may be used to engage and move the tip of the catheter or guidewire toward the desired position.

In one particular embodiment of the invention comprising a self-expandable prosthesis frame, it is contemplated that the device may be implanted into patients having existing prosthetic valves that were surgically or transluminally placed. Such a procedure cannot be performed with balloon-expandable prosthetic valves because the rigidity of the existing prosthetic valve prevents adequate overexpansion of the prosthetic valve to achieve anchoring of the balloon-expandable valve. Without overexpansion, once the balloon is released, the prosthesis frame tends to rebound and radially contract, thus requiring that balloon-expandable prostheses be overexpanded in order to achieve the desired final expansion configuration.

Although some embodiments of the invention are described using an example of a prosthetic valve for treatment of aortic valve disorders, prostheses configured for use in other cardiac valve or circulatory system positions or are also contemplated, including but not limited to those at the mitral, pulmonic and tricuspid valve positions. Valve implantation in any of a variety of congenital cardiac malformations or other circulatory system disorders are also contemplated and may include implantation of valves into the aortic root, ascending aorta, aortic arch or descending aorta. It is also understood that the general prosthesis frame and valve may be incorporated into other types of medical devices, such as vascular grafts for abdominal aortic aneurysms.

In one embodiment, a prosthetic valve assembly is provided, comprising a prosthesis frame having a first and second end and having a reduced and expanded configuration, the frame comprising a first zone proximal the first end, a second zone proximal the second end, and a third zone therebetween, said zones positioned axially with respect to each other, wherein the fully expanded diameter of the first zone is different than that of the second zone; and a valve engaged to the prosthesis frame. The valve may be primarily supported by the third zone. The fully expanded diameter of the third zone may be less than those of the first and second zones. The third zone may comprise a generally concave portion. The prosthesis frame may be self-expanding. The first zone of the prosthesis frame may be tapered. The second zone may comprise a generally bulbous configuration. The first zone may comprise a generally tapered configuration. The first zone may be adapted to wedge against a patient's native valve leaflets and/or a patient's surgically implanted valve leaflets. The first zone may also be adapted to deflect one or more commissure posts of a surgically implanted heart valve. In some embodiments, no substantial continuous portion of the prosthesis frame is of constant diameter. The second end may have a diameter less than the greatest fully expanded diameter of the second zone. The prosthesis frame may comprise a plurality of cells defined by one or more structural members, wherein the cells that are configured so as to be expandable. A portion of the plurality of cells may be homogeneous in shape, heterogeneous in shape, homogeneous in size, heterogeneous in size, homogeneous in structural member configuration, and/or heterogeneous in structural member configuration. At least some of the structural members may have varied cross-sectional configurations along their length.

In another embodiment, a prosthetic valve assembly for treating a patient is provided, comprising a valve for controlling blood flow; a non-cylindrical means for maintaining and supporting the geometry of the valve means; and an anchor attached to the non-cylindrical means. The maintaining and supporting means may comprise a prosthesis frame comprising a plurality of expandable cells and having a non-uniform diameter along its length.

In another embodiment, a prosthetic valve assembly is provided, comprising a prosthesis frame having a first zone, a second generally bulbous zone having a maximum expanded diameter greater than that of the first zone, and a valve support zone having a maximum expanded diameter smaller than those of the first and second zones. The first zone may be tapered. The valve support zone may be generally concave in outer configuration. The valve assembly may further comprise a valve supported by the valve support zone. The valve may be a tri-cuspid tissue valve. The frame may be self-expandable. A method of implanting the valve assembly described above is also provided, the method comprising the steps of mounting the valve assembly onto a catheter suitable for percutaneous and vascular delivery and deploying said valve assembly within an appropriate native lumen of the patient. The step of deploying may comprise deploying the valve assembly within a previously-implanted prosthetic cardiac valve.

In another embodiment, a method of implanting the valve assembly in a patient is provided, the method comprising providing a prosthetic valve assembly comprising a prosthesis frame having a first zone, a second generally bulbous zone having a maximum expanded diameter greater than that of the first zone, and a valve support zone having a maximum expanded diameter smaller than those of the first and second zones, said prosthetic valve assembly mounted onto a catheter suitable for percutaneous and vascular delivery and deploying said valve assembly within an appropriate native lumen of the patient. Deploying may comprise deploying the valve assembly within a previously-implanted prosthetic cardiac valve.

In one embodiment, a method for treating a patient is provided, comprising inserting a self-expanding valve into the lumen of a previously-implanted cardiovascular device with a lumen of a patient. The implanted cardiovascular device may be a surgically implanted cardiac valve or an aorto-ventricular conduit. The method may further comprise expanding the self-expanding valve against one or more valve leaflets of a patient without contacting a valve annulus of the patient. The surgically implanted cardiac valve may comprise at least one commissure post and a bloodflow cross-sectional area. The method may further comprise outwardly deflecting the at least one commissure post. The method may further comprise deflecting the at least one commissure post to increase the bloodflow cross-sectional area. At least a portion of the at least one commissure post may be moved at least about 1 mm, at least about 1.5 mm, or at least about 2 mm. The previously-implanted cardiovascular device may comprise a valve leaflet support with a cross-sectional area. The method may further comprise deforming the valve leaflet support to increase the cross-sectional area. In some embodiments, at least a portion of the at least one commissure post is deflected at least about 3 degrees, at least about 5 degrees, or at least about 10 degrees. The at least a portion of the at least one commissure post may deflected from a generally radially inward position to a generally parallel position, or from a generally radially inward position to generally radially outward position.

In one embodiment, a method for implanting a cardiovascular device is provided, comprising inserting an expandable heart valve into a vascular system of a patient, anchoring the expandable heart valve against a distal surface of one or more valve leaflets of the patient without contacting an annulus surface of the patient. The one or more valve leaflets may be native valve leaflets and/or artificial valve leaflets.

In one embodiment, a method for treating a patient is provided, comprising inserting a self-expanding valve into the lumen of a previously-implanted cardiovascular device with the native lumen of a patient. The implanted cardiovascular device may be a surgically implanted cardiac valve or an aorto-ventricular conduit.

In another embodiment, a method for implanting a cardiovascular device is provided, comprising providing a cardiovascular device located on a delivery system; inserting the delivery system through an aortic arch of a patient from a first arterial access point; inserting a snare from a second arterial access point; grasping the delivery system with the snare; and manipulating the snare to align the delivery system with a lumen of the patient's aortic valve. The cardiovascular device may be a self-expanding valve. The delivery system may comprise a catheter and guidewire, and/or a catheter and retaining sheath. The grasping step may comprise grasping the catheter with the snare or grasping the guidewire with the snare. The catheter may comprise a retaining sheath controller. The retaining sheath controller may comprise one or more detents or stops for a defined sheath position. The catheter may comprise a multi-rate retaining sheath controller, one or more longitudinal stiffening elements, a catheter circumference and two longitudinal stiffening elements located generally on opposite sides of the catheter circumference. The retaining sheath may comprise one or more longitudinal stiffening elements, and/or a retaining sheath circumference and two longitudinal stiffening elements located generally on opposite sides of the retaining sheath circumference. The delivery system may comprise a catheter and introducer sheath. The catheter may comprise a distal delivery section and a proximal body having a reduced diameter relative to the distal delivery section. The introducer sheath may be integrated with the proximal body of the catheter.

In another embodiment, disclosed is a method for delivering a self-expandable heart valve, comprising approaching an inflow side of a cardiac valve with a valve delivery catheter, wherein the delivery catheter comprising a proximal catheter body, a restraining sheath and a collapsed prosthetic valve having an expandable proximal end and an expandable distal end, wherein the cardiac valve comprises a valve orifice, a valve annulus and a plurality of valve leaflets; positioning the prosthetic valve across the valve orifice; expanding the proximal end of the prosthetic valve against the valve leaflets; and expanding the distal end of the prosthetic valve after expanding the proximal end of the prosthetic valve.

In some embodiments, the method also includes the step of pushing the restraining sheath distally and exposing the proximal end of the prosthetic valve. The method can also include the step of pushing the catheter body through the prosthetic valve and contacting the restraining sheath. In some embodiments, the method further includes pulling the catheter body and the restraining sheath from the prosthetic valve while the catheter body and the restraining sheath remain contacted.

Also disclosed herein is a replacement cardiac valve system, including a delivery catheter comprising a catheter body, a retaining structure attached to the distal end of the catheter body and a restraining sheath movably coupled to the distal end of the catheter body; and an expandable heart valve collapsible into the restraining sheath and coupled to the retaining structure of the delivery catheter at an outflow end of the expandable heart valve. The restraining sheath includes a proximal closed position configured to restrain the expandable heart valve and a distal exposed position that exposes at least a portion of the expandable heart valve. The system can also include a taper segment on the delivery catheter proximal and/or distal to the restraining sheath. The sheath may also include a release position that exposes the retaining structure.

Also disclosed herein is a catheter for delivering a self expandable prosthesis, the catheter comprising an elongate body; a distal portion having a section around which the prosthesis can be mounted; and a sheath having a proximal end, and being movable over the prosthesis mounting section in a distal direction from a position substantially covering the prosthesis mounting section to a position substantially uncovering the prosthesis mounting section, such that, in use, movement of the proximal end of the sheath exposes a prosthesis placed in the mounting section. In some embodiments, the distal portion comprises a zone of reduced cross-section to form the prosthesis mounting section. In some embodiments, the prosthesis mounting section comprises a proximal end and the catheter further comprises a projection adjacent the proximal end of the mounting section configured to cooperate with the proximal end of the sheath to minimize interference between the proximal end of the sheath and a deployed prosthesis when, in use, the catheter is withdrawn through the deployed prosthesis. In some embodiments, the projection comprises an area of greater cross-section than that of the mounting section, the cross section of the projection extending around the catheter approximating the cross-section of the proximal end of the sheath. In some embodiments, the projection extends by means of a sloping surface extending from adjacent the prosthesis mounting section towards an outer surface of the catheter.

Also disclosed is a kit comprising a catheter for delivering a self expandable prosthesis, the catheter comprising an elongate body; a distal portion having a section around which the prosthesis can be mounted; a sheath having a proximal end, and being movable over the prosthesis mounting section in a distal direction from a position substantially covering the prosthesis mounting section to a position substantially uncovering the prosthesis mounting section, such that, in use, movement of the proximal end of the sheath exposes a prosthesis placed in the mounting section. The kit can also include the prosthesis. The prosthesis can be a heart valve in some embodiments. The kit can also include a guidewire.

The above embodiments and methods of use are explained in more detail below.

BRIEF DESCRIPTION OF THE DRAWINGS

FIG. 1 is a cross-sectional side view of one embodiment of an assembly of the present invention for removing and replacing a native heart valve percutaneously;

FIG. 2 is a cross-section axial view of the assembly of FIG. 1 taken at line II-II, shown in a closed condition;

FIG. 3 is a cross-section axial view of the assembly of FIG. 1 taken at line II-II, shown in an opened condition;

FIGS. 5 to 9 are schematic views of the assembly of the present invention positioned in a heart, at the site of the valve that is to be treated, during the various successive operations by means of which this valve is cut out and the prosthetic valve shown in FIG. 4 deployed;

FIG. 55 depicts one embodiment of the present invention comprising loop elements released from a delivery catheter after withdrawal of an outer sheath;

FIGS. 56A and 56B represent one embodiment of the radial restraint comprising a wire interwoven into the support structure;

FIGS. 73A through 73E are schematic views of another embodiment of a laser cut anti-recoil feature, in various states of expansion;

FIG. 92 is a schematic representation of a retrograde approach to the aortic valve to implant a self-expanding valve.

FIG. 93 is a schematic representation of an antegrade approach to the aortic valve using a catheter with a pull-back sheath to implant a self-expanding valve.

FIG. 94 is a schematic representation of transeptal approach to the aortic valve using a catheter with a push-forward sheath to implant a self-expanding valve.

FIG. 95 is a longitudinal cross-sectional view through a catheter with a push-forward sheath.

FIG. 96 is a longitudinal cross-sectional view through a catheter with a pull-back sheath.

DETAILED DESCRIPTION OF THE PREFERRED EMBODIMENT

Figure 9:
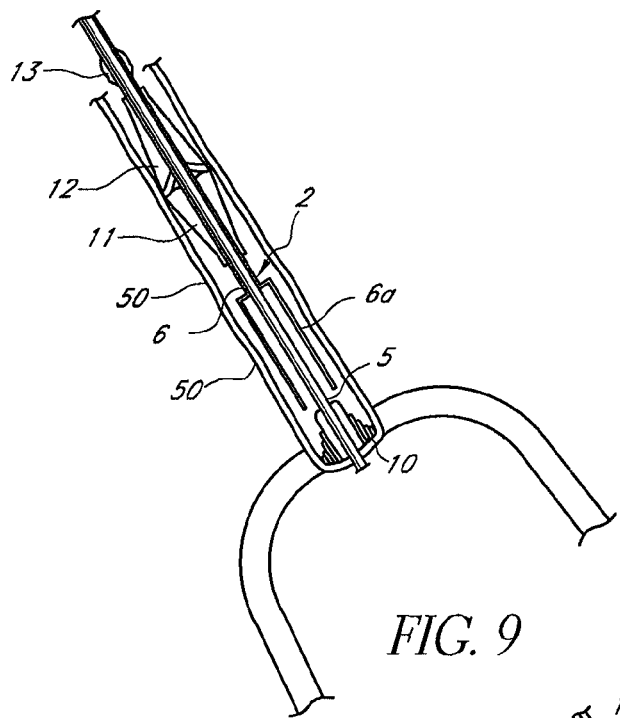

Reference is now made to the figures wherein like parts are designated with like numerals throughout. FIGS. 1 to 3 represent a device 1 for replacing a heart valve by a percutaneous route. This device comprises a tubular catheter 2 formed from three tubes 5, 6, 7 engaged one inside the other and on which there are placed, from the proximal end to the distal end (considered with respect to the flow of blood, that is to say from right to left in FIG. 1), a prosthetic valve 10, two series of blades 11, 12, a balloon 13 and a filter 14. The three tubes 5, 6, 7 are mounted so that they can slide one inside the other. The interior tube 5 delimits a passage 15, the cross section of which is large enough to allow blood to flow through it. At the proximal end, the intermediate tube 6 forms a bell housing 6a delimiting, with the interior tube 5, an annular cavity 17 in which the prosthetic valve 10 is contained in the furled condition.

Figure 4:
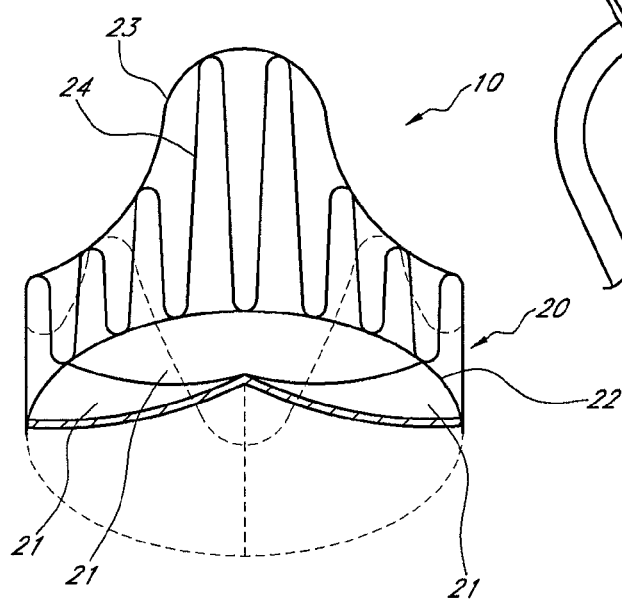
FIG. 4 is a perspective schematic view of one embodiment of a prosthetic valve of the present invention.

FIG. 4 shows that this valve 10 comprises an armature 20 and valve leaflets 21 mounted so that they are functionally mobile on this armature 20. The armature comprises a collection of wires 22, 23, 24 made of shape memory material, particularly of nickel-titanium alloy known by the name of "NITINOL;" namely, (i) a proximal end wire 22 which, when the valve 10 is in the deployed state, has a roughly circular shape; (ii) a distal end wire 23 forming three corrugations in the axial direction, these corrugations being distributed uniformly around the circumference of the valve 10, and (iii) an intermediate wire 24 forming longitudinal corrugations between the wires 22 and 23, this wire 24 being connected to the latter ones via the ends of each of these corrugations. The valve leaflets 21 for their part are made of biological material (preserved human or animal valve leaflets) or of synthetic material, such as a polymer. The armature 20 may, when its material is cooled, be radially contracted so that the valve 10 can enter the cavity 17. When this material is heated to body temperature, this armature 20 returns to its original shape, depicted in FIG. 4, in which it has a diameter matched to that of a bodily vessel, particularly the aorta, in which the native valve that is to be treated lies. This diameter of the armature 20 is such that the valve 10 bears against the wall of the bodily vessel and is immobilized in the axial direction with respect to that vessel.

Each series of blades 11, 12 comprises metal elongate blades 30 and an inflatable balloon 31 situated between the catheter 2 and these blades 30. The blades 30 have a curved profile and are arranged on the circumference of the catheter 2, as shown in FIGS. 2, 3 and 3A. The blades 30 of the proximal series 11 are connected pivotably to the tube 6 by their proximal ends and comprise a cutting distal edge 30a, while the blades 30 of the distal series 12 are connected pivotably to the exterior tube 7 by their distal ends and comprise a cutting proximal edge 30b. The connection between the blades 30 and the respective tubes 6 and 7 is achieved by welding the ends of the blades 30 together to form a ring, this ring being fixed axially to the corresponding tube 6, 7 by crimping this ring onto this tube 6, 7, the pivoting of the blades 30 being achieved by simple elastic deformation of these blades 30. This pivoting can take place between a position in which the blades 30 are furled, radially internally with respect to the catheter 2 and shown in FIGS. 1 and 2, and a position in which these blades 30 are unfurled, radially externally with respect to this catheter 2 and shown in FIG. 3. In the furled position, the blades 30 lie close to the wall of the tube 6 and partially overlap each other so that they do not impede the introduction and the sliding of the device 1 into and in the bodily vessel in which the native valve that is to be treated lies; in said unfurled position, the blades 30 are deployed in a corolla so that their cutting edges 30a, 30b are placed in the continuation of one another and thus constitute a circular cutting edge visible in FIG. 3.

Each balloon 31, placed between the tube 3 and the blades 30, may be inflated from the end of the catheter 2 which emerges from the patient, via a passage 32 formed in the tube 6. It thus, when inflated, allows the blades 30 to be brought from their furled position into their unfurled position, and performs the reverse effect when deflated. The axial sliding of the tube 6 with respect to the tube 7 allows the series of blades 11, 12 to be moved axially toward one another, between a spaced-apart position shown in FIG. 1, and a close-together position. In the former of these positions, one series of blades 11 may be placed axially on one side of the native valve while the other series of blades 12 is placed axially on the other side of this valve, whereas in the latter of these positions, the circular cutting edges of these two series of blades 11, 12 are brought into mutual contact and thus cut through the native valve in such a way as to detach it from said bodily vessel. The tubes 5 to 7 further comprise marks (not visible in the figures) in barium sulfate allowing the axial position of the device 1 with respect to the native valve to be identified percutaneously so that each of the two series of blades 11, 12 can be placed on one axial side of this valve. These tubes 5 to 7 also comprise lateral distal cells (not depicted) to allow the blood to reach the bodily vessel, these cells being formed in such a way that the length of catheter 2 through which the blood flows is as short as possible, that is to say immediately after the filter 14, in the distal direction.

The balloon 13 is placed on the exterior face of the tube 7, distally with respect to the series 12. This balloon 13 has an annular shape and is shaped to be able to occupy a furled position in which it has a cross section such that it does not impede the introduction and sliding of the device 1 into and in said bodily vessel, and an unfurled position, in which it occupies all of the space between the exterior face of the tube 7 and the wall of said bodily vessel and, via a peripheral edge 13a which it comprises, bears against this wall.

The filter 14 is placed distally with respect to the balloon 13, on the tube 7, to which it is axially fixed. This filter 14 is made of flexible material, for example polyester netting, and is shaped to be able to occupy a furled position in which it has a cross section such that it does not impede the introduction and sliding of the device 1 into and in said bodily vessel, and an unfurled position in which it occupies all of the space between the exterior face of the catheter 2 and the wall of this vessel and, via a peripheral edge 14a which it comprises, bears against this wall.

Figure 10:
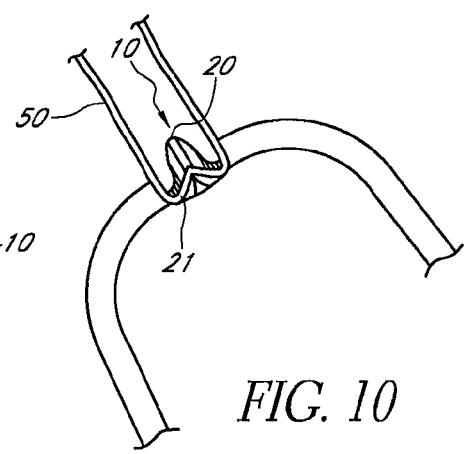
FIG. 10 is a schematic view of the prosthetic valve shown of FIG. 4 shown in a deployed state.

An inflatable balloon 35 is placed between the tube 7 and the filter 14 so as, depending on whether it is inflated or deflated, to bring the filter 14 into its respective unfurled and furled positions. In practice, as shown by FIGS. 5 to 9, the device 1 is introduced into said bodily vessel 50 by a percutaneous route and is slid along inside this vessel 50 until each of the series 11, 12 of blades is placed on one side of the native valve 55 that is to be treated (FIG. 5). This position is identified using the aforementioned marks. When the device is in this position, the proximal part of the catheter 2 is situated in the heart, preferably in the left ventricle, while the aforementioned distal lateral cells are placed in a peripheral arterial vessel, preferably in the ascending aorta. The balloons 13 and 35 are inflated in such a way as to cause blood to flow only through the passage 15 and prevent blood reflux during the ablation of the valve 55. A peripheral perfusion system is set in place to facilitate this flow, as further described below in connection with FIGS. 50 through 52. The blades 30 of the two series 11, 12 are then deployed (FIG. 6) by inflating the balloons 31, then these two series 11, 12 are moved closer together by sliding the tube 6 with respect to the tube 7, until the valve 55 is cut through (FIG. 7). The blades 30 are then returned to their furled position by deflating the balloons 31 while at the same time remaining in their close-together position, which allows the cut-out valve 55 to be held between them. The device 1 is then slid axially in the distal direction so as to bring the bell housing 6a to the appropriate position in the vessel 50 (FIG. 8), after which the valve 10 is deployed by sliding the tube 6 with respect to the tube 5 (FIG. 9). The balloons 13 and 35 are deflated then the device 1 is withdrawn and the cut-out valve 55 is recovered (FIG. 10).

Figure 11:
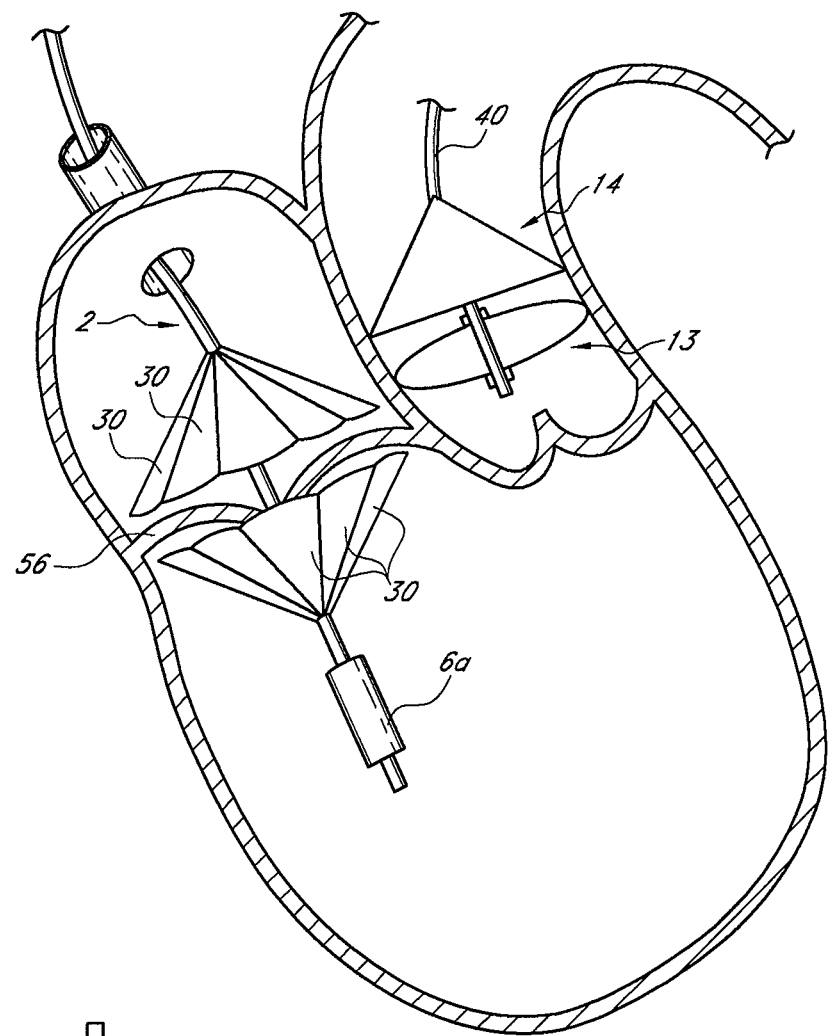
FIG. 11 is a schematic view of an alternative embodiment of the assembly of the present invention shown treating a mitral valve.

FIG. 11 shows a second embodiment of the device 1, allowing operation on a mitral valve 56. The same reference numerals are used to denote the same elements or parts as the aforementioned, as long as these elements or parts are identical or similar in both embodiments. In this case, the tubular catheter is replaced by a support wire 2, on which one of the series of blades is mounted and by a tube engaged over and able to slide along this wire, on which tube the other series of blades is mounted; the passages for inflating the balloons 31 run along this support wire and this tube; the balloon 13 and the filter 14 are separate from the device 1 and are introduced into the aorta via a peripheral arterial route, by means of a support wire 40 along which the passages for inflating the balloons 13 and 35 run. The device 1, devoid of balloon 13 and the filter 14, is for its part introduced into the heart through the peripheral venous system, as far as the right atrium then into the left atrium through the inter-auricular septum, as far as the valve 56. For the remainder, the device 1 operates in the same way as was mentioned earlier. The invention thus provides a device for replacing a heart valve by a percutaneous route, making it possible to overcome the drawbacks of the prior techniques. Indeed the device 1 is entirely satisfactory as regards the cutting-away of the valve 55, 56, making it possible to operate without stopping the heart and making it possible, by virtue of the filter 14, to prevent any dispersion of valve fragments 55, 56 into the circulatory system.

Figure 12:
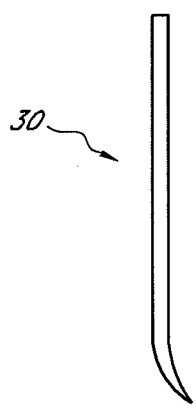
FIG. 12 is a cross-sectional view of a section of a blade used in excising the native valve.
Figure 13:
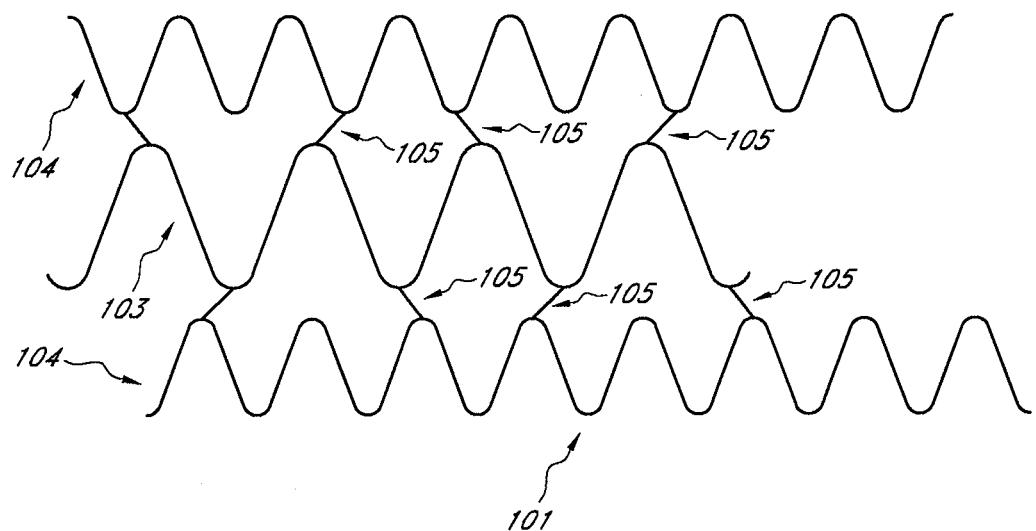
FIG. 13 is a schematic view of one embodiment of the support structure of the prosthesis assembly of the present invention.
Figure 14:
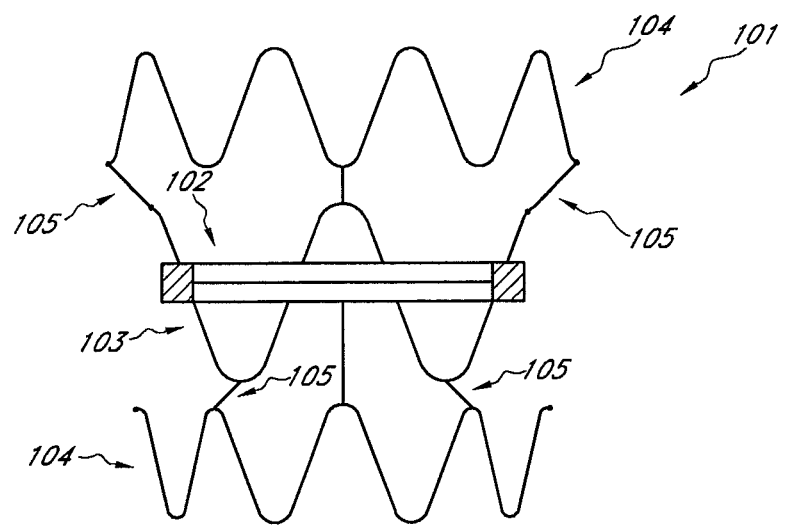
FIG. 14 is a cross-sectional view of the support of FIG. 13 showing a heart valve supported by the central portion of the support.

The above device may comprise a fourth tube, engaged on and able to slide along the tube 7, this fourth tube comprising the balloon and the filter mounted on it and allowing said series of blades to be moved in the axial direction independently of said balloon and/or of said filter; the blades may be straight as depicted in the drawing or may be curved toward the axis of the device at their end which has the cutting edge, so as to eliminate any risk of lesion in the wall of the bodily vessel, as shown in FIG. 12; the filter 14 may be of the self-expanding type and normally kept in the contracted position by a sliding tube, which covers it, making the balloon 35 unnecessary.

FIGS. 13 to 16 represent tubular support 101 for positioning, by percutaneous route, of replacement heart valve 102. The support structure 101 includes median portion 103, which contains valve 102, two extreme wedging portions 104 and wires 105 for connecting these portions 103 and 104. Median portion 103 also includes peripheral shell 106 provided with anchoring needles 107 and shell 108 made of compressible material. As is particularly apparent from FIG. 12, each of portions 103 and 104 is formed with an undulating wire, and wires 105 connect pointwise the ends of the undulations of portion 103 to the end of an adjacent wave of portion 104. Portions 104, seen in expanded form, have lengths greater than the length of portion 103, so that when the ends of the wires respectively forming portions 103 and 104 are connected in order to form the tubular support structure 101, the diameter of portion 103 is smaller than the diameter of portions 104.

Figure 15:
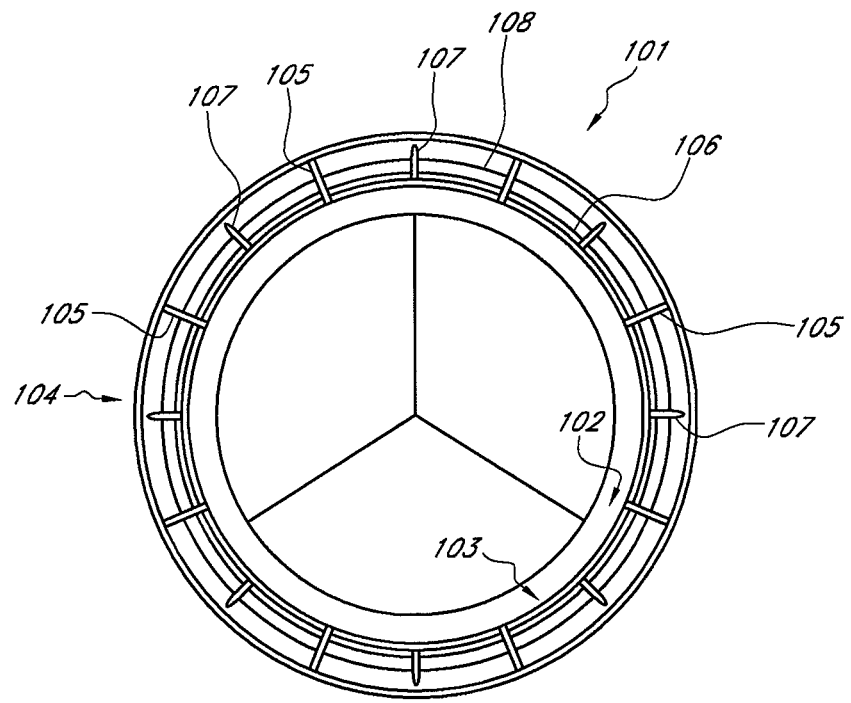
FIG. 15 is an end view of the support of FIGS. 13 and 14 in the deployed state.
Figure 16:
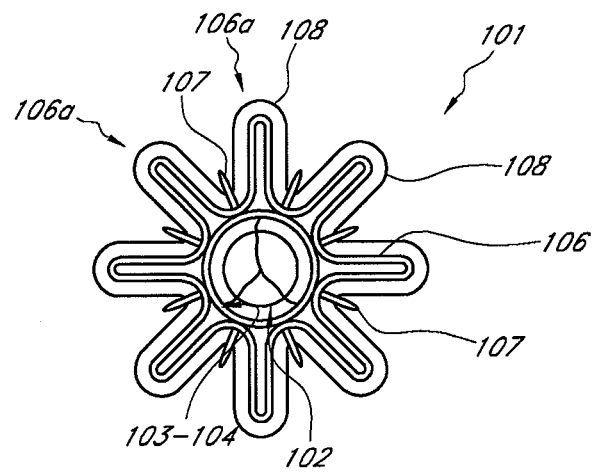
FIG. 16 is an end view of the support of FIGS. 13 and 14 in the contracted state.
Figure 17:
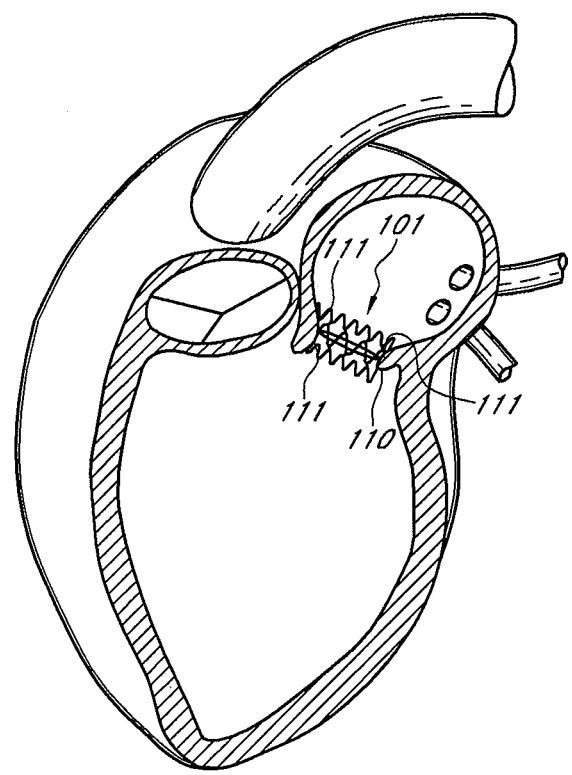
FIG. 17 is a schematic view of a heart with an embodiment of the present inventive prosthesis shown deployed in place.

The diameter of portion 103 is such that portion 103 can, as shown by FIG. 17, support cardiac ring 110 that remains after removal of the deficient native valve, while portions 104 support walls 111 bordering ring 110. These respective diameters are preferably such that said supporting operations take place with slight radial restraint of ring 110 and walls 111. Portion 103 presents in the deployed state a constant diameter. Portions 104 can have a constant diameter in the form of a truncated cone whose diameter increases away from portion 103. The entire support structure 101 can be made from a material with shape memory, such as the nickel-titanium alloy known as "Nitinol." This material allows the structure to be contracted radially, as shown in FIG. 16, at a temperature different from that of the body of the patient and to regain the original shape shown in FIGS. 14 and 15 when its temperature approaches or reaches that of the body of the patient. The entire support structure 101 can also be made from a material that can be expanded using a balloon, such as from medical stainless steel (steel 316 L). Valve 102 can be made of biological or synthetic tissue. It is connected to portion 103 by sutures or by any other appropriate means of attachment. It can also be molded on portion 103. Shell 106 may be made of "Nitinol." It is connected to the undulations of portion 103 at mid-amplitude, and has needles 107 at the site of its regions connected to these undulations. Needles 107 consist of strands of metallic wire pointed at their free ends, which project radially towards the exterior of shell 106.

This shell can take on the undulating form that can be seen in FIG. 16 in the contracted state of support 101 and the circular form which can be seen in FIG. 4 in the deployed state of this support 101. In its undulating form, shell 106 forms undulations 106a projecting radially on the outside of support 101, beyond needles 107, so that these needles 107, in the retracted position, do not obstruct the introduction of support 101 in a catheter or, once support 101 has been introduced into the heart using this catheter, do not obstruct the deployment out of this support 1. The return of shell 106 to its circular form brings needles 107 to a position of deployment, allowing them to be inserted in ring 110 in order to complete the anchoring of support 101. Shell 108 is attached on shell 106. Its compressible material allows it to absorb the surface irregularities that might exist at or near ring 110 and thus to ensure complete sealing of valve 102.

Figure 18:
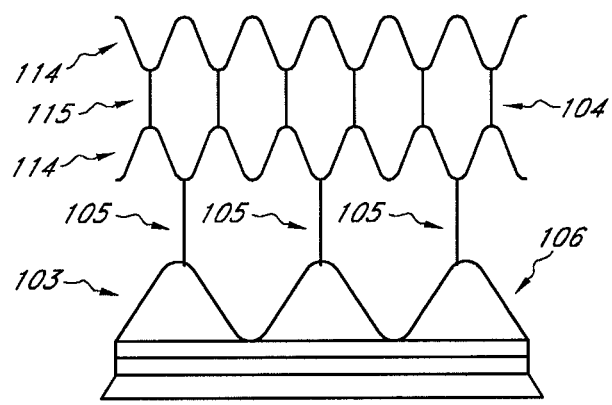
FIG. 18 is a schematic view of an alternative embodiment of the present invention.
Figure 19:
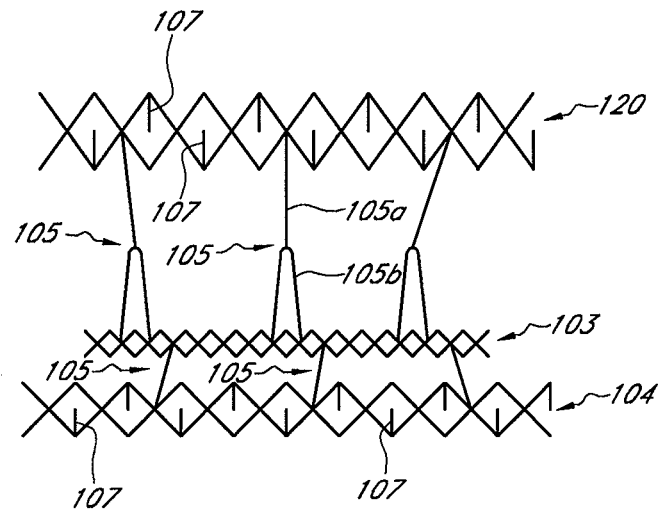
FIG. 19 is schematic view of an alternative embodiment of the present invention.

FIG. 18 shows a support structure 101 having a single portion 104 connected to portion 103 by wires 105. This portion 104 is formed by two undulating wires 114 connected together by wires 115. FIG. 19 shows a support structure 101 that has portion 103 and portion 104 connected by connecting wires 105. These portions 103 and 104 have diamond-shaped mesh structures, these mesh parts being juxtaposed in the direction of the circumference of these portions and connected together at the site of two of their opposite angles in the direction of the circumference of these portions 103 and 104. Wires 105 are connected to these structures at the site of the region of junction of two consecutive mesh parts. These mesh parts also have anchoring hooks 107 extending through them from one of their angles situated in the longitudinal direction of support 101.

Figure 20:
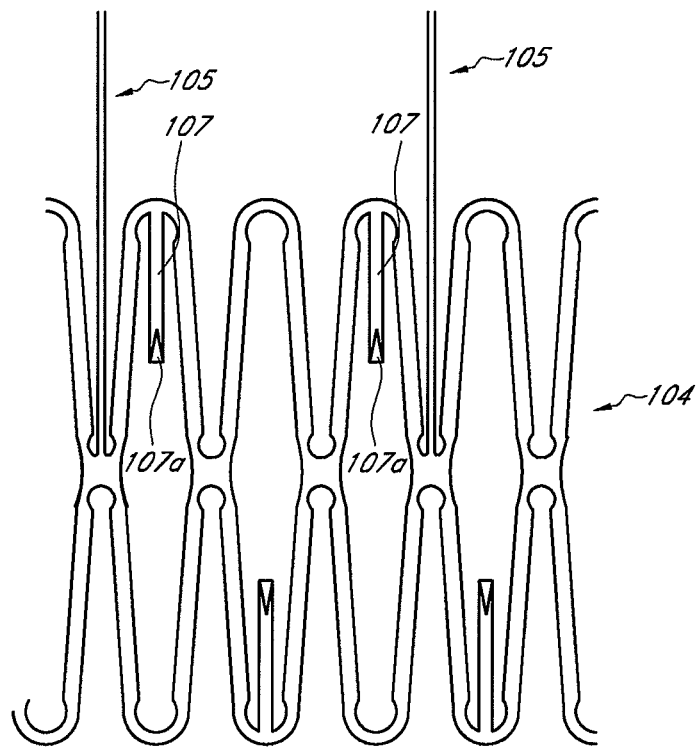
FIG. 20 is a detail view of a part of the support structure of one embodiment of the present invention.
Figures 23, 24:
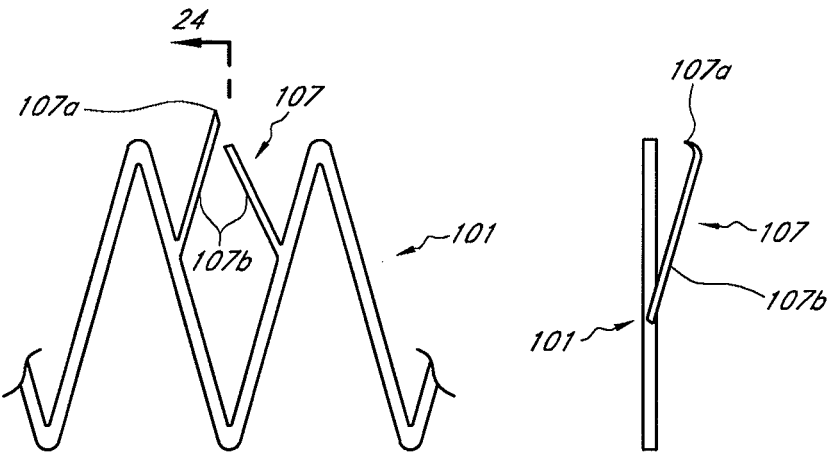
FIG. 23 is a detail view of the support of FIG. 22 shown in the contracted state.
FIG. 24 is a detail view of the support of FIG. 23 taken along line 23-23.
Figures 25, 26:
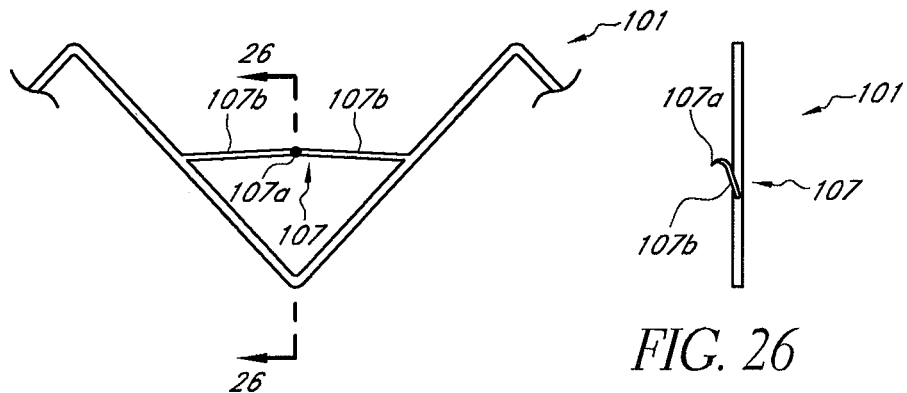
FIG. 25 is a detail view of the support of FIG. 22 shown in the expanded state.
FIG. 26 is a detail view of the support of FIG. 25 taken along line 25-25.

FIG. 20 illustrates, in an enlarged scale, the structure of this portion 104 and of a part of wires 105, as cut, for example, with a laser from a cylinder of stainless steel, and after bending of sharp ends 107a of hooks 107. These hooks, in a profile view, can have the shape as shown in FIG. 24 or 26. The structure represented in FIG. 19 also has axial holding portion 120, which has a structure identical to that of portion 104 but with a coarser mesh size, and three wires 105 of significant length connecting this portion 120 to portion 103. These wires 105, on the side of portion 120, have a single link 105a and on the side of portion 103, a double link 105b. Their number corresponds to the three junctions formed by the three valves of valve 102, which facilitates mounting of valve 102 on support 101 thus formed. The support according to FIG. 19 is intended to be used, as appears in FIG. 21, when the body passage with the valve to be replaced, in particular the aorta, has a variation in diameter at the approach to the valve. The length of wires 105 connecting portions 103 and 120 is provided so that after implantation, portion 120 is situated in a non-dilated region of said body passage, and this portion 120 is provided so as to engage the wall of the passage.

Figure 22:
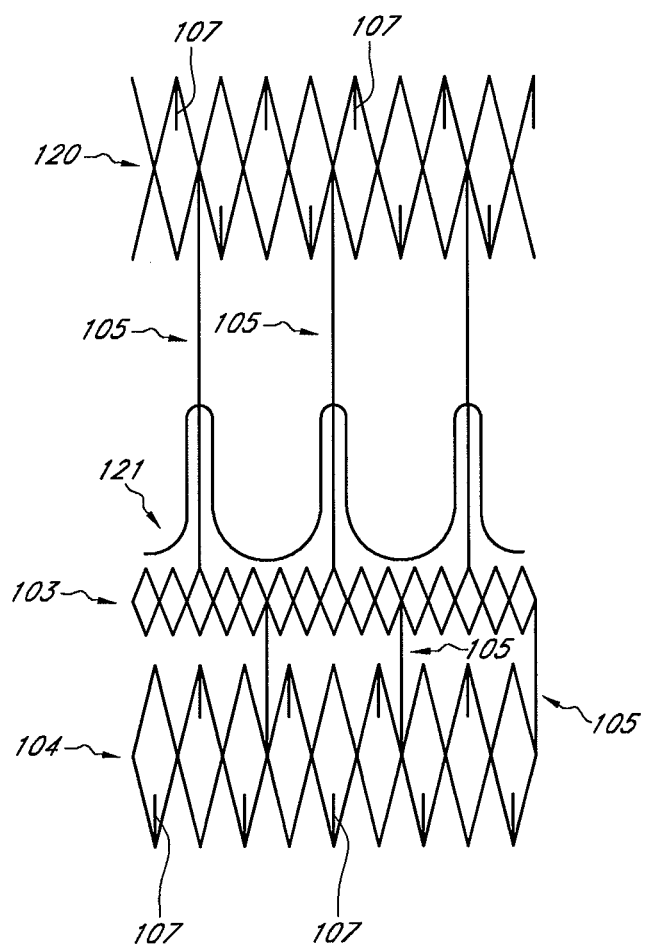
FIG. 22 is schematic view of an alternative embodiment of the present invention.

FIG. 22 shows a structure similar to that of FIG. 19 but unexpanded, except that the three wires 105 have a single wire structure but have an undulating wire 121 ensuring additional support near portion 103. This wire 121 is designed to support valve 102 with three valve leaflets. FIGS. 23 to 26 show an embodiment variant of the structure of portions 103, 104 or 120, when this structure is equipped with hooks 107. In this case, the structure has a zigzagged form, and each hook 107 has two arms 107b; each of these arms 107b is connected to the other arm 107b at one end and to an arm of structure 101 at its other end. The region of junction of the two arms 107b has bent hooking pin 107a.

Figure 27:
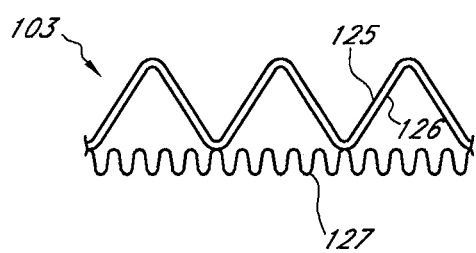
FIG. 27 is a schematic view of an alternative embodiment of the present invention.
Figure 28:
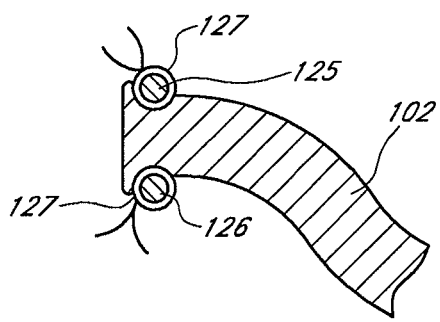
FIG. 28 is a detailed cross section view of the support of FIG. 27.
Figure 29:
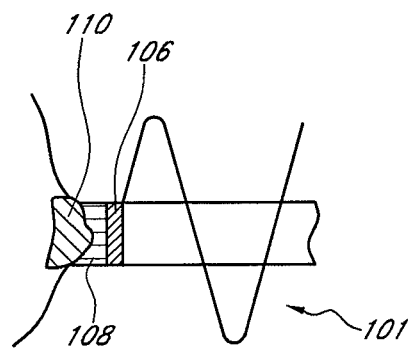
FIG. 29 is a partial schematic view in longitudinal section of the support of the present invention and of a calcified cardiac ring.
Figure 30:
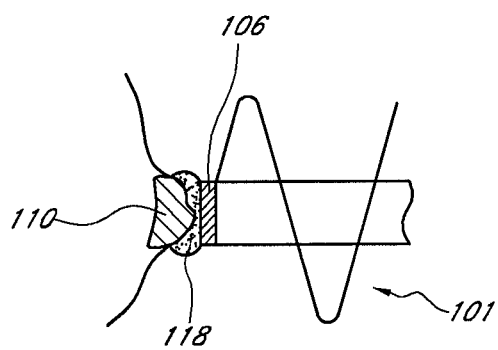
FIG. 30 is a schematic view of an alternative to the support of FIG. 29.

FIG. 27 shows portion 103 that has two undulating wires 125, 126 extending in the vicinity of one another and secondary undulating wire 127. As represented in FIG. 28, wires 125, 126 can be used to execute the insertion of valve 102 made of biological material between them and the attachment of this valve 102 to them by means of sutures 127. FIG. 29 shows a part of support 101 according to FIGS. 13 to 17 and the way in which the compressible material constituting shell 108 can absorb the surface irregularities possibly existing at or near ring 110, which result from calcifications. FIG. 30 shows support 101 whose shell 106 has no compressible shell. A material can then be applied, by means of an appropriate cannula (not represented), between ring 110 and this shell 106, this material being able to solidify after a predetermined delay following application.

Figure 31:
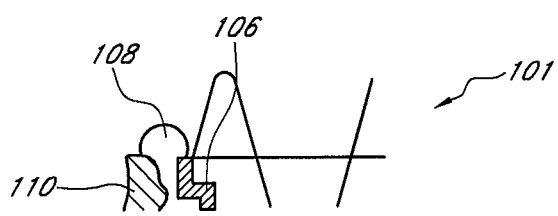
FIG. 31 is a schematic view of an alternative to the support of FIG. 29.

FIG. 31 shows support 101 whose shell 106 has a cross section in the form of a broken line, delimiting, on the exterior radial side, a lower shoulder. Housed in the step formed by this shoulder and the adjacent circumferential wall is peripheral shell 108 which can be inflated by means of a catheter (not represented). This shell 108 delimits a chamber and has a radially expandable structure, such that it has in cross section, in the inflated state, two widened ends projecting on both sides of shell 106. This chamber can receive an inflating fluid that can solidify in a predetermined delay following its introduction into said chamber. Once this material has solidified, the inflating catheter is cut off.

Figure 32:
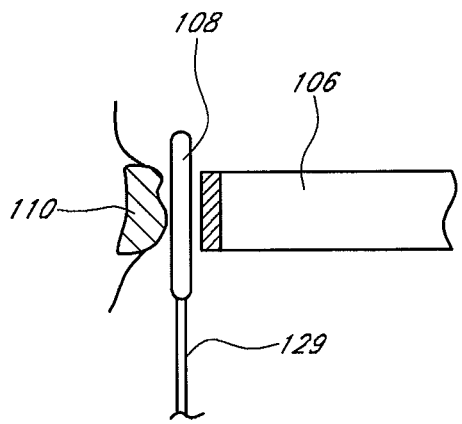
FIGS. 32 and 33 are schematic views of an alternative to the support of FIG. 29.
Figure 33:
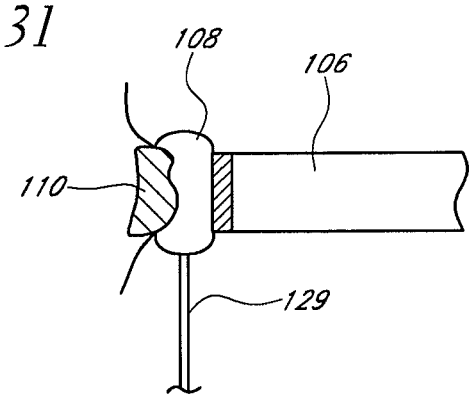

FIGS. 32 and 33 show support 101 whose shell 106 receives inflatable insert 108 which has a spool-shaped cross section in the inflated state; this insert 108 can be inflated by means of catheter 129. Insert 108 is positioned in the uninflated state (FIG. 32) at the sites in which a space exists between shell 106 and existing cardiac ring 110. Its spool shape allows this insert (cf. FIG. 33) to conform as much as possible to the adjacent irregular structures and to ensure a better seal.

Figure 21:
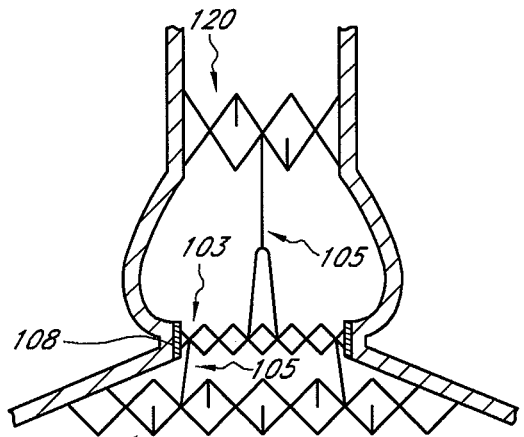
FIG. 21 is a schematic view of the support of FIG. 19 shown in a deployed state.
Figure 34:
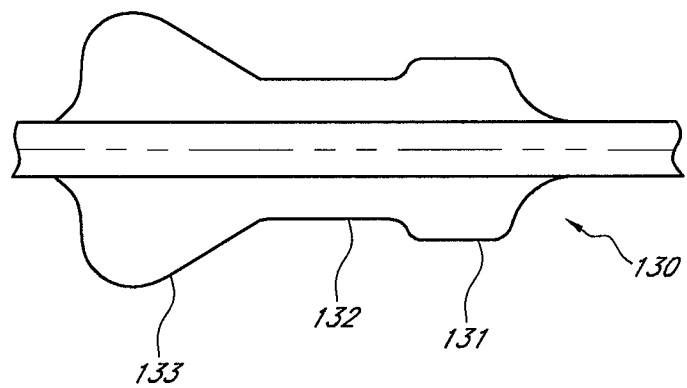
FIG. 34 is a schematic cross-sectional view of a balloon corresponding to the support structure of FIGS. 19 to 21.
Figure 35:
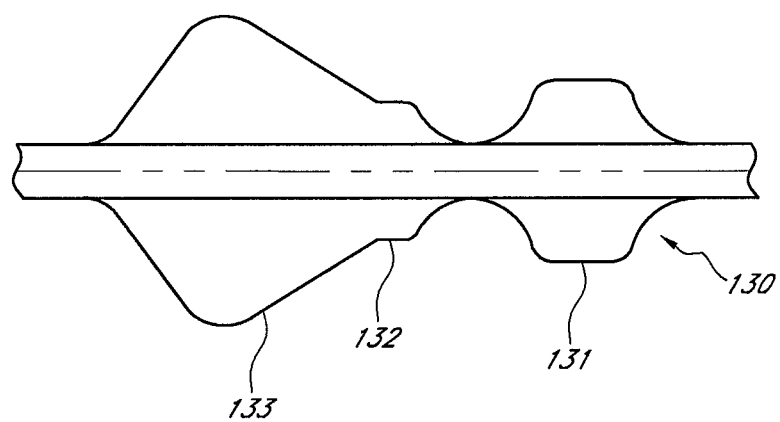
FIG. 35 is a schematic longitudinal sectional view of an alternative embodiment of the balloon of FIG. 34.

FIG. 34 shows balloon 130 making it possible to deploy support 101 according to FIGS. 19 to 21. This balloon 130 has cylindrical portion 131 whose diameter in the inflated state makes possible the expansion of holding portion 120, a cylindrical portion 132 of lesser diameter, suitable for producing the expansion of portion 103, and portion 133 in the form of a truncated cone, makes possible the expansion of portion 104. As shown by FIG. 35, portion 132 can be limited to what is strictly necessary for deploying portion 103, which makes it possible to produce balloon 130 in two parts instead of a single part, thus limiting the volume of this balloon 130.

Figure 36:
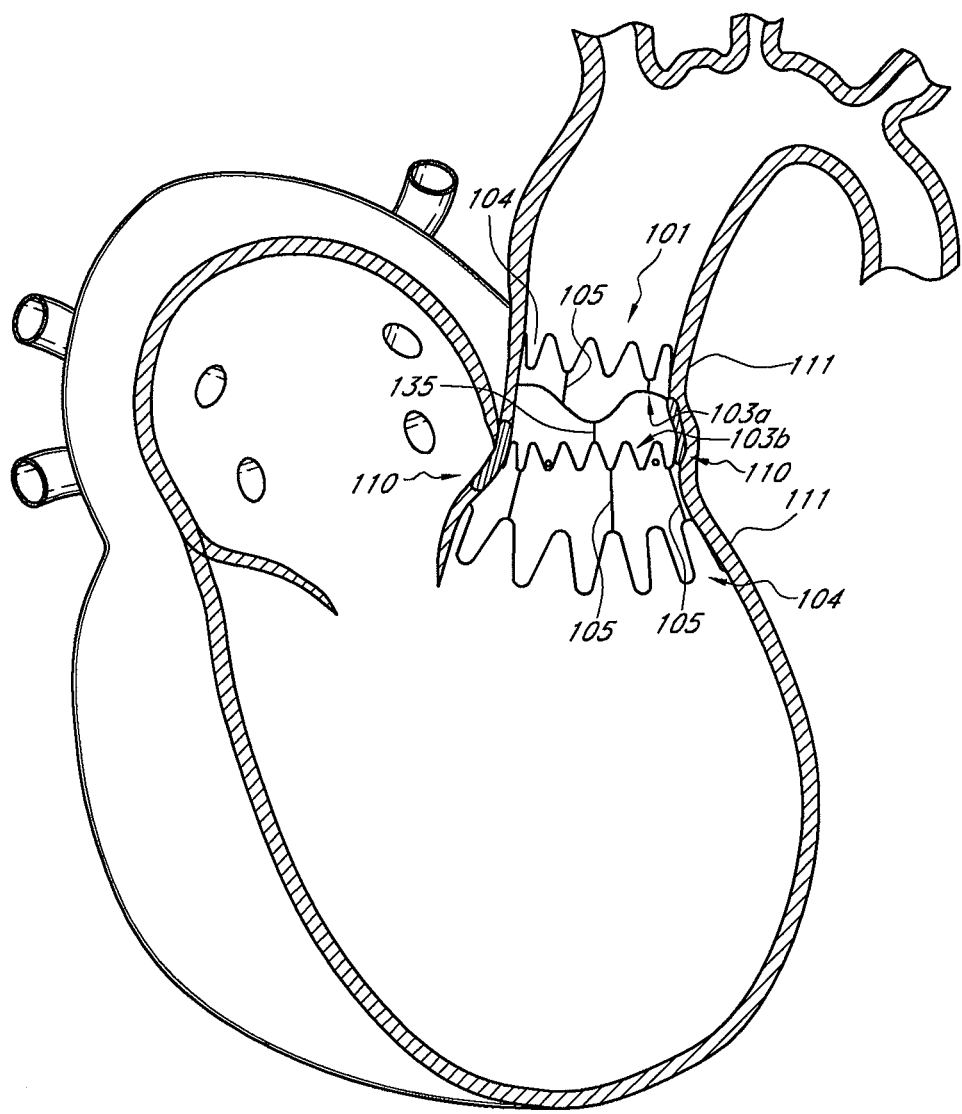
FIG. 36 is a schematic view of a heart with an embodiment of the present inventive prosthesis shown deployed in place.

FIG. 36 shows support 101 whose median portion 103 is in two parts 103a, 103b. Part 103a is made of undulating wire with large-amplitude undulations, in order to support valve 102, and part 103b, adjacent to said part 103a and connected to it by bridges 135, is made of undulating wire with small-amplitude undulations. Due to its structure, this part 103b presents a relatively high radial force of expansion and is intended to be placed opposite ring 110 in order to push back the native valve sheets which are naturally calcified, thickened and indurated, or the residues of the valve sheets after valve resection against or into the wall of the passage. This axial portion 103a, 103b thus eliminates the problem induced by these sheets or residual sheets at the time of positioning of valve 102.

It is apparent from the preceding that one embodiment of the invention provides a tubular support for positioning, by percutaneous route, of a replacement heart valve, which provides, due to its portions 103 and 104, complete certitude as to its maintenance of position after implantation. This support also makes possible a complete sealing of the replacement valve, even in case of a cardiac ring with a surface that is to varying degrees irregular and/or calcified, and its position can be adapted and/or corrected as necessary at the time of implantation.

Figure 37:
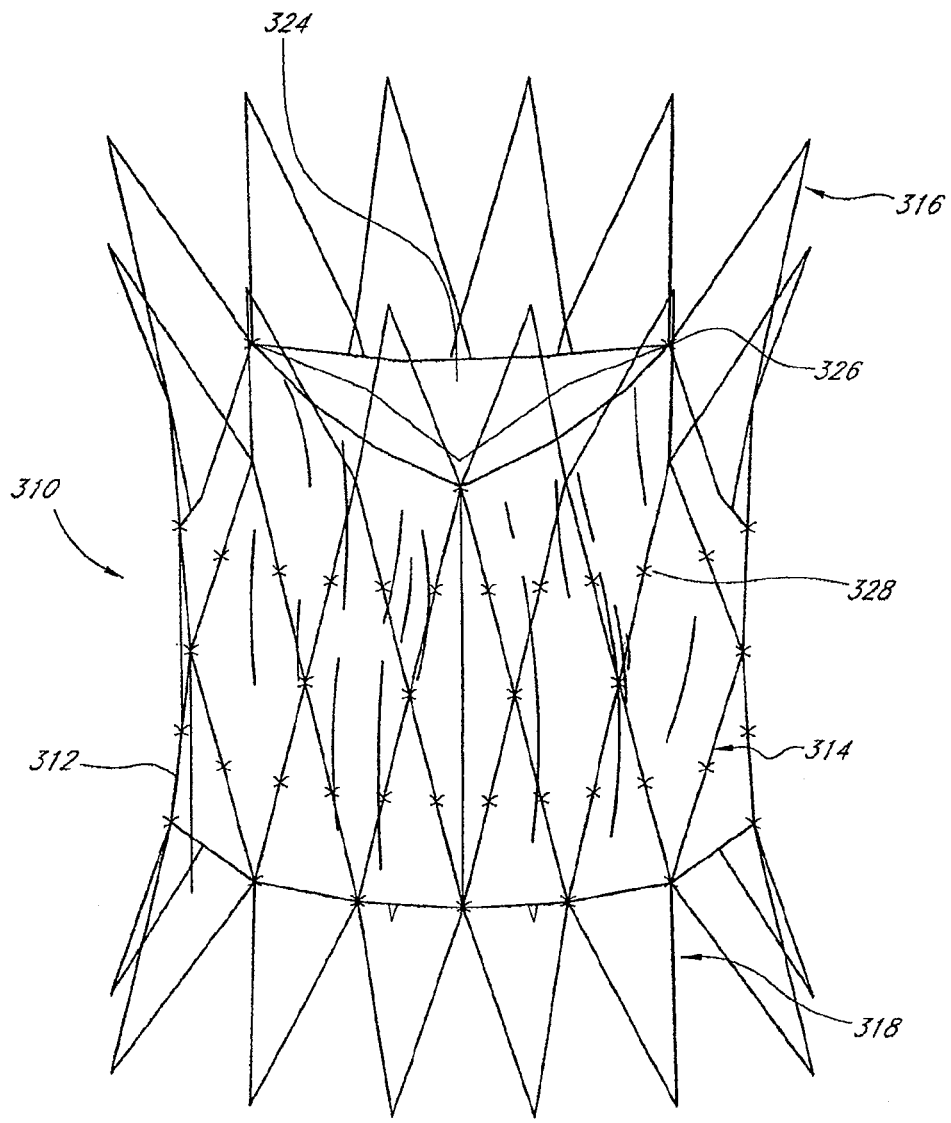
FIG. 37 is a perspective view of one embodiment of a prosthetic valve assembly of the present invention.
Figure 38:
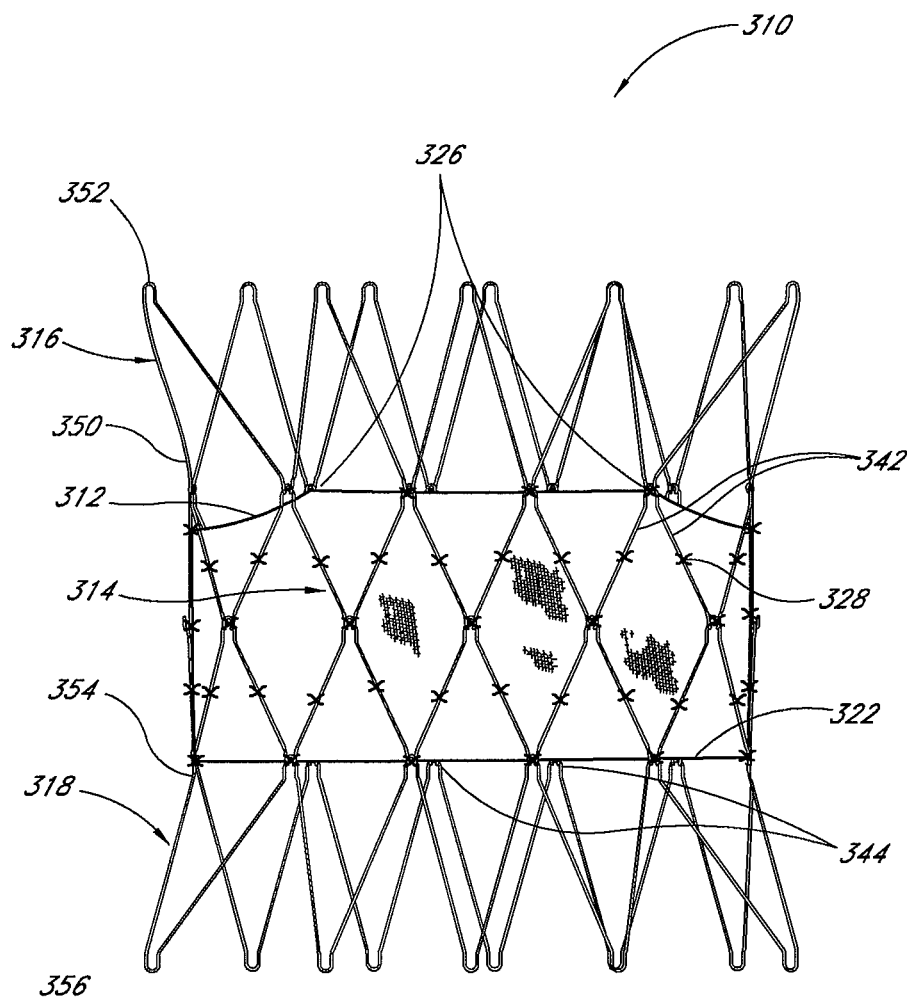
FIG. 38 is a side view of the prosthetic valve assembly of FIG. 37.

Referring to FIGS. 37 and 38, the present invention also comprises an alternative prosthetic valve assembly 310, which further comprises a prosthetic valve 312, a valve support band 314, distal anchor 316, and a proximal anchor 318. Valve 312 can be made from a biological material, such as one originating from an animal or human, or from a synthetic material, such as a polymer. Depending upon the native valve to be replaced, the prosthetic valve 312 comprises an annulus 322, a plurality of leaflets 324 and a plurality of commissure points 326. The leaflets 324 permit the flow of blood through the valve 312 in only one direction. In the preferred embodiment, the valve annulus 322 and the commissure points 326 are all entirely supported within the central support band 314. Valve 312 is attached to the valve support band 314 with a plurality of sutures 328, which can be a biologically compatible thread. The valve could also be supported on band 314 with adhesive, such as cyanoacrylate.

Figure 40:
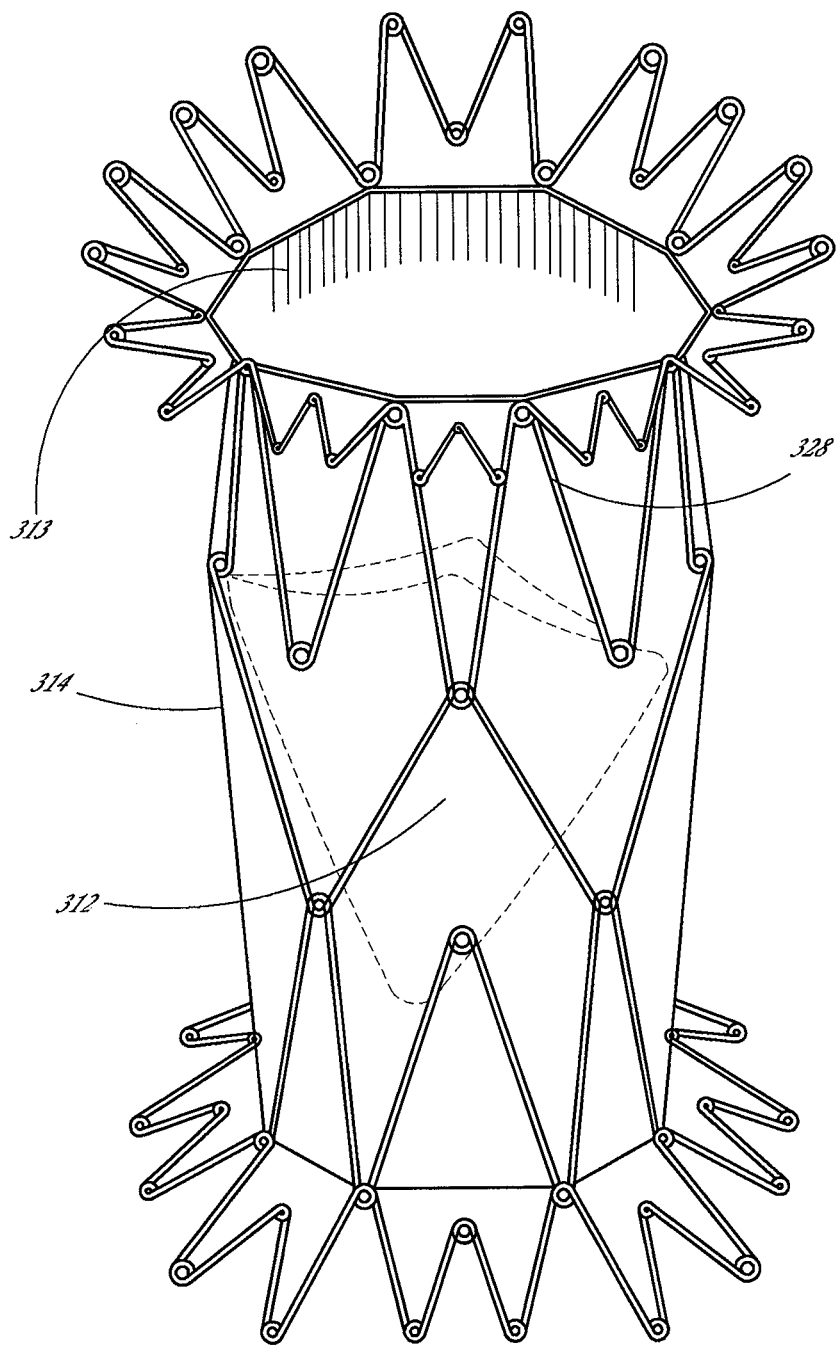
FIG. 40 is a perspective view of an alternative embodiment of the prosthetic valve assembly with a sheath around the valve.

In one embodiment, valve 312 can be attached to, or may integral with, a sleeve or sheath 313. The sheath is secured to the valve support band 314 such that the outer surface of the sheath is substantially in contact with the inner surface of the valve support band 314. In such embodiment, the sheath can be attached to the valve support band 314 with sutures 328. FIG. 40 is a schematic of the concept of this alternative embodiment. If desired, the sheath 313 can be secured to the outside of valve support band 314 (not shown).

Referring to FIGS. 37 and 38, in one embodiment, valve support band 314 is made from a single wire 342 configured in a zigzag manner to form a cylinder. Alternatively, valve support band 314 can be made from a plurality of wires 342 attached to one another. In either case, the band may comprise one or more tiers, each of which may comprise one or more wires arranged in a zigzag manner, for structural stability or manufacturing ease, or as anatomical constraints may dictate. If desired, even where the central valve support 314 is manufactured having more than one tier, the entire valve support 314 may comprise a single wire. Wire 342 can be made from, for example, stainless steel, silver, tantalum, gold, titanium or any suitable plastic material. Valve support band 314 may comprise a plurality of loops 344 at opposing ends to permit attachment to valve support band 314 of anchors 316 and/or 318 with a link. Loops 344 can be formed by twisting or bending the wire 342 into a circular shape. Alternatively, valve support band 314 and loops 344 can be formed from a single wire 342 bent in a zigzag manner, and twisted or bent into a circular shape at each bend. The links can be made from, for example, stainless steel, silver, tantalum, gold, titanium, any suitable plastic material, solder, thread, or suture. The ends of wire 342 can be joined together by any suitable method, including welding, gluing or crimping.

Still referring to FIGS. 37 and 38, in one embodiment, distal anchor 316 and proximal anchor 318 each comprise a discrete expandable band made from one or more wires 342 bent in a zigzag manner similar to the central band. Distal anchor band 316 and proximal anchor band 318 may comprise a plurality of loops 344 located at an end of wire 342 so that distal anchor band 316 and proximal anchor band 318 can each be attached to valve support band 314 with a link. Loop 344 can be formed by twisting or bending the wire 342 into a circular shape. As desired, distal and/or proximal anchors 316, 318 may comprise one or more tiers, as explained before with the valve support 314. Likewise, each anchor may comprise one or more wires, regardless of the number of tiers. As explained above in regard to other embodiments, the distal anchor may be attached to the central valve support band 314 directly, as in FIG. 37, or spaced distally from the distal end of the valve support 314, as shown above schematically in FIGS. 18, 19, 21 and 22. In the later instance, one or more struts may be used to link the distal anchor band to the valve support band, as described above.

Distal anchor band 316 has a first end 350 attached to the central valve band 314, and a second end 352. Similarly, proximal anchor band 318 has first attached end 354 and a second end 356. The unattached ends 352, 356 of the anchors 316, 318, respectively are free to expand in a flared manner to conform to the local anatomy. In such embodiment, the distal and proximal anchor bands 316, 318 are configured to exert sufficient radial force against the inside wall of a vessel in which it can be inserted. Applying such radial forces provides mechanical fixation of the prosthetic valve assembly 310, reducing migration of the prosthetic valve assembly 310 once deployed. It is contemplated, however, that the radial forces exerted by the valve support 314 may be sufficient to resist more than a minimal amount of migration, thus avoiding the need for any type of anchor.

In an alternative embodiment, distal and proximal anchors may comprise a fixation device, including barbs, hooks, or pins (not shown). Such devices may alternatively or in addition be placed on the valve support 314. If so desired, the prosthetic valve assembly 310 may comprise an adhesive on the exterior thereof to adhere to the internal anatomical lumen.

Figure 39:
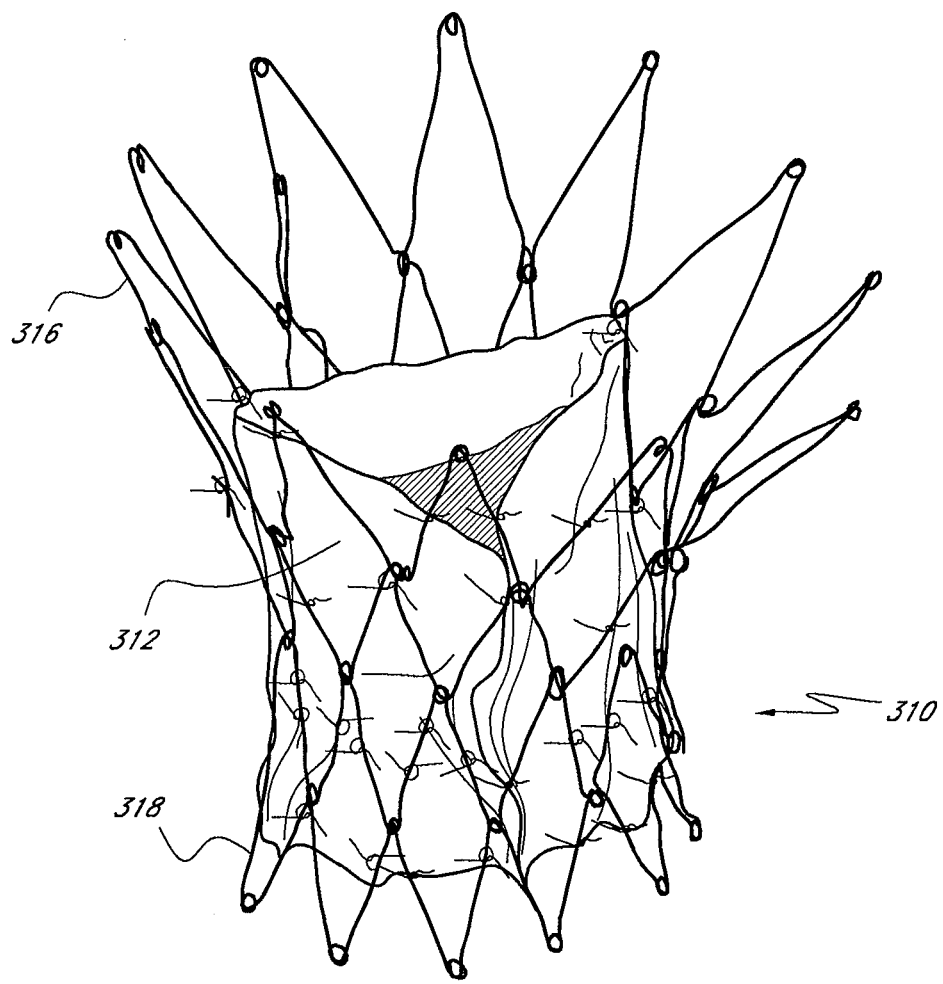
FIG. 39 is a perspective view of one embodiment of the prosthetic valve assembly of FIG. 37.
Figure 49:
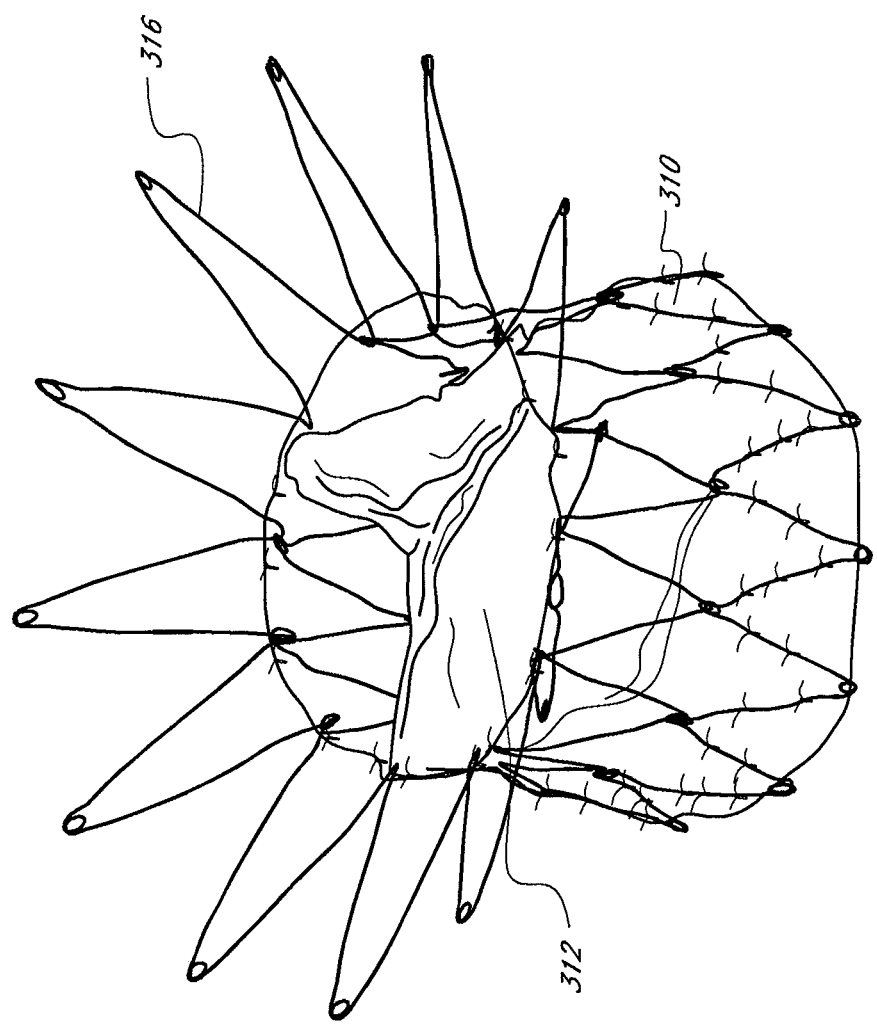
FIG. 49 is a perspective view of an alternative embodiment of the prosthetic valve assembly of FIG. 37 showing a distal anchor.

Prosthetic valve assembly 310 is compressible about its center axis such that its diameter may be decreased from an expanded position to a compressed position. When placed into the compressed position, valve assembly 310 may be loaded onto a catheter and transluminally delivered to a desired location within a body, such as a blood vessel, or a defective, native heart valve. Once properly positioned within the body the valve assembly 310 can be deployed from the compressed position to the expanded position. FIG. 39 is a schematic of one embodiment of the prosthetic valve assembly described with both distal and proximal anchor bands 316, 318 while FIG. 49 is a schematic showing only a distal anchor 316.

In the preferred embodiment, the prosthetic valve assembly 310 is made of self-expanding material, such as Nitinol. In an alternative embodiment, the valve assembly 310 requires active expansion to deploy it into place. Active expansion may be provided by an expansion device such as a balloon.

Figures 41A, 41B:
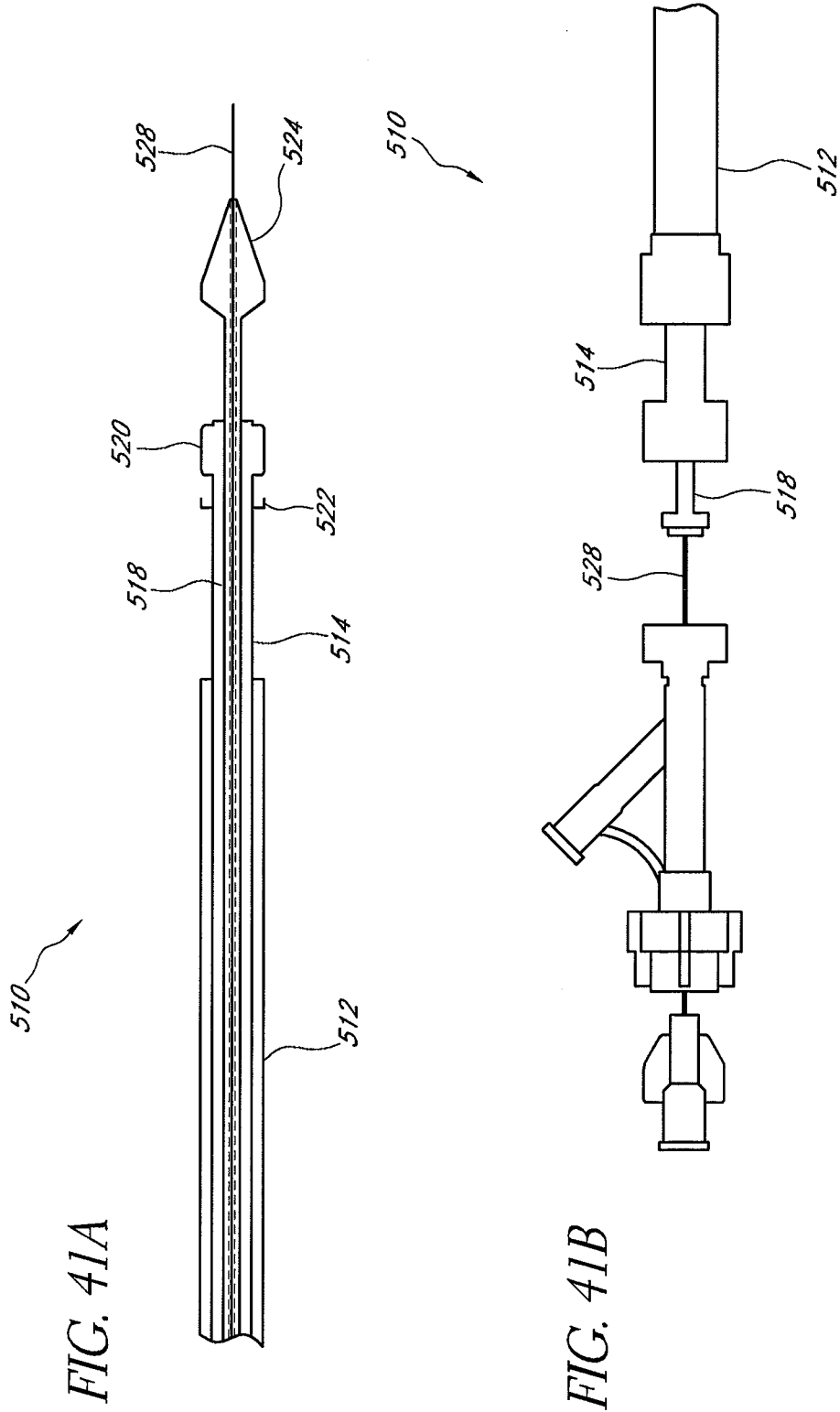
FIG. 41A is a perspective view of a distal portion of a catheter assembly for use in deploying the prosthetic valve assembly described herein.
FIG. 41B is a perspective view of a proximal portion of the catheter assembly of FIG. 41A.
Figure 42:
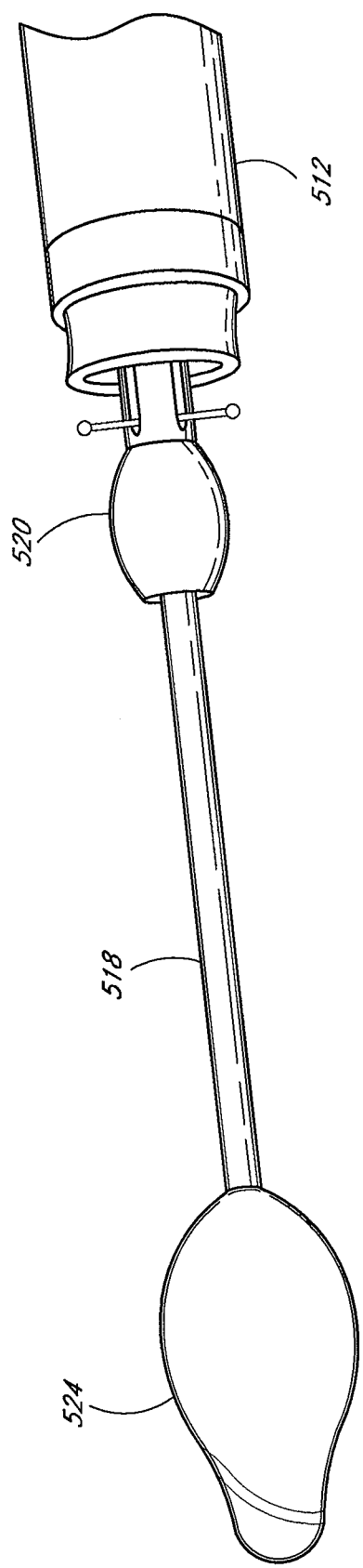
FIG. 42 is a perspective view of the distal portion of the catheter assembly of FIG. 41A.
Figure 43:
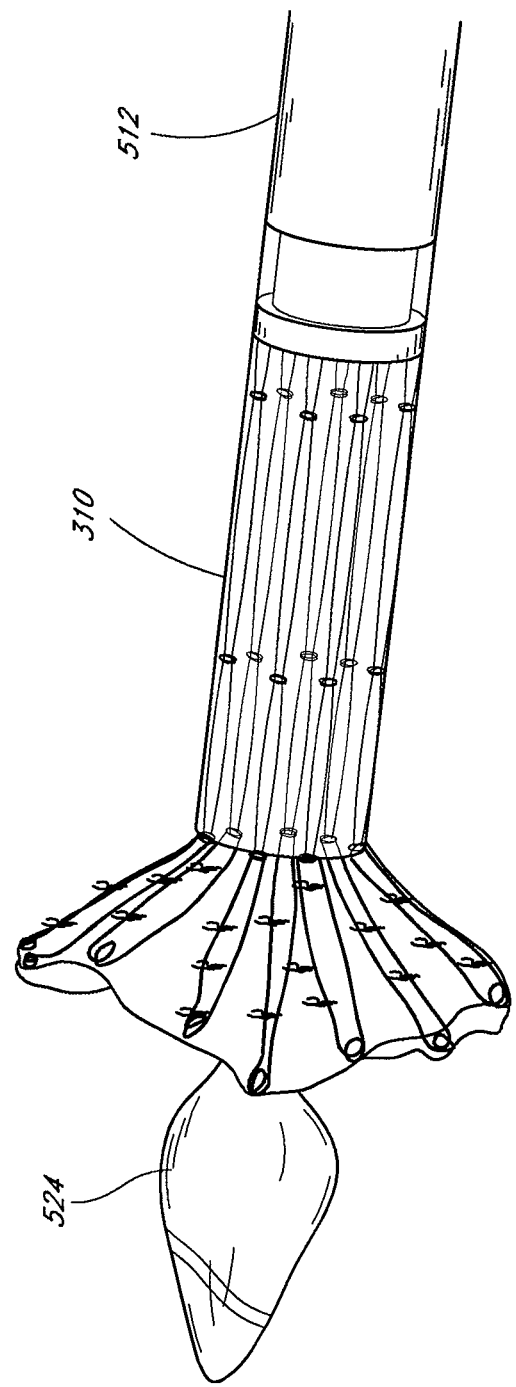
FIGS. 43 through 45 are perspective views of the catheter assembly of FIG. 41A showing deployment of a prosthesis assembly in sequence.
Figure 44:
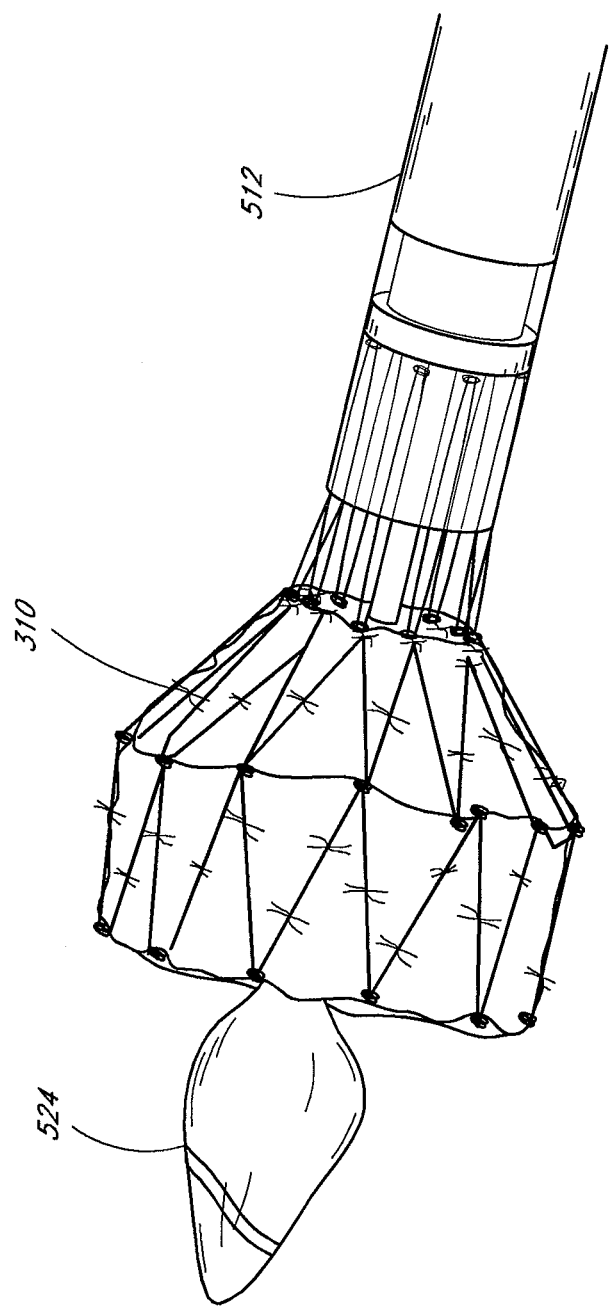
Figure 45:
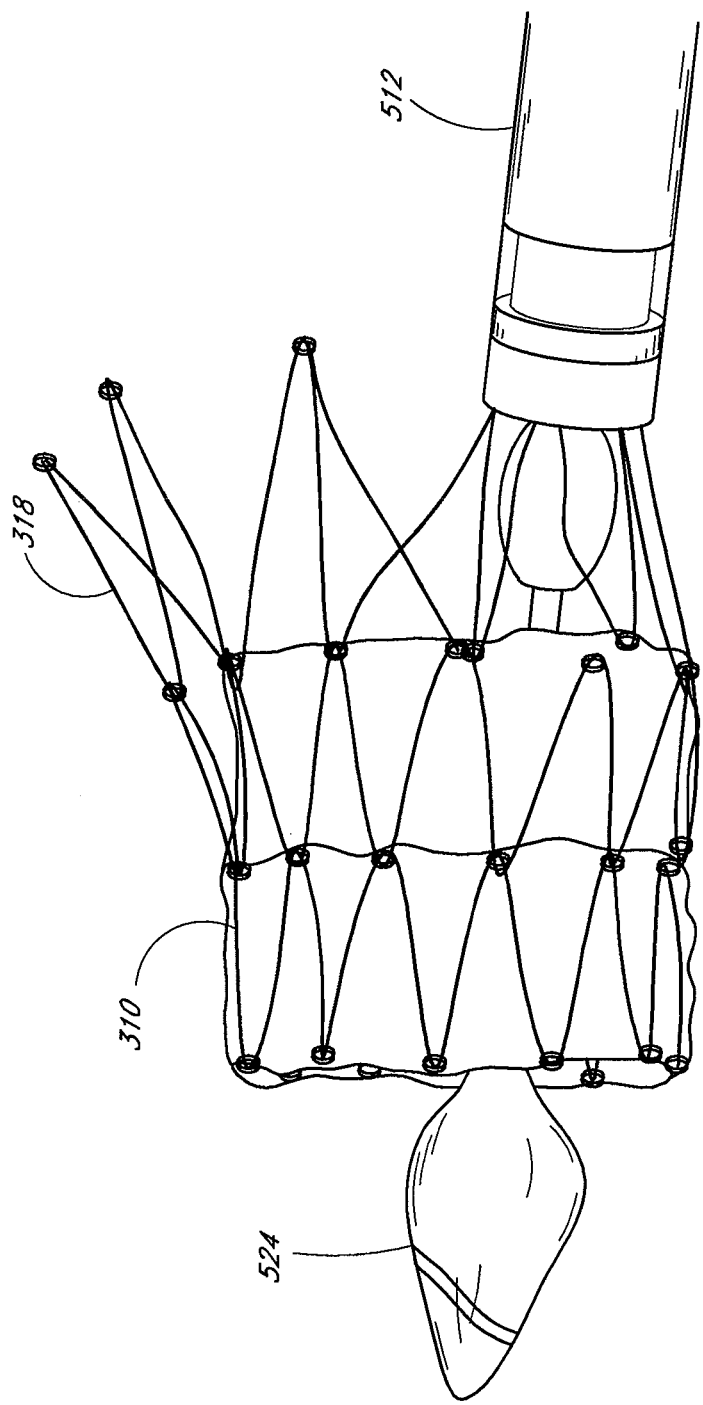

As referred to above in association with other embodiments, the prosthetic valve assembly of the present invention is intended to be percutaneously inserted and deployed using a catheter assembly. Referring to FIG. 41A, the catheter assembly 510 comprises an outer sheath 512, an elongate pusher tube 514, and a central tube 518, each of which are concentrically aligned and permit relative movement with respect to each other. At a distal end of the pusher tube 514 is a pusher tip 520 and one or more deployment hooks 522 for retaining the prosthesis assembly (not shown). The pusher tip 520 is sufficiently large so that a contracted prosthesis assembly engages the pusher tip 520 in a frictional fit arrangement. Advancement of the pusher tube 514 (within the outer sheath 512) in a distal direction serves to advance the prosthesis relative to the outer sheath 512 for deployment purposes.

At a distal end of the central tube 518 is an atraumatic tip 524 for facilitating the advancement of the catheter assembly 510 through the patient's skin and vasculature. The central tube 518 comprises a central lumen (shown in phantom) that can accommodate a guide wire 528. In one embodiment, the central lumen is sufficiently large to accommodate a guide wire 528 that is 0.038 inch in diameter. The guide wire can slide through the total length of the catheter form tip to handle ('over the wire' catheter) or the outer sheath 512 can be conformed so as to allow for the guide wire to leave the catheter before reaching its proximal end ('rapid exchange' catheter). The space between the pusher tube 514 and the outer sheath 512 forms a space within which a prosthetic valve assembly may be mounted.

Hooks 522 on the distal end of the pusher tube 514 may be configured in any desired arrangement, depending upon the specific features of the prosthetic assembly. With regard to the prosthesis assembly of FIGS. 37 and 38, the hooks 522 preferably comprise an L-shaped arrangement to retain the prosthesis assembly axially, but not radially. With a self-expanding assembly, as the prosthesis assembly is advanced distally beyond the distal end of the outer sheath 512, the exposed portions of the prosthesis assembly expand while the hooks 522 still retain the portion of the prosthesis still housed within the outer sheath 512. When the entire prosthesis assembly is advanced beyond the distal end of the outer sheath, the entire prosthesis assembly is permitted to expand, releasing the assembly from the hooks. FIGS. 42 through 45 show the distal end of one embodiment of the catheter assembly, three of which show sequenced deployment of a valve prosthesis.

Figure 46:
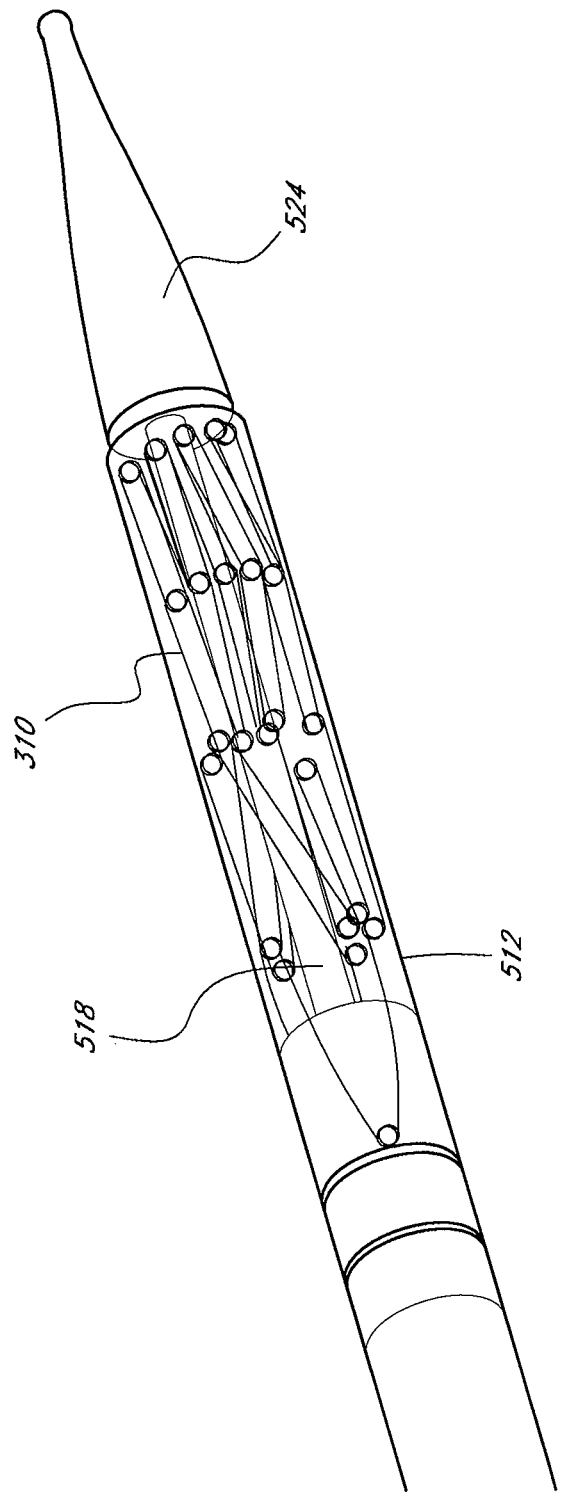
FIGS. 46 and 47 are perspective views of the catheter assembly of FIG. 41A showing deployment of an alternative prosthesis assembly.
Figure 47:
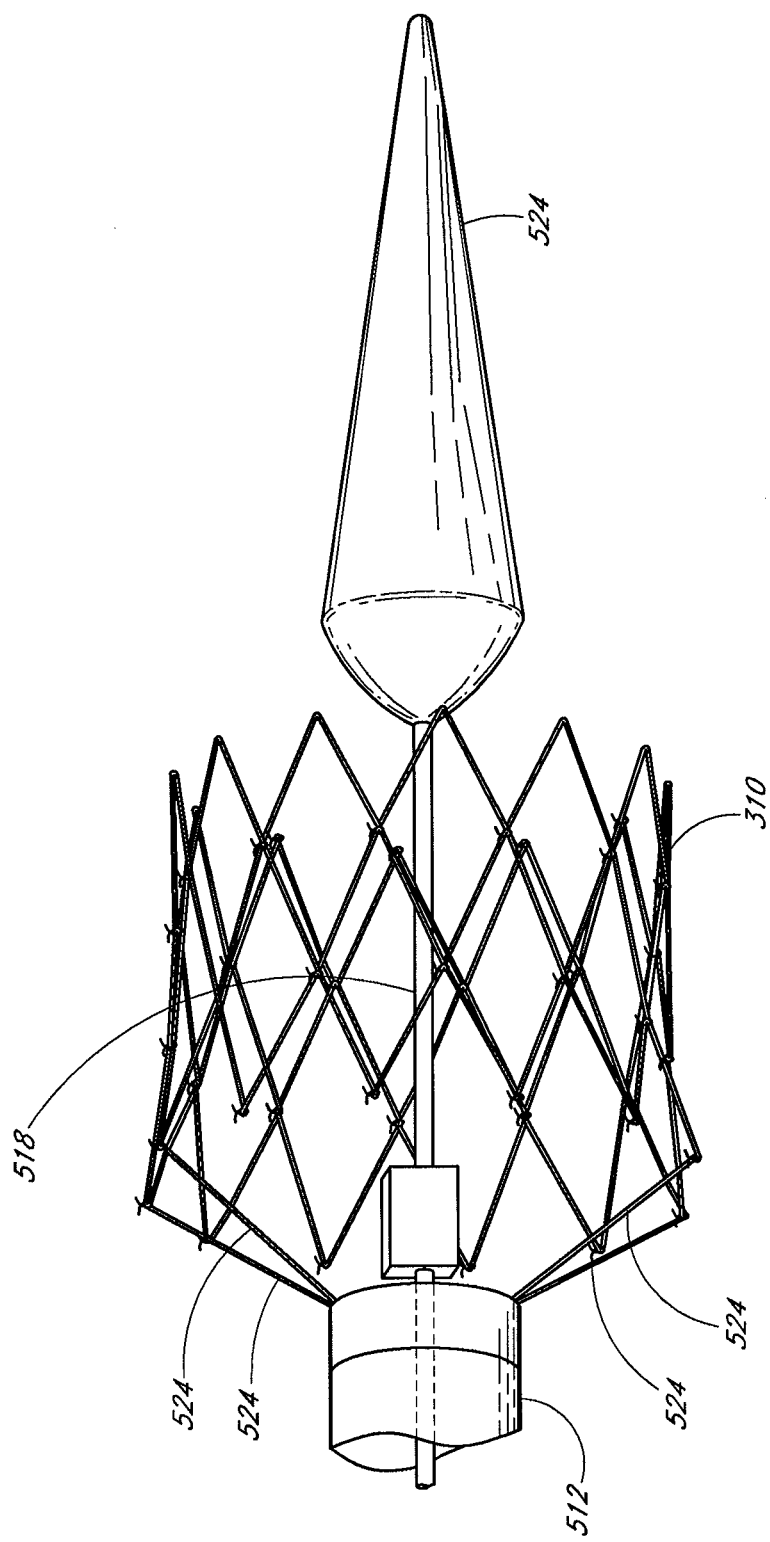
Figure 48:
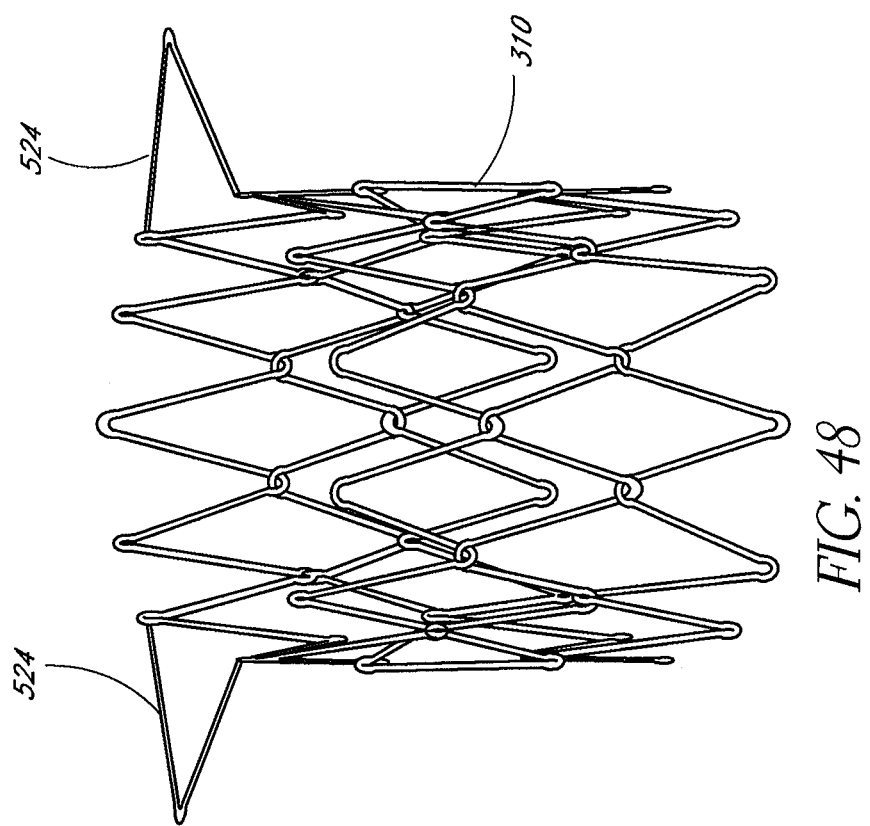
FIG. 48 is a perspective view of the alternative prosthesis assembly shown in FIGS. 46 and 47.

FIG. 48 shows an alternative embodiment of the valve prosthesis, where loop elements extend axially from one end of the prosthesis and are retained by the hooks 522 on pusher tube 514 during deployment. FIGS. 46 and 47 show a catheter assembly used for deploying the alternative prosthesis assembly of FIG. 48. By adding loop elements to the prosthesis, the prosthesis may be positioned with its support and anchors fully expanded in place while permitting axial adjustment into final placement before releasing the prosthesis entirely from the catheter. Referring to FIG. 55, an alternative embodiment of a self-expanding valve prosthesis and delivery system comprises loop elements 694 on prosthetic assembly 310 retained by disks 696 on pusher tube 514 by outer sheath 512. When outer sheath 512 is pulled back to expose disks 696, self-expanding loop elements 694 are then released from pusher tube 514.

FIG. 41B shows the proximal end of the catheter assembly 510 that, to a greater extent, has many conventional features. At the distal end of the pusher tube 514 is a plunger 530 for advancing and retreating the pusher tube 514 as deployment of the prosthesis assembly is desired. As desired, valves and flush ports proximal and distal to the valve prosthesis may be provided to permit effective and safe utilization of the catheter assembly 510 to deploy a prosthesis assembly.

In one embodiment, prosthetic valve assembly 310 (not shown) is mounted onto catheter 510 so that the valve assembly 310 may be delivered to a desired location inside of a body. In such embodiment, prosthetic valve assembly 310 is placed around pusher tip 520 and compressed radially around the tip 520. The distal end of prosthetic valve assembly 310 is positioned on the hooks 522. While in the compressed position, outer sheath 512 is slid toward the atraumatic tip 524 until it substantially covers prosthetic valve assembly 310.

To deliver prosthetic valve assembly 310 to a desired location within the body, a guide wire 528 is inserted into a suitable lumen of the body, such as the femoral artery or vein to the right atrium, then to the left atrium through a transseptal approach, and maneuvered, utilizing conventional techniques, until the distal end of the guide wire 528 reaches the desired location. The catheter assembly 510 is inserted into the body over the guide wire 528 to the desired position. Atraumatic tip 524 facilitates advancement of the catheter assembly 510 into the body. Once the desired location is reached, the outer sheath 512 is retracted permitting the valve prosthesis to be released from within the outer sheath 512, and expand to conform to the anatomy. In this partially released state, the position of prosthetic valve 310 may be axially adjusted by moving catheter assembly 510 in the proximal or distal direction.

It is apparent that the invention advantageously contemplates a prosthesis that may have a non-cylindrical shape, as shown in several earlier described embodiments including but not limited to FIGS. 21, 37-40, 49 and 59. This non-cylindrical shape results from controlling the diameters at some portions of prosthetic valve assembly 310. Referring to FIG. 56A, yet another non-cylindrical prosthesis is shown. Central support band 314 comprises a diameter-restrained portion of valve assembly 310 attached to distal and proximal anchors 316, 318, that comprise discrete self-expandable bands capable of expanding to a flared or frusta-conical configuration. Anchors 316, 318 further accentuate the non-cylindrical shape of central support band 314. FIG. 56A shows one embodiment of the invention for limiting the diameter of portions of the valve assembly 310 from excessive expansion, whereby valve assembly 310 further comprises a radial restraint 690 to limit the diameter of central support band 314. Radial restraint, as used herein, shall mean any feature or process for providing a desired diameter or range of diameters, including but not limited to the selection of materials or configurations for valve assembly 310 such that it does not expand beyond a preset diameter. Controlling radial expansion to a preset diameter at central support band 314 helps maintain the coaptivity of valve 312 and also preserves the patency of the coronary ostia by preventing central support band 314 from fully expanding to the lumen or chamber wall to cause occlusion. Restraint 690 may be sufficiently flexible such that restraint 690 may contract radially with valve assembly 310, yet in the expanded state resists stretching beyond a set limit by the radial expansion forces exerted by a self-expanding valve assembly 310 or from a balloon catheter applied to valve assembly 310. Referring to FIGS. 56A and 56B, restraint 690 may take any of a variety of forms, including wires 700 of a specified length that join portions of central support band 314. Threads may also be used for radial restraint 690. The slack or bends in the wires allow a limited radial expansion to a maximum diameter. Once the slack is eliminated or the bends are straightened, further radial expansion is resisted by tension created in wires 700. These wires may be soldered, welded or interwoven to valve assembly 310. By changing the length of wire joining portions of valve assembly 310, radial restraints of different maximum diameters are created. For example, by using short wires to form the radial restraint, the valve support structure may expand a shorter distance before tension forms in the short wires. If longer wires are used, the support structure may expand farther before tension develops in the longer wires.

Figure 57:
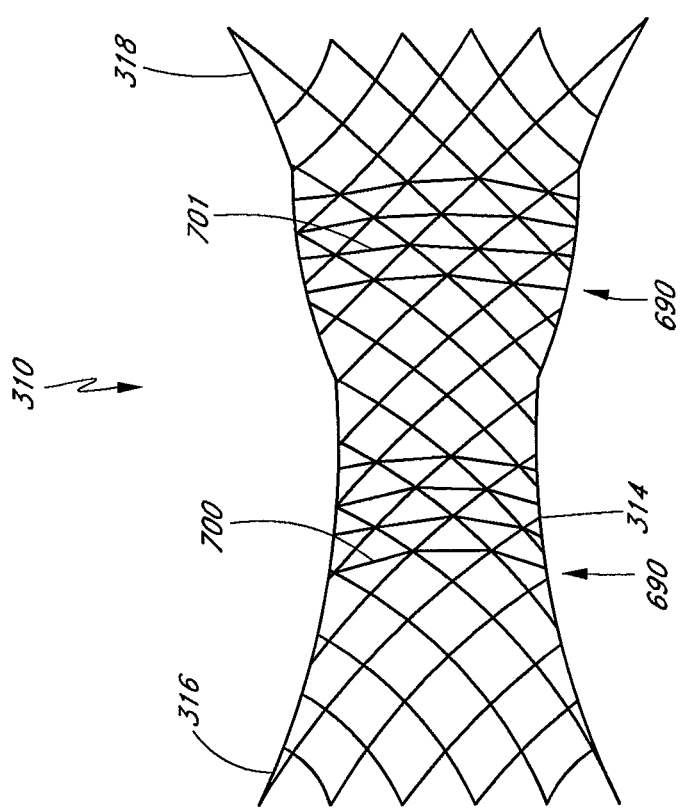
FIG. 57 depicts another embodiment of the invention wherein two radial restraints of different size are attached to different portions of the support structure.
Figure 58:
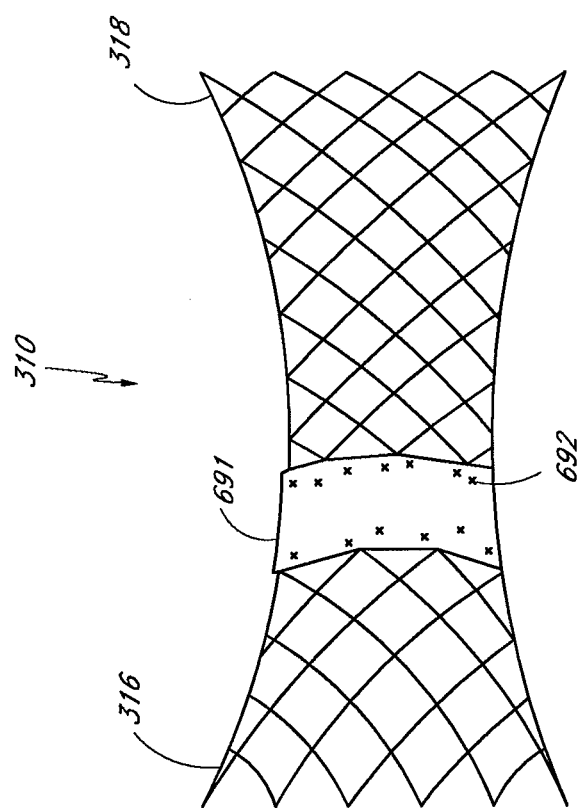
FIG. 58 represents one embodiment of the radial restraint comprising a cuff-type restraint.

FIG. 57 depicts central support band 314 with a radial restraint 700 of a smaller diameter and another portion of the same valve assembly 310 with longer lengths of wire 701 and allowing a larger maximum diameter. The portion of valve assembly 310 with the larger diameter can be advantageously used to allow greater dilation around cardiac ring 110 and native valve sheets. The degree of resistance to expansion or recollapse can be altered by changing the diameter of the radial restraint or by changing the configuration of the restraint. For example, a cross-linked radial restraint will have a greater resistance to both expansion and recollapse. Referring to FIG. 58, restraint 690 may alternatively comprise a cuff 691 encompassing a circumference of central support band 314 that resists expansion of central support band 314 beyond the circumference formed by cuff 691. Cuff 691 may be made of ePTFE or any other biocompatible and flexible polymer or material as is known to those skilled in the art. Cuff 691 may be attached to valve assembly 310 by sutures 692 or adhesives.

Figure 71:
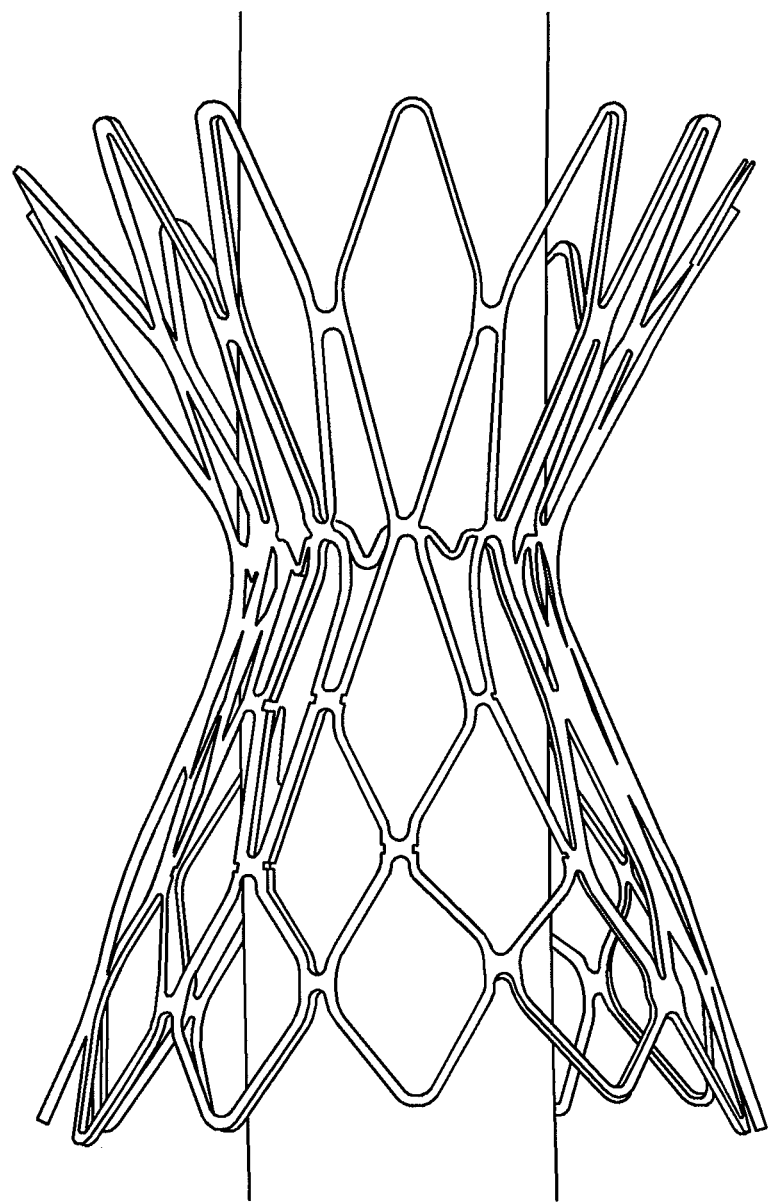
FIG. 71 is a photograph of a valve assembly with radial restraints integrally formed by laser cutting.
Figure 72A:
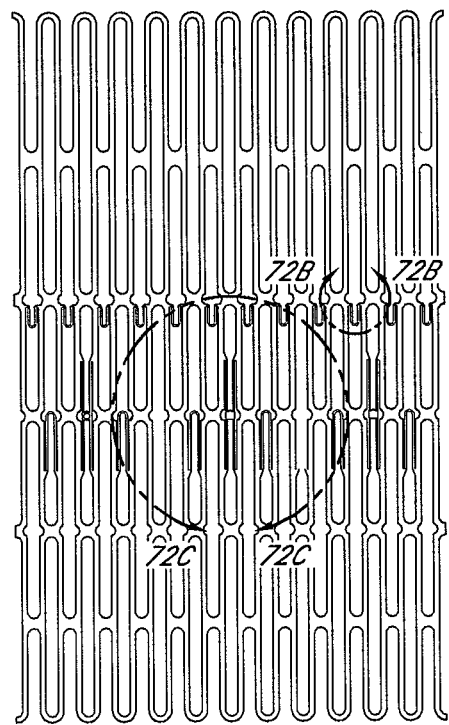
FIGS. 72A through 72C are schematic views of a portion of a valve assembly with different radial restraints formed by laser cutting.
Figure 72B:
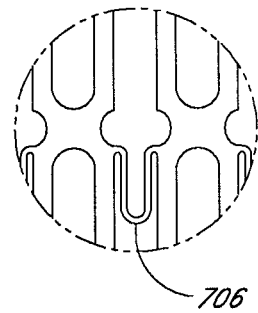
Figure 72C:
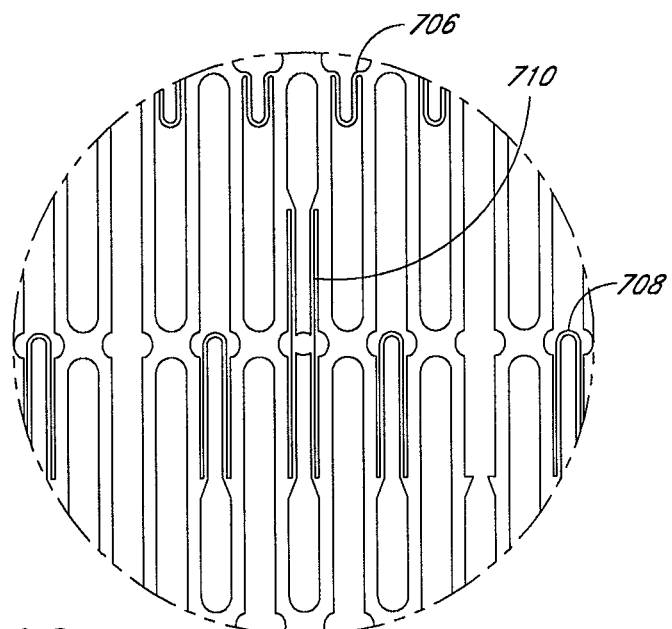

FIG. 71 illustrates one embodiment of the invention where radial restraints are integrally formed as part of valve assembly 310 by using a laser cutting manufacturing process, herein incorporated by reference. FIG. 72A depicts a schematic view of a laser-cut portion of valve assembly 310 in the unexpanded state with several radial restraints 706, 708, 710. Each end of radial restraints 706, 708, 710 is integrally formed and attached to valve assembly 310. An integrally formed radial restraint may be stronger and may have a lower failure rate compared to radial restraints that are sutured, welded or soldered to valve assembly 310. FIG. 72B depicts a shorter radial restraint 706 along one circumference of valve assembly 310. FIG. 72C depicts another portion of valve assembly 310 with a longer radial restraint 708 and a cross-linked radial restraint 710 positioned along the same circumference. Thus, the segments of a radial restraint along a given circumference need not have the same characteristics or size.

Figures 74A, 74B:
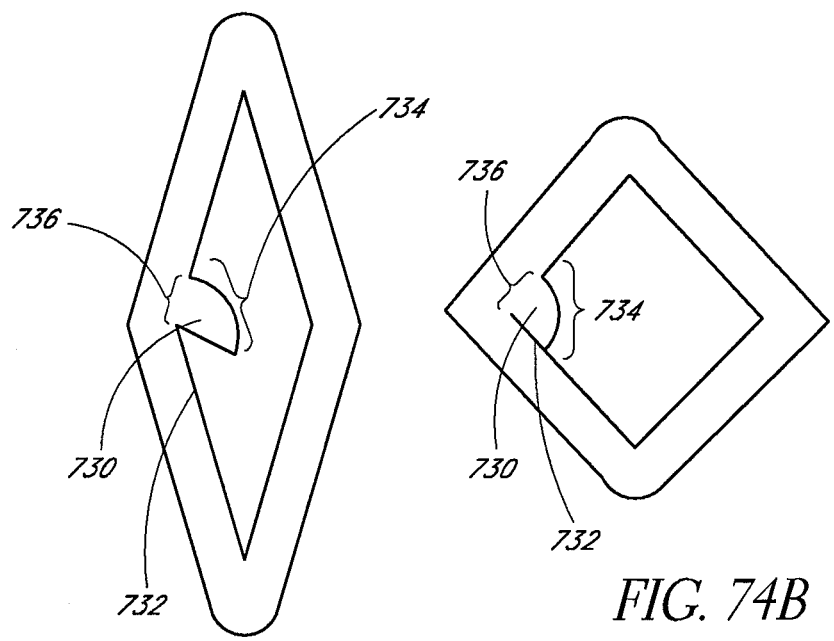
FIGS. 74A and 74B are schematic views of an angular mechanical stop for controlling diameter.

Another embodiment of the radial restraint comprises at least one protrusion extending from valve assembly 310 to provide a mechanical stop arrangement. The mechanical stop arrangement restricts radial expansion of valve assembly 310 by using the inverse relationship between the circumference of valve assembly 310 and the length of valve assembly 310. As valve assembly 310 radially expands, the longitudinal length of valve assembly 310 may contract or compress as the diameter of valve assembly 310 increases, depending upon the particular structure or configuration used for valve assembly 310. For example, FIGS. 37, 38, 56A, 57 and 71 depict embodiments of the invention wherein valve assembly 310 comprises a diamond-shaped mesh. The segments of the mesh have a generally longitudinal alignment that reorient to a more circumferential alignment during radial expansion of valve assembly 310. By limiting the distance to which valve assembly 310 can compress in a longitudinal direction, or by restricting the amount of angular reorientation of the wires of valve assembly 310, radial expansion in turn may be controlled to a pre-set diameter. FIG. 74A shows one embodiment of the mechanical stop arrangement comprising an angular stop 730 and an abutting surface 732 on the wire structure of valve assembly 310. A plurality of stops 730 and abutting surfaces 732 may be used along a circumference of valve assembly 310 to limit expansion to a preset diameter. Angular stop 730 may be located between two adjoining portions of valve assembly 310 forming an angle that reduces with radial expansion. As shown in FIG. 74B, as valve assembly 310 radially expands, angular stop 730 will come in closer proximity to surface 732 and eventually abut against surface 732 to prevent further diameter expansion of valve assembly 310. The angular size 734 of stop 730 can be changed to provide different expansion limits. The radial size 736 of stop 730 can also be changed to alter the strength of stop 730. One skilled in the art will understand that many other configurations may be used for valve assembly 310 besides a diamond-shape configuration. For example, FIGS. 15 and 16 depict support 101 with an undulating wire stent configuration that exhibits minimal longitudinal shortening when expanding. The mechanical stop arrangements described above may be adapted by those skilled in the art to the undulating wire stent configuration, or any other stent configuration, for controlling the diameter of the support structure or valve assembly 310.

The particular method of maintaining the valve diameter within a preset range described previously relates to the general concept of controlling the expanded diameter of the prosthesis. The diameter attained by a portion of the prosthesis is a function of the radial inward forces and the radial expansion forces acting upon that portion of the prosthesis. A portion of the prosthesis will reach its final diameter when the net sum of these forces is equal to zero. Thus, controlling the diameter of the prosthesis can be addressed by changing the radial expansion force, changing the radial inward forces, or a combination of both. Changes to the radial expansion force generally occur in a diameter-related manner and can occur extrinsically or intrinsically. Radial restraint 690, cuff 691 and mechanical stop 730 of FIGS. 56A, 58 and 74A, respectively, are examples of extrinsic radial restraints that can limit or resist diameter changes of prosthetic valve assembly 310 once a preset diameter is reached.

Other ways to control diameter may act intrinsically by controlling the expansion force so that it does not expand beyond a preset diameter. This can be achieved by the use of the shape memory effect of certain metal alloys like Nitinol. As previously mentioned, when a Nitinol prosthesis is exposed to body heat, it will expand from a compressed diameter to its original diameter. As the Nitinol prosthesis expands, it will exert a radial expansion force that decreases as the prosthesis expands closer to its original diameter, reaching a zero radial expansion force when its original diameter is reached. Thus, use of a shape memory alloy such as Nitinol is one way to provide an intrinsic radial restraint. A non-shape memory material that is elastically deformed during compression will exhibit similar diameter-dependent expansion forces when returning to its original shape.

The other way of controlling diameter mentioned previously is to alter the radial inward or recoil forces acting upon the support or prosthesis. Recoil forces refer to any radially inward force acting upon the valve assembly that prevents the valve support from maintaining a desired expanded diameter. Recoil forces include but are not limited to radially inward forces exerted by the surrounding tissue and forces caused by elastic deformation of prosthetic valve assembly 310. Countering or reducing recoil forces help to ensure deployment of prosthetic valve assembly 310 to the desired diameter or diameter range, particularly at the native valve. For example, when the prosthetic valve assembly 310 of FIGS. 37, 38, 56A, 57 and 58 is deployed, some recoil or diameter reduction may occur that can prevent portions of valve assembly 310 from achieving it pre-set or desired diameter. This recoil can be reduced by applying an expansion force, such as with a balloon, that stresses the material of valve assembly 310 beyond its yield point to cause plastic or permanent deformation, rather than elastic or transient deformation. Similarly, balloon expansion can be used to further expand a self-expanded portion of valve assembly 310 where radially inward anatomical forces have reduced the desired diameter of that portion. Balloon expansion of a self-expanded portion of valve assembly 310 beyond its yield point provides plastic deformation to a larger diameter.

In addition to the use of a balloon catheter to deform valve assembly 310 beyond its yield point, other means for reducing recoil are contemplated. In the preferred embodiment of the invention, a separate stent may be expanded against cardiac ring 110 in addition or in place of valve assembly 310. The separate stent may further push back the native valve sheets or residues of the resected valve and reduce the recoil force of these structures on valve assembly 310. If the separate stent is deployed against cardiac ring 110 prior to deployment of valve assembly 310, a higher radial force of expansion is exerted against ring 110 without adversely affecting the restrained radial force of expansion desired for the central support band 314 supporting valve 312. Alternatively, the separate stent may be deployed after valve assembly 310 and advantageously used to reduce the recoil of valve assembly 310 caused by the elastic deformation of the material used to form valve assembly 310. The separate stent may be self-expanding or balloon-expandable, or a combination thereof.

Another means for addressing recoil involves providing the radial restraint and mechanical stop arrangements previously described with an additional feature that forms an interference fit when the valve assembly 310 is at its preset diameter. By forming an interference fit, the radial restraint or mechanical stop will resist both further expansion and recollapse from recoil. FIGS. 73A through 73E depict an embodiment of a radial restraint with a recoil-resistant configuration integrally formed with valve assembly 310. In this embodiment, each segment of the radial restraint comprises a pair of protrusions 712 having a proximal end 714 and a distal end 716. Proximal end 714 is integrally formed and attached to valve assembly 310 while distal end 716 is unattached. Each pair of protrusions 712 is configured so that distal end 716 of one protrusion 712 is in proximity to the proximal end 714 of other protrusion 712 in the unexpanded state, and where distal ends 716 come close together as valve assembly 310 radially expands. Distal ends 716 comprise a plurality of teeth 718 for providing an interference fit between distal ends 716 upon contact with each other. The interference fit that is formed will resist both further radial expansion and collapse of valve assembly 310. As mentioned earlier, collapse may result from the inherent elastic properties of the materials used for valve assembly 310 or from radially inward forces exerted by the tissue surrounding valve assembly 310. The interference fit may be provided over a range of expansion, as depicted in FIGS. 72B and 72C from the self-expanded state through the extra-expanded state. This allows the inference fit to act even when a self-expanded valve assembly 310 is further expanded by a balloon catheter to an extra-expanded state as the expansion diameter is further adjusted. The lengths of protrusions 712 will determine the amount of radial restraint provided. Shorter protrusions 712 have distal ends 716 that contact each other after a shorter distance of radial expansion, while longer protrusions 712 will form an interference fit after a longer distance.

Figures 75A, 75B:
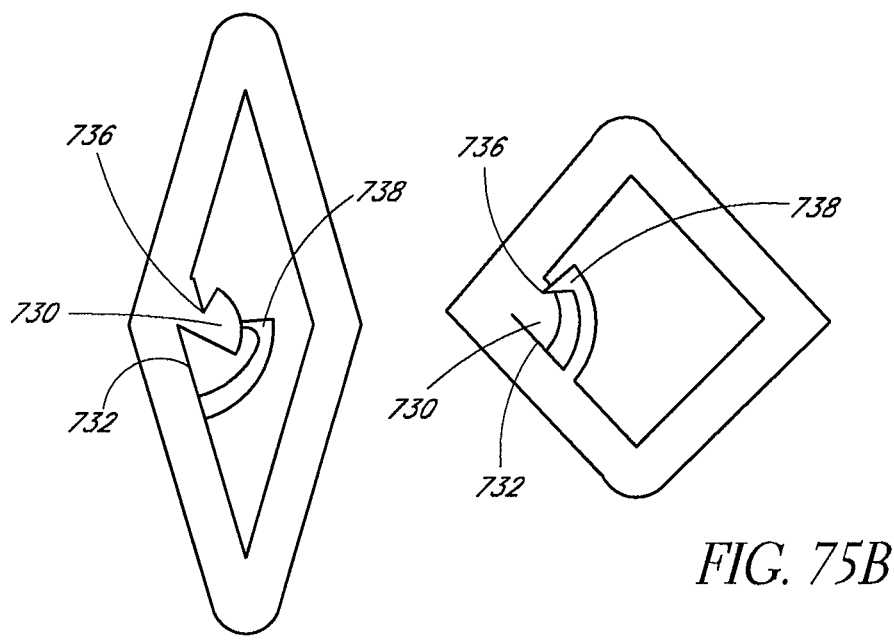
FIGS. 75A and 75B are schematic views of an angular mechanical stop with a latch for resisting recoil.

FIGS. 75A and 75B depict another embodiment of a radial restraint with a recoil resistant feature. Angular stop 730 from FIGS. 74A and 74B is provided with a notch 736 that forms an interference fit with a latch 738 protruding from valve assembly 310 adjacent to surface 732. As valve assembly 310 expands, angular stop 730 will eventually abut against to surface 732 to prevent further expansion. Latch 738 will also move closer to notch 736 as valve assembly 310 expands. When the preset diameter is reached, latch 738 forms an interference fit with notch 736 that resists collapse to a smaller diameter. It is contemplated that a balloon catheter may be used to expand valve assembly 310 to the desired diameter and to engage latch 738 to notch 736.

Figure 59:
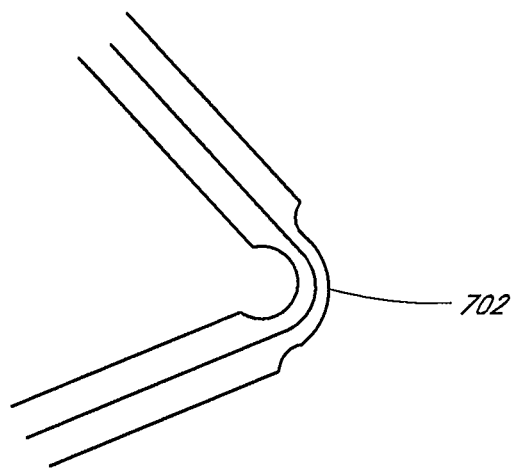
FIG. 59 is a schematic view of a wire bend with a symmetrically reduced diameter.
Figure 60:
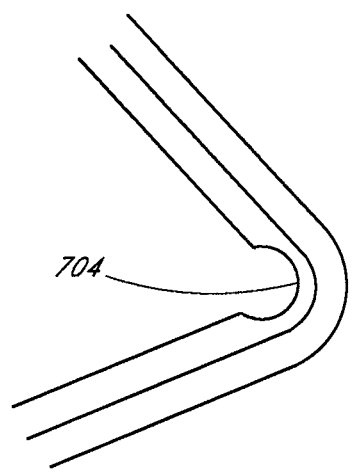
FIG. 60 is a schematic view of an alternative embodiment of a wire bend with an asymmetrically reduced diameter.

Although both shape memory and non-shape memory based prostheses provide diameter-dependent expansion forces that reach zero upon attaining their original shapes, the degree of force exerted can be further modified by altering the thickness of the wire or structure used to configure the support or prosthesis. A prosthesis can be configured with thicker wires to provide a greater expansion force to resist, for example, greater radial inward forces located at the native valve site, but the greater expansion force will still reduce to zero upon the prosthesis attaining its preset diameter. Changes to wire thickness need not occur uniformly throughout a support or prosthesis. Wire thickness can vary between different circumferences of a support or prosthesis, or between straight portions and bends of the wire structure. As illustrated in FIG. 59, the decreased diameter 702 may be generally symmetrical about the longitudinal axis of the wire. Alternatively, as in FIG. 60, the decreased diameter 704 may be asymmetrical, where the diameter reduction is greater along the lesser curvature of the wire bend or undulation relative to the longitudinal axis of the wire. At portions of the prosthesis where the exertion of a particular expansion force against surrounding tissue has importance over the actual diameter attained by that portion of the prosthesis, the various methods for controlling diameter can be adapted to provide the desired expansion force. These portions of the prosthesis may include areas used for anchoring and sealing such as the axial wedging portions or anchors previously described.

Figure 62:
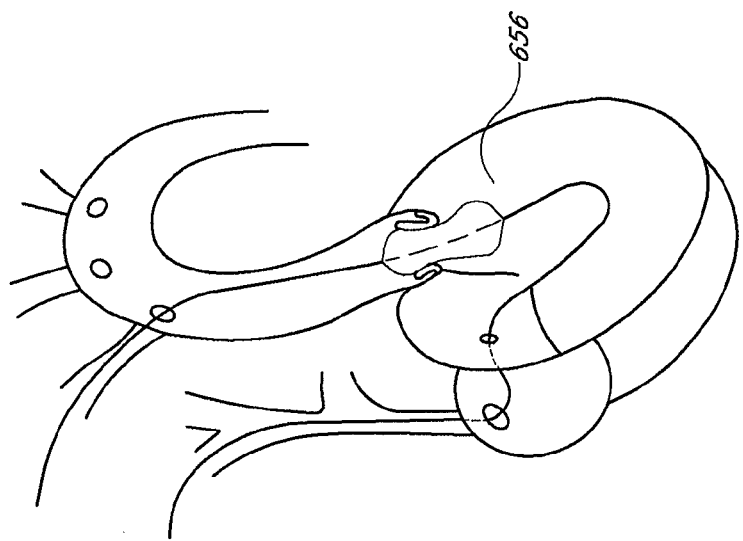
FIG. 62 is a schematic view of a balloon catheter passed over the guidewire of FIG. 61 to dilate the native valve.
Figure 61:
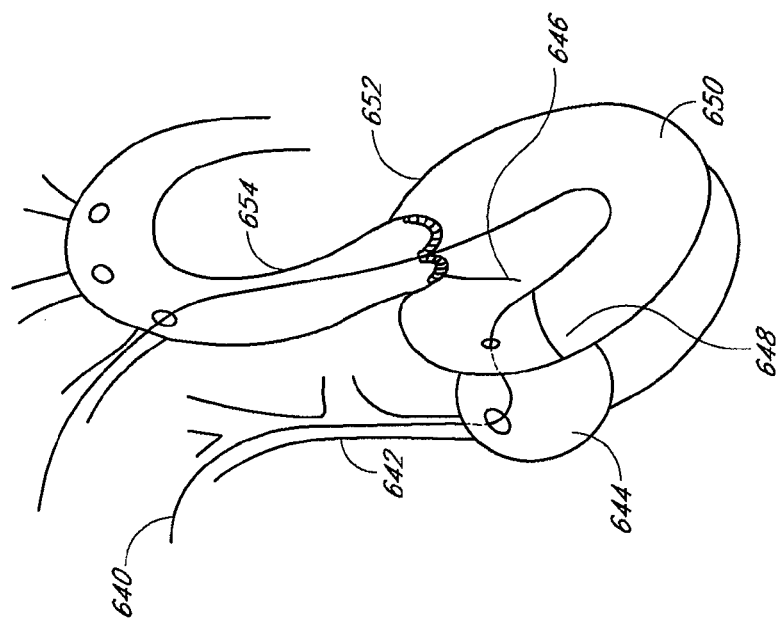
FIG. 61 is a schematic view of one embodiment of the implantation procedure for the prosthetic valve where the distal end of a transseptally placed guidewire has been externalized from the arterial circulation.
Figure 63:
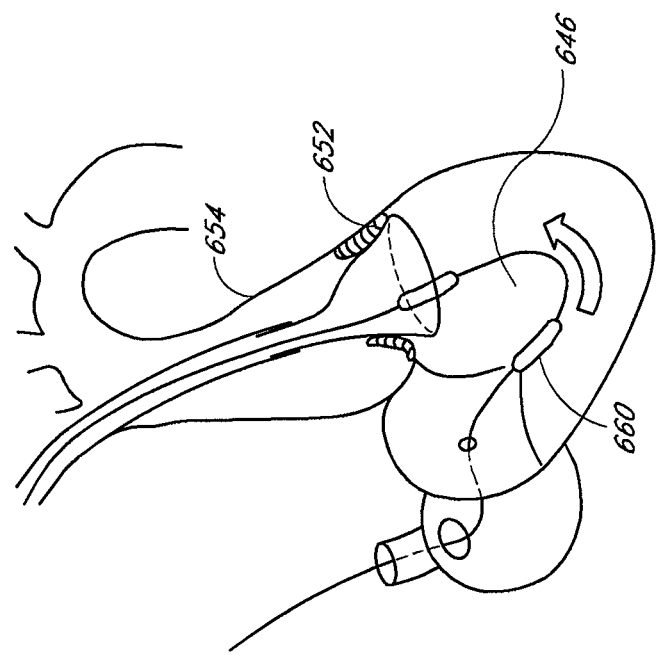
FIG. 63 is a schematic view showing the deployment of a prosthetic valve by an arterial approach over the guidewire of FIG. 62.
Figure 64:
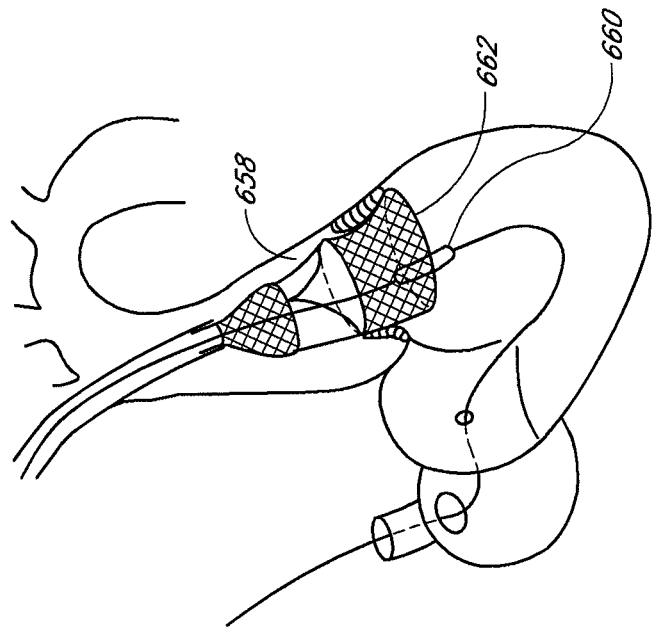
FIG. 64 is a schematic view showing a balloon catheter passed over the guidewire of FIG. 63 from a venous approach and placed opposite the stented native valve for additional ablation and/or securing of the lower portion of the stent.
Figure 65:
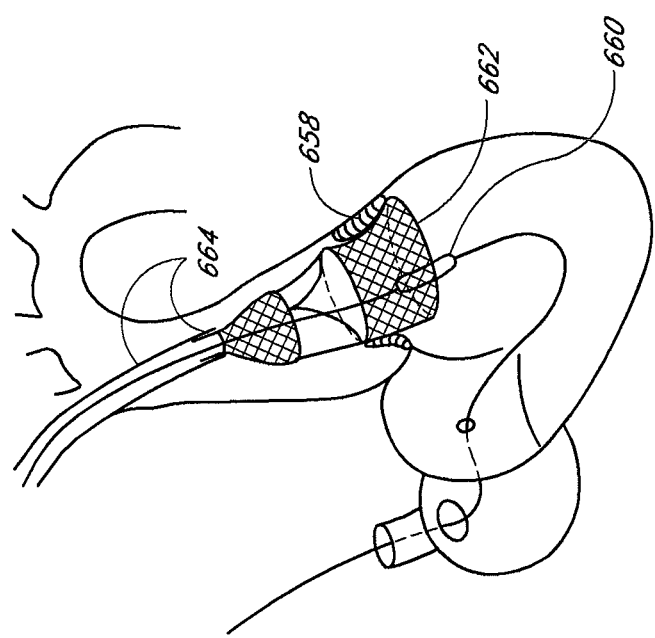
FIG. 65 is a schematic view showing how the stent of FIG. 64 remains attached to the delivery system by braces to allow full positioning of the stent.

Referring to FIG. 61, a method for deploying the preferred embodiment of the invention using the separate stent is provided. The method of deployment comprises a guidewire 640 inserted via a venous approach 642 and passed from the right 644 to left atrium 646 through a known transseptal approach, herein incorporated by reference. After transseptal puncture, guidewire 640 is further directed from left atrium 646 past the mitral valve 648 to the left ventricle 650 and through the aortic valve 652. An introducer (not shown) is inserted via an arterial approach and a snare (not shown), such as the Amplatz GOOSE NECK® snare (Microvena, Minn.), is inserted through the introducer to grasp the distal end of guidewire 640 and externalize guidewire 640 out of the body through the introducer. With both ends of guidewire 640 external to the body, access to the implantation site is available from both the venous 642 and arterial approaches 654. In FIG. 62, aortic valve 652 is pre-dilated by a balloon catheter 656 using a well-known valvuloplasty procedure, herein incorporated by reference. The prosthesis is then implanted as previously described by passing the delivery system from either the venous or arterial approaches. As illustrated in FIG. 63, the prosthesis 658 may be implanted using arterial approach 654 with prosthetic valve 658 implanted above the level of native valve 652. As shown in FIG. 64, a balloon catheter 660 may be passed by venous approach 642 for further displacement of native valve 652 and/or to further secure the lower stent 662 to the annulus. Hooks 664, shown in FIG. 65, connecting the delivery catheter to prosthetic valve 658 allow full control of prosthetic valve 658 positioning until the operator chooses to fully release and implant prosthetic valve 658. A separate stent may then be implanted by venous approach 642 at the valvular ring to further push back the native valve or valve remnants and reduce recoil forces from these structures. Passing balloon 660 by the venous approach 642 avoids interference with superiorly located prosthetic valve 658. Implantation of replacement valve 658 by arterial approach 654 prior to the ablation of the native valve 652 or valve remnants by venous approach 642 may reduce the risks associated with massive aortic regurgitation when native valve 652 is pushed back prior to implantation of replacement valve 658. Reducing the risks of massive aortic regurgitation may provide the operator with additional time to position replacement valve 658.

It is further contemplated that in the preferred embodiment of the invention, valve assembly 310 also comprises a drug-eluting component well known in the art and herein incorporated by reference. The drug-eluting component may be a surface coating or a matrix system bonded to various portions of valve assembly 310, including but not limited to central support band 314, anchors 316 318, valve 312, loop elements 352 or wires 342. The surface coating or matrix system may have a diffusion-type, erosive-type or reservoir-based drug release mechanism. Drugs comprising the drug-eluting component may include antibiotics, cellular anti-proliferative and/or anti-thrombogenic drugs. Drugs, as used herein, include but are not limited to any type of biologically therapeutic molecule. Particular drugs may include but are not limited to actinomycin-D, batimistat, c-myc antisense, dexamethasone, heparin, paclitaxel, taxanes, sirolimus, tacrolimus and everolimus.

Figure 50:
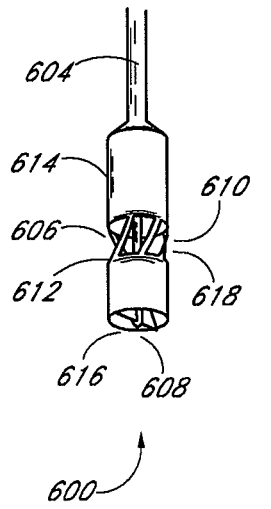
FIG. 50 is side view of an impeller and impeller housing of one embodiment of the blood pump.
Figure 51:
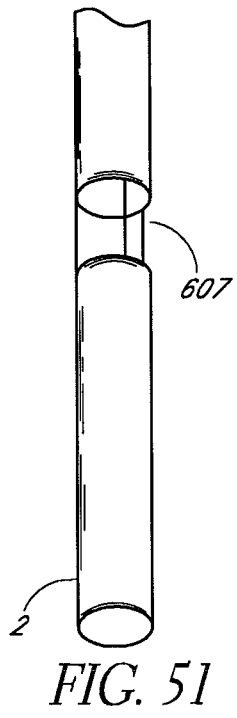
FIG. 51 is a side view of a catheter with catheter cells that allow blood flow by the impeller.
Figure 52:
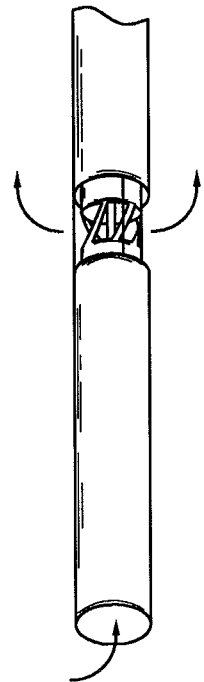
FIG. 52 is a side view of the catheter with the impeller in place and blood flow depicted by arrows.

As previously mentioned, one embodiment of the system for implanting the prosthesis and/or excising the native valve leaflets contemplates maintaining blood flow across the native valve site during the excision and implantation procedure. By maintaining blood flow across the native valve, use of extracorporeal circulation or peripheral aorto-venous heart assistance and their side effects may be reduced or avoided. Major side effects of extracorporeal circulation and peripheral aorto-venous heart assistance include neurological deficits, increased bleeding and massive air emboli. FIGS. 50 through 52 depict one embodiment of the invention for maintaining blood perfusion during the procedure. This embodiment comprises a blood pump 600 and an opening 602 positioned in the wall of tubular catheter 2 of the excision system. When the tubular catheter 2 is positioned at the excision site, blood pump 600 allows continued blood flow across the excision site that would otherwise be interrupted during the excision procedure. Blood pump 600 may comprise a motor, a shaft and an impeller. Blood pump 600 is insertable through passage 15 of tubular catheter 2. The motor is connected to a shaft 604 that in turn is coupled to an impeller 606. The motor is capable of rotating shaft 604, resulting in the rotation of impeller 606. Impeller 606 comprises a proximal end 608, a distal end 610 and a plurality of fins 612 angled along the longitudinal axis of impeller 606, such that when impeller 606 is rotated in one direction, fins 612 are capable of moving blood from a proximal to distal direction. When impeller 606 is rotated in the other direction, fins 612 are capable of moving blood in a distal to proximal direction. The ability to rotate impeller 606 in either direction allows but is not limited to the use of the blood pump in both anterograde and retrograde approaches to a heart valve. The blood pump is positioned generally about catheter opening 602. The blood pump has an external diameter of about 4-mm and the passage of the catheter has a 4-mm internal diameter. Catheter opening 602 has a longitudinal length of about 4-mm. Catheter opening 602 may comprise a plurality of cells located along a circumference of tubular catheter 2. To reduce interruption of blood flow through tubular catheter 2 during the implantation portion of the procedure, catheter opening 602 should preferably be about 30 mm from the tip of catheter 2 or distal to the bell housing 6a. This positioning of catheter opening 602 reduces the risk of occlusion of catheter opening 602 by the replacement valve.

FIG. 50 depicts an optional feature of blood pump 600 further comprising an impeller housing 614 having at least one proximal housing opening 616 and at least one distal housing opening 618. Housing 614 protects passage 15 of tubular catheter 2 from potential damage by rotating impeller 600. Proximal 616 and distal housing cells 618 provide inflow and outflow of blood from the impeller, depending on the rotation direction of impeller 600.

To reduce interruption of blood flow through catheter 2 during the implantation portion of the procedure, catheter opening 602 should preferably be at least a distance of about 30 mm from the distal tip of the catheter or about distal to the bell housing 6a to avoid occlusion of catheter opening 602 by the replacement valve.

Figure 53:
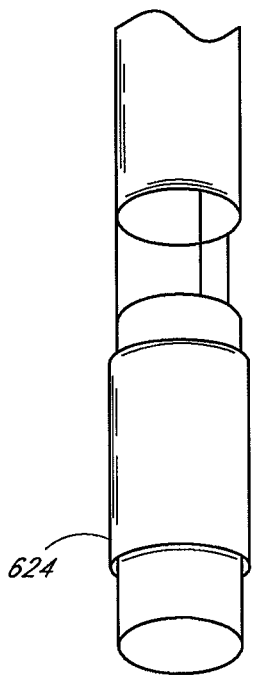
FIG. 53 depicts another embodiment of the invention with a separate blood pump catheter relative to the prosthesis delivery system.
Figure 54:
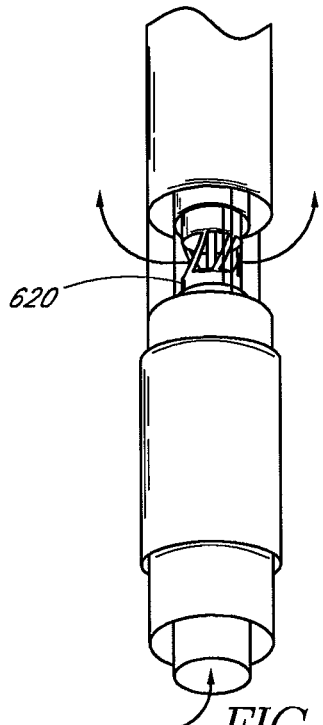
FIG. 54 illustrates the embodiment shown in FIG. 16 with the blood pump in place and blood flow shown by arrows.

FIGS. 53 and 54 depict an alternative embodiment, where blood pump 620 is located in a second catheter 622 in the prosthesis delivery system. Once blood pump 620 and second catheter 622 are in position, the prosthesis delivery system 624 is slid over the separate catheter 622 to position the prosthesis for implantation, while avoiding blockage of blood flow in separate catheter 622. In this embodiment, the diameter of the delivery system is preferably about 8 mm.

Figure 66:
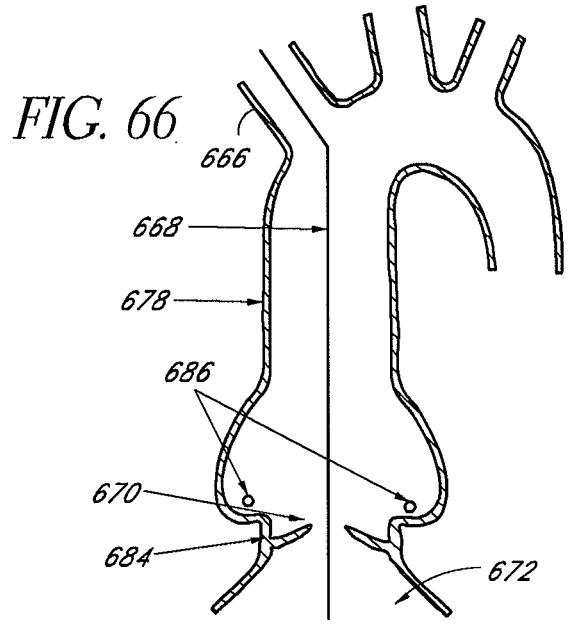
FIG. 66 depicts a schematic view of another embodiment of the implantation procedure for the prosthetic valve where a guidewire is inserted into the axillary artery and passed to the left ventricle.
Figure 67:
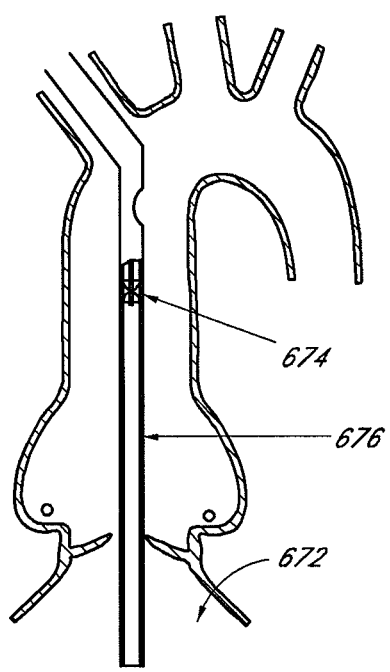
FIG. 67 depicts a schematic view of a blood pump passed over the guidewire of FIG. 66.
Figure 68:
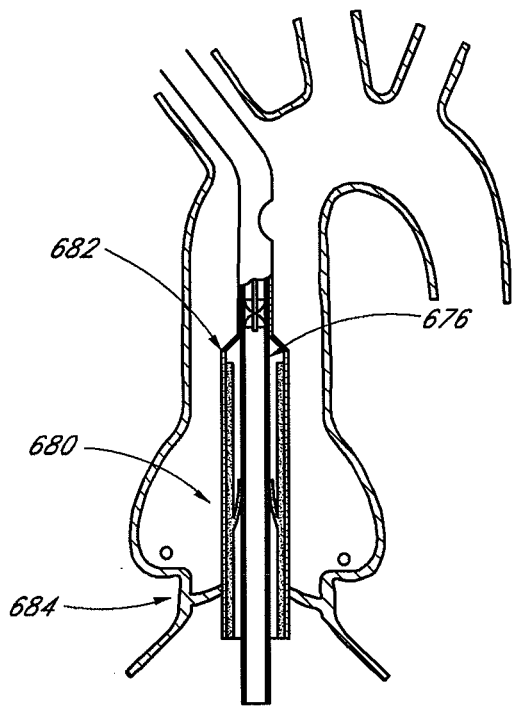
FIG. 68 depicts a schematic view of a valve prosthesis passed over the blood pump of FIG. 67.
Figure 69:
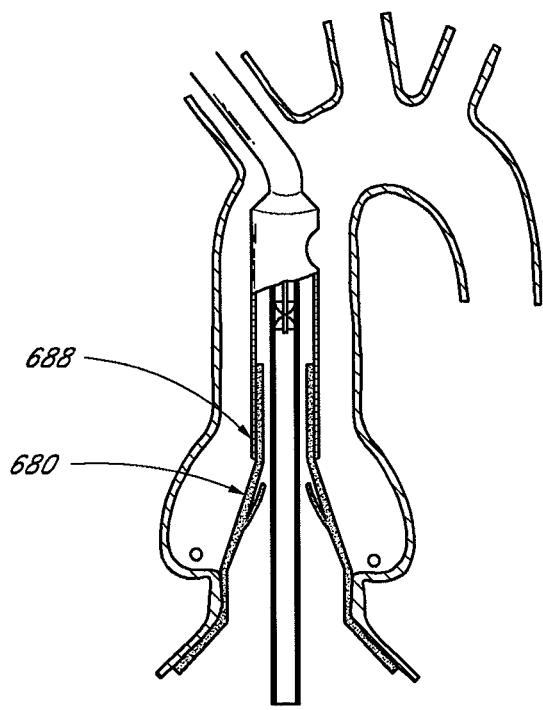
FIGS. 69 and 70 depict schematic views of the deployment and attachment of the prosthesis of FIG. 68 to the vessel wall.
Figure 70:
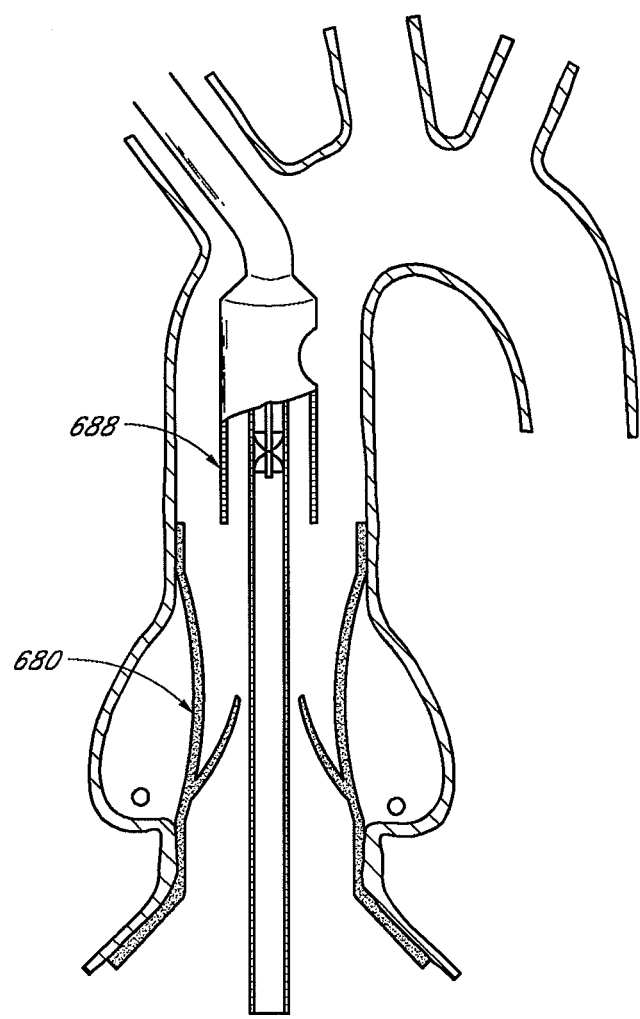

One method of using the blood flow pump during the implantation of the prosthesis is now described. This procedure may be performed under fluoroscopy and/or transesophageal echocardiography. FIG. 66 shows vascular access made through the axillary artery 666. A guidewire 668 is inserted past the aortic valve 670 and into the left ventricle 672. In FIG. 67, a blood pump 674 is inserted into a hollow catheter passed 676 over guidewire 668 inside the aorta 678 and pushed into left ventricle 672. Blood pump 674 is started to ensure a steady and sufficient blood flow of about 2.5 L/min from left ventricle 672 downstream during the valve replacement. FIG. 68 depicts valve prosthesis 680, retained on the delivery system 682 and positioned by sliding over blood pump catheter 676. Prosthesis 680 is positioned generally about the valve annulus 684 and the coronary ostia 686, with the assistance of radiographic markers. As shown in FIGS. 69 and 70, the sheath 688 overlying prosthesis 680 is pulled back and prosthesis 680 is deployed as previously described Catheter hooks 690 connecting the delivery catheter to the prosthetic valve allow full control of prosthetic valve positioning until the operator chooses to fully release and implant the prosthetic valve. Optional anchoring hooks, described previously, may be deployed generally about he annulus, the ventricle and the ascending aorta. Deployment of the anchoring hooks may be enhanced by radial expansion of a balloon catheter that further engages the hooks into the surrounding structures. Blood pump 674 is stopped and blood pump catheter 676 is removed. Other configurations may be adapted for replacing a valve at other site will be familiar to those skilled in the art.

Figure 76:
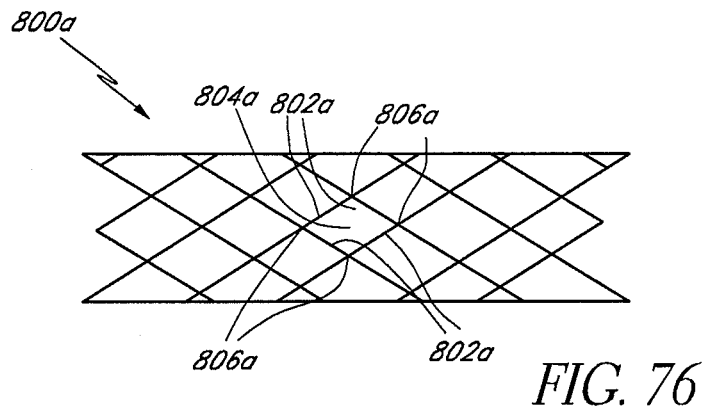
FIG. 76 is a schematic view of a prosthesis frame comprising straight structural members forming diamond-shaped cells.

Referring to FIG. 76, the invention comprises, as with other embodiments described above, a prosthesis frame 800a consisting of a plurality of structural members 802a that form cells 804a. The cells 804a may have one or more shapes and be arranged in generally repeating patterns through at least a portion of the prosthesis frame 800a. In the embodiment shown in FIG. 76, the members 802a are generally straight in configuration and form generally diamond shaped cells 804a. In other contemplated embodiments, such as those shown in FIGS. 77A and 77B, the prosthesis frame 800b comprises a plurality of structural members 802b that have, at least in part, a generally curved or sinusoidal configuration to form cells 804b. Again, the cells 804b may have one or more shapes and be arranged in generally repeating patterns through at least a portion of the prosthesis frame 800b. The curved structural members 802b may distribute the forces associated with contraction and expansion across more of the members, as compared with the configuration shown in FIG. 76, where the forces may be imparted more specifically to the points of connection or junctions 806a of the members 802a. By distributing the stresses through a greater portion of the prosthesis frame 800b, the risk of structural failure may be reduced, permitting an increase in the expansion size ratio between the contracted and expanded configurations of the prosthesis frame. It is contemplated that portions of the prosthesis frames 800a and 800b may be configured so as to be contracted for delivery to about 7 mm in diameter and expandable in an unconstrained format to a diameter of about 55 mm or more. Such expansion ratios are not expected to be achieved using existing valve frame designs.

Figure 77A:
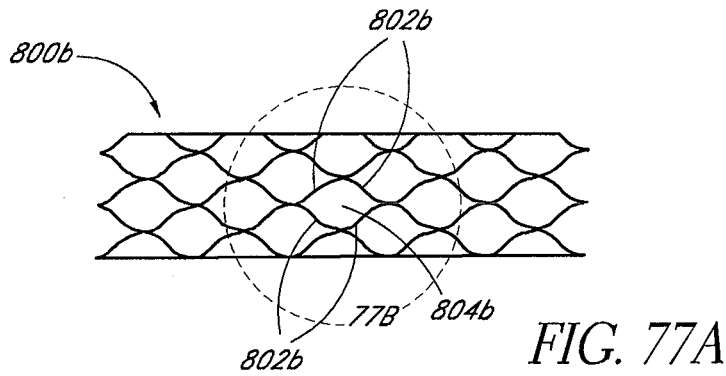
FIG. 77A is a schematic view of a prosthesis frame comprising curved structural members forming elliptoid-shaped cells.
Figure 77B:
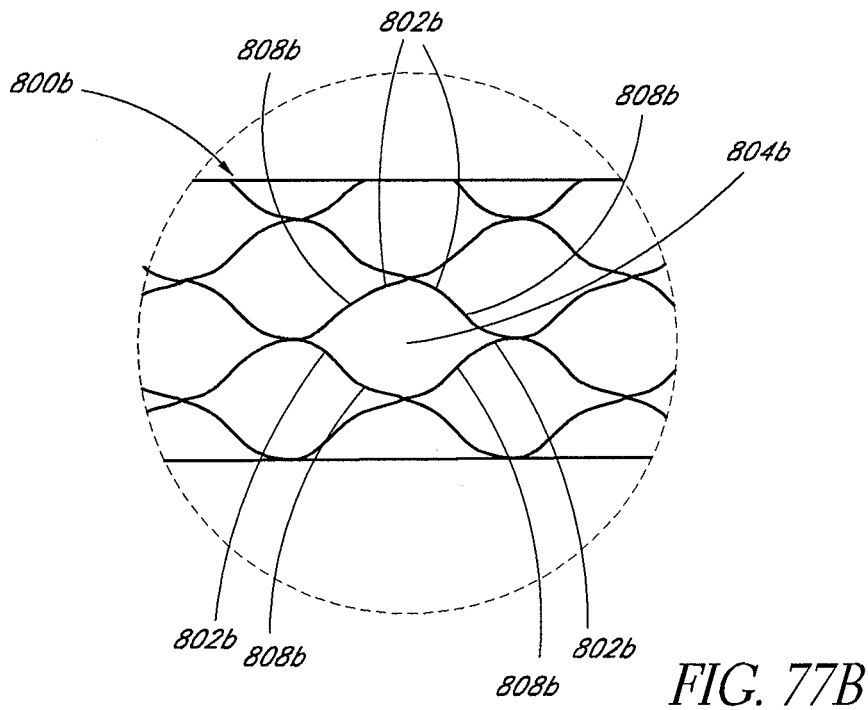
FIG. 77B is a detailed view of a cell in FIG. 77A.
Figure 78:
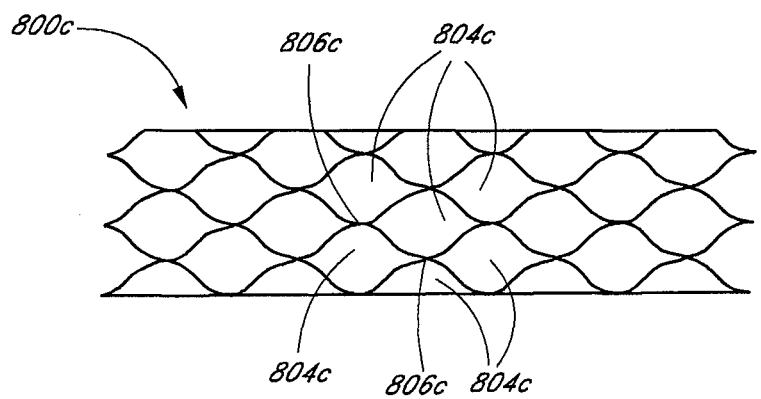
FIG. 78 is a schematic view of an another embodiment of a prosthesis frame comprising curved structural members.
Figure 79:
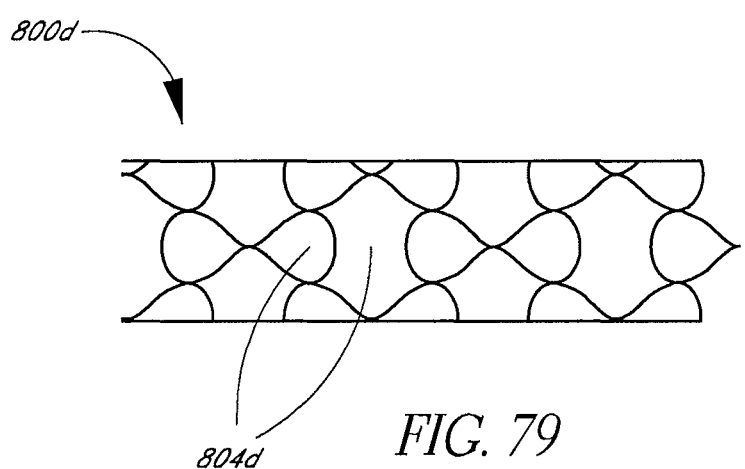
FIG. 79 is a schematic view of an another embodiment of a prosthesis frame comprising curved structural members.

As shown in FIGS. 77A and 77B, at least one embodiment of the prosthesis frame 800b has a repeating cell configuration, each comprising four segments of structural members 802b that have at least one inflection point 808b separating a relative convex curvature from a relative concave curvature. In one such embodiment, some of the cells 804b are axially, radially, and diametrically symmetrical. In other embodiments, some of the individual cells 804b may not be symmetrical in at least one respect, or in all respects. In either case, it is contemplated that the frame 800b may comprise portions having homogenous cell shapes and portions having heterogeneous cell shapes. Examples of such embodiments are shown in FIGS. 78 and 79. In FIG. 78, a prosthesis frame 800c comprises a homogenous pattern of symmetrical cells 804c, although with another optional contemplated feature of at least one junction 806c in each cell 804c being open, as shown. In FIG. 79, a prosthesis frame 800d comprises a heterogeneous pattern of asymmetrical cells 804d. One of ordinary skill in the art should appreciate that the possible variations are quite large, constrained only by effective self-expansion or balloon expansion when deployed in-situ so that the frame corresponds to the native lumen in a manner desired.

Figure 80A:
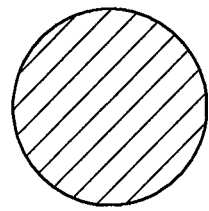
FIGS. 80A through 80E depict cross-sectional views of various embodiments of the structural members.
Figure 80B:
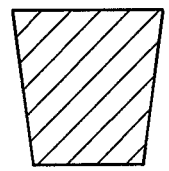
Figure 80C:
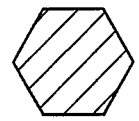
Figure 80D:
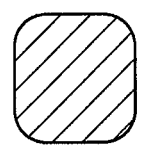
Figure 80E:
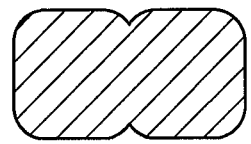

In yet other embodiments, cell asymmetries may be provided with different structural member configurations, where the member size, thickness, and cross-sectional shape or area are varied. Such variations are exemplified in FIGS. 80A through 80E. As shown, the cross-sectional shape of a segment of a structural member may comprise any one or more of a variety of shapes, including but not limited circular (FIG. 80A), oval, trapezoidal (FIG. 80B), polygonal (e.g., FIG. 80C), square (FIG. 80D), and rectangle. As exemplified in FIG. 80D, the corners of the cross sectional shape, if any, may be angled, rounded or smoothed to varying degrees. The corners, tips, and surfaces of the prosthesis frame may be processed using mechanical polishing, electropolishing or another of a variety surface alterations known in the art. At either the junctions of two adjoining structural members converge, the resulting cross-section may be the combined cross-section of both structural members, such as exemplified in FIG. 80E, which shows two members of FIG. 80D together. In the alternative, the width at the junction may be less than or greater than the combined width of the two adjacent structural members.

As referenced above, any one structural member may have a non-uniform cross-section over its length, including within the length of an individual cell, to create non-uniform radial forces within the cell and across a plurality of cells defined by such structural member. Such non-uniformity may also be beneficial in reducing local stresses associated with contraction and expansion.

Figure 81:
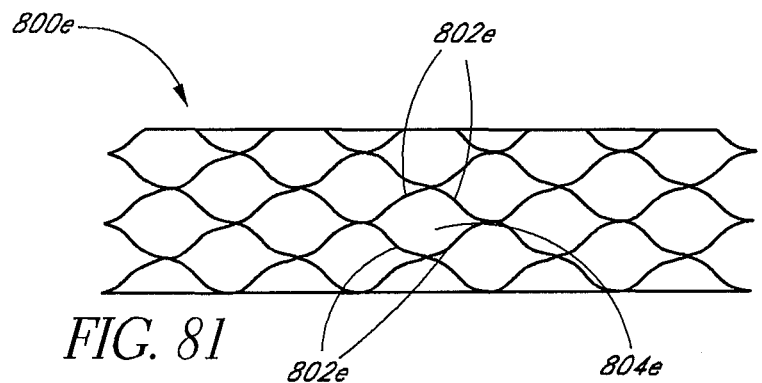
FIG. 81 is a schematic view of another embodiment of a prosthesis frame comprising curved and linear structural members.
Figure 82:
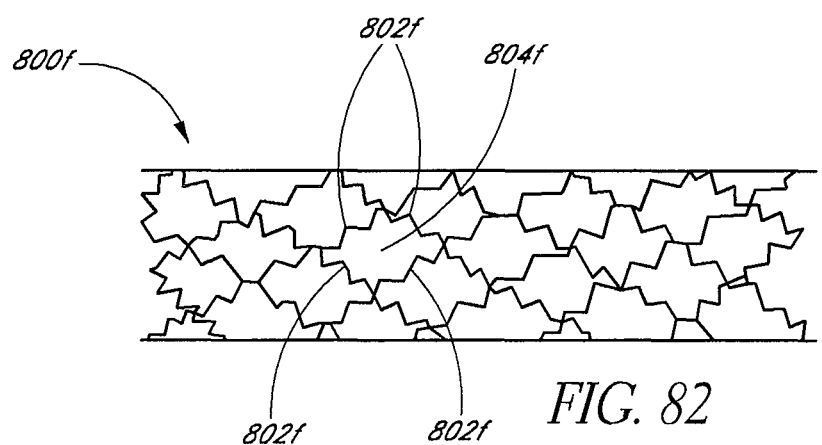
FIG. 82 is a schematic view of another embodiment of a prosthesis frame comprising multi-angular structural members.

With each cell, the location of the junction of members between adjacent cells may be positioned asymmetrically. By way of example, FIG. 81 illustrates a prosthesis frame 800e comprising curvilinear structural members 802e to form asymmetrical cells 804e. In an alternative embodiment, exemplified by FIG. 82, a prosthesis frame 800f comprises structural members 802f formed in a generally zig-zag configuration to form symmetrical or asymmetrical cells 804f. The zig-zag configuration is believed to improve upon otherwise straight members, such as those shown in FIG. 76, by distributing the stress associated with radial expansion and contraction to a plurality of points between junctions. As with the above embodiments, the prosthesis frame may be configured with heterogeneous patterns of cells or homogeneous patterns or both.

Figure 83:
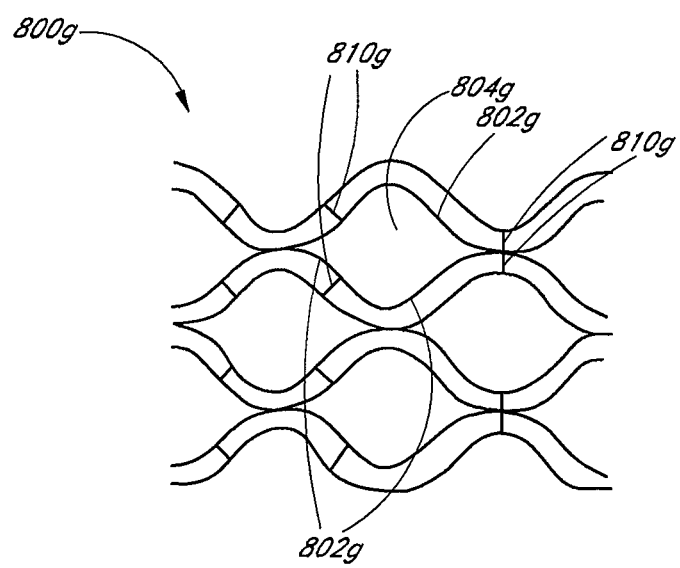
FIG. 83 is a schematic view of an another embodiment of a prosthesis frame comprising curved discrete elliptoid cells joined by connecting rods.

In yet another contemplated embodiment of the present invention, shown by example in FIG. 83, a prosthesis frame 800g may comprise discrete cells 804g that are separated by intercell limbs or connecting rods 810g provided between the plurality of curved structural members 802g to link the individual cells 804g.

With the present invention, individual cells of a prosthesis frame may be characterized by their relative length and width. It is generally preferred that the ratio of the cell length to width be about 0.5 to about 3.0, more preferably about 1.5 to 2.5 and most preferably about 1.75 to about 2.25. Cell configurations having size ratios generally within these ranges are believed to have improved expansion and structural characteristics.

Figure 84:
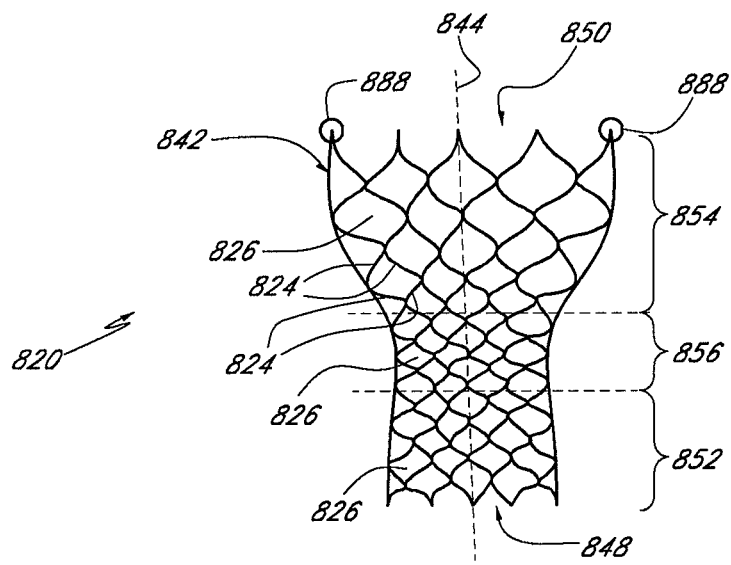
FIG. 84 is a schematic view of one embodiment of a non-cylindrical prosthesis frame comprising elliptoid cells with variable sizes.
Figure 85:
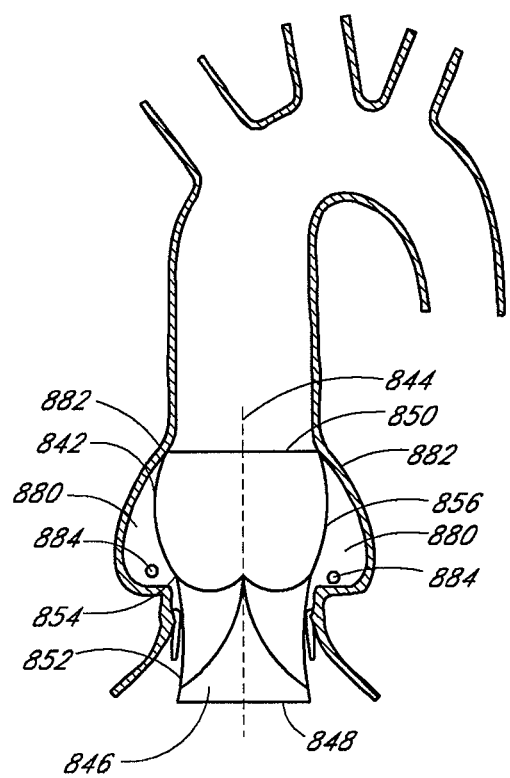
FIG. 85 is a schematic view of the prosthesis frame of FIG. 85 implanted in the aortic position.

Referring to FIG. 84, as well as FIG. 85 showing application to (for example) an aortic valve and surrounding lumen, a particular prosthesis configuration is contemplated, exemplified by the embodiment shown therein, where such configuration has been shown to be very effective at supporting a prosthetic heart valve within a native lumen. With this contemplated configuration, as with other possible variations, a heterogeneous pattern of asymmetrical cells is provided, although portions thereof may comprise homogeneous patterns as well. With continuing reference to FIG. 84, one embodiment of the present invention comprises a heart valve prosthesis 820 comprising a non-cylindrical frame 822 having an intersecting pattern of structural members 824 that join to form cells 826 of varying sizes and shapes.

The non-cylindrical frame 822 of FIG. 84 is shown in a fully expanded state with a longitudinal axis 844 therethrough. The heart valve prosthesis 820 further comprises, preferably and by way of example, a tricuspid tissue valve 846 supported by the frame 822. Improvements to a tricuspid tissue valve contemplated for use with the present invention are described in co-pending application Ser. No. 11/128,826, entitled "HEART VALVE PROSTHESIS AND METHODS OF MANUFACTURE AND USE" and filed May 13, 2005, incorporated herein by reference in its entirety. The non-cylindrical frame 822 comprises an inflow end 848 and an outflow end 850, with three zones therebetween: an inflow zone 852, an outflow zone 854 and a valve support zone 856 positioned between the inflow zone 852 and the outflow zone 854. The frame 822 is configured to be contracted to a much smaller size for, by way of example, insertion within a catheter sheath for deployment at the site of a heart valve.

The non-cylindrical frame 822 preferably comprises portions having homogeneous and heterogeneous patterns of cells. The homogeneous portion or portions may comprise a plurality of cells in which adjacent cells are of the same size, shape and/or wall (structural member) configuration. In one embodiment, exemplified by the one shown in FIG. 84, each row of cells is homogeneous, although two or more adjacent rows could be homogeneous as well and still achieve the function of the particular embodiment shown. It is contemplated, however, that irregularity may be desired, in which case a row of heterogeneous cells may be beneficial. The homogeneous portion may also comprise a first alternating array of cells in which each first alternative cell is of the same shape, size and/or wall configuration, with a second alternating array of cells being different from the first but wherein each second alternative cell is of the same shape, size and/or wall configuration.

The heterogeneous portion or portions of the frame 822, at least in the embodiment exemplified in FIG. 84, may comprise a plurality of cells in which adjacent cells are not of the same size, shape and/or wall configuration. For example, even as between two cells having generally the same size, their relative length-to-width ratios may be different. Likewise, even as between two cells having generally the same shape, their relative sizes may be quite different. In one embodiment, exemplified by the one shown in FIG. 84, adjacent cells 826 along the longitudinal axis 844 (from the inflow end 848 to the outflow end 850) are different in size, shape and/or wall configuration. In this particular embodiment, the cells 826 are largest at the outflow zone 856, smaller at the inflow zone 852, and smallest at the valve support zone 854. Upon expansion, the shape of the various cells differs as well along the longitudinal axis. This variation in arrangement of cell size, shape and/or relative dimension permits dramatic differences in the degree of radial expansion of individual cells within the prosthesis frame. It is believed that relatively larger cell sizes generally allow greater radial expansion at such portions of the prosthesis frame while relatively smaller cell sizes generally limit or control the degree of radial expansion at those portions of the prosthesis frame. It is also believed that variations in the cross-section of individual structural members will also impact the degree of radial expansion and the radial force exerted against any lumen within which it is deployed. The heterogeneous portion may also consist of a plurality of alternating arrays or alternating rows of cells wherein a first set of alternating arrays or rows are homogeneous in shape, size and/or wall configuration but the balance are heterogeneous in shape, size and/or wall configuration.

With some embodiments, as exemplified by the one in FIGS. 84 and 85, the inflow zone 852 may be tapered inwardly from inflow end 848 toward valve support zone 854. This generally conical configuration beneficially resists migration of the prosthesis frame against the forces generated by blood flow from the left ventricle to the aortic arch. The conical configuration is believed to provide increasing radial outward force and/or frictional resistance with surrounding structures when deployed in-situ. The configuration of the inflow end 848 may also be tailored to provide a mechanical abutting surface against the superior surface of the left ventricle 672 to resist displacement of the prosthesis. In the preferred embodiment, the increased radial outward force exerted by the inflow zone 868 may be provided through changes in the configuration of the cells and/or the structural members, or by particular cell arrangements. It would be expected that, based upon this teaching, one of ordinary skill in the art could optimize various parameters to create frames meeting particular needs.

With reference still to FIGS. 84 and 85, in one embodiment of the invention, the valve support zone 854 is configured to support a valve, for example a tricuspid tissue valve 846. As explained above, it is both inventive and important for the portion of the supporting frame to have varied expansion and radial forces along the length of the frame. With this particular example, the valve support zone 854 is configured to ensure a controlled expansion upon deployment. Specifically, the cells 826 of the valve support zone 854 are arranged and/or configured to expand to a defined or preset maximum diameter. As explained above, controlling the expanded diameter of the portion of the frame supporting the valve provides greater control over coaptivity of the valve leaflets. That ensures that the valve 846 supported directly therein operates as effectively as possible in-situ. If the frame 822 at the valve support zone 854 were permitted to expand insufficiently, the leaflets might overlap to an undesirable degree, resulting in less efficient blood flow. A similar result would occur if the valve support zone were permitted to expand too much.

The valve support zone 854 comprises a generally axially-curved or concave configuration, or an overall toroidal configuration, as shown by example in FIG. 84. Such a configuration can further resist deviations from the desired or optimal valve support zone expansion configuration because variations in the mechanical stress exerted from the inflow zone 852 and/or outflow zone 856, caused by anatomical and pathological variations of surrounding structures, will be dispersed along the entire length of the middle zone curved structure, thereby minimizing or preventing any effects on middle zone expansion to its defined or optimal expansion configuration. In comparison, a prosthesis frame with a more cylindrical shape may respond more unpredictably to variations in a patient's anatomy by kinking or bowing, thereby disrupting the geometry of the valve that is resistant to expansion variations of adjacent zones. By providing a consistent expanded configuration for the valve support zone that is resistant to expansion changes of adjacent zones, a consistent valve geometry is achieved and valve function may be improved. Restricting one or more portions of the prosthesis frame to an expansion size that is generally less than the lumen of the surrounding anatomical structures and a range of potential anatomical variations may provide a prosthesis design with a reproducible valve configuration without unduly restricting the cross-sectional area of restriction frame expansion to the degree where the rate of blood flow is impaired.

As explained, the valve leaflets of valve 846 (or opening of any type of valve supported within the frame) are preferably positioned in the valve support zone 854 because the reproducibility and predictability of its cross sectional area and/or shape helps to maintain the desired valve geometry and coaptivity of those leaflets. In alternative embodiments of the invention, other portions of the valve assembly (e.g., commissure), may be located or engaged to the inflow zone 852 and/or outflow zone 856 to provide improved support and stability of the valve assembly along a greater portion of the prosthesis frame 822. A valve assembly spanning two or more zones of the prosthesis may help to disperse mechanical forces acting upon the valve assembly.

It is contemplated that with the present invention, for example as with the embodiment shown in FIG. 85, the valve support zone 854 of the frame 822 can be configured for supra-annular positioning above the aortic valve annulus when deployed; that is, the valve support zone 854, which supports prosthetic valve 846, is preferably positioned above the native valve. That provides at least two benefits: one, it permits a more controlled expansion of the valve support zone 854, unconstrained by the native lumen; and two, it provides more space for the valve opening or valve assembly as it is not constrained by the lumen of the native valve location which is often stenotic. Limited expansion of a prosthesis frame intended to occupy at least the supra-annular region may also be beneficial because it may prevent unnecessary expansion of the prosthesis frame 822 into other body structures. For example, by limiting expansion of the prosthesis frame 822 at the valve support zone 854 and providing a space 880 between the prosthesis frame 822 and the walls of the aortic root or bulb 882, occlusion of the coronary ostia 884 by the prosthesis frame 822 may be avoided. A sufficient space 880 between the frame 822 and the coronary ostia 884 would also permit access to the ostia 884 using coronary catheters to perform coronary catheterization for diagnostic or therapeutic purposes, if necessary, after deployment of the prosthesis frame 822. Coronary catheters can access the space 880 surrounding the prosthesis either through the cells in the cells 826 of the prosthesis frame 822 or other cells that may be provided in the prosthesis frame 822.

Referring still to FIGS. 84 and 85 by example, the valve support zone 854 and the outflow zone 856 of the prosthesis frame 822 may also be further configured with an increasing cross-sectional size along the longitudinal axis 844 in the direction away from the valve support zone 854 toward the outflow end 850. The purpose, among other reasons, for doing so is to resist migration or displacement caused by backflow forces of the column of blood in the ascending aorta. While it is commonly believed that aortic valve prosthesis migration is greater along the direction of forward blood flow, i.e. from the left ventricle to the aorta, there can be equal or greater forces applied by the backflow of blood following systole. The mass of blood flowing through the aortic valve during systole is generally equivalent to the stroke volume of the left ventricle, generally about 25 ml to about 75 ml, or greater if a patient has a dilated left ventricle 672 from aortic insufficiency. However, it is hypothesized that upon completion of the systolic phase of heart contraction, the backflow of blood that causes closure of the aortic valve is generated by the entire column of blood in the ascending aorta and aortic arch, which results in a much greater back flow force than the forward force exerted during systole. Thus, it is hypothesized that anchoring of the prosthesis frame may be optimized or improved using directional or non-directional anchoring or fixation structures that consider backflow forces as well as or more than forward migration forces. It should also be noted that the prosthesis frame embodiments disclosed herein may comprise discrete anchors positioned proximally, distally, or therebetween, to further enhance reduction, if not elimination, of migration in-situ.

It is contemplated that, as exemplified by the embodiments of FIGS. 84 and 85, the present inventive prosthesis may comprise a non-uniform diameter frame, in which no substantial continuous portion of the prosthesis frame has a constant diameter. Moreover, the prosthesis frames described herein may be self-expandable or balloon expandable.

In one embodiment of the invention, the inflow end 848 of the prosthesis frame 822 in the expanded configuration has a diameter of about 15 mm to about 40 mm, preferably about 25 mm to about 30 mm, and most preferably about 26 mm or about 29 mm. In one embodiment, the outflow zone 856 of the prosthesis frame 822 in the expanded configuration has a maximum diameter of about 35 mm to about 65 mm, preferably about 40 mm to about 60 mm, and most preferably about 45 mm or about 55 mm. The restricted diameter of the valve support zone 854 of the prosthesis frame 822 may be about 18 mm to about 30 mm, preferably about 20 mm to about 28 mm, and most preferably about 22 mm or about 24 mm. Actual in situ or in vivo diameters in the expanded configurations may vary depending upon the anatomy and pathology of the individual patient.

It is contemplated that the prosthesis frame of any of these aforementioned embodiments may be manufactured using any of a variety of processes known in the art. Laser cutting of the prosthesis from metal tubular structure is one preferred method, but other methods such as fusing multiple wire elements together, or bending of one or more wire elements into a prosthesis frame may also be used. With laser cutting, the starting tube material may be of uniform diameter or of varied diameter, depending upon the desired fully expanded configuration desired. The slits or cells cut into the tube may be of uniform size or of varied size, again depending upon the desired expanded configuration.

As explained above, it is contemplated that the prosthesis frame 822 would be configured so that when deployed it could be positioned so as to be constrained at the native valve annulus by the anchoring function of the inflow zone 852, the upper portion of the prosthesis frame 822 could still be subject to unintended or undesired lateral movement due to the profile of the native lumen. To minimize such movement, the prosthesis frame 822 is preferably configured so that an enlarged radial cross-section at the outflow zone 856 would engage or be positioned so as to be close to engaging the adjacent wall of the native lumen. It is contemplated that if one makes the present invention as exemplified by the embodiment shown in FIGS. 84 and 85, the outflow zone 856 of the prosthesis frame 822 would abut the aortic lumen along at least one or more portions of its perimeter to maintain the orientation of the prosthesis frame in a desired position.

An additional feature of at least the embodiments exemplified in FIGS. 84 and 85 is that the diameter of the prosthesis frame 822 at the outflow end 850 is smaller than the diameter within the outflow zone 856 adjacent thereto. In one specific embodiment, the outflow zone 856 comprises a generally bulbous structure intended to occupy a substantial portion of space in the aortic bulb 882 or ascending aorta. Having a generally bulbous configuration has a benefit of potentially minimizing trauma to the ascending aorta during deployment. As contemplated in deployment, the outflow end 850 could be the last portion of the prosthesis frame 822 released from a delivery catheter when the prosthesis is deployed through the aorta valve from a peripheral artery. Given the relatively large expansion ratio of the outflow zone 856 and the sudden rate of unconstrained self-expansion, it is contemplated that, in some situations, the outflow end 850 might pose a risk of damage to the lumen of the aorta. This risk may be reduced by tapering radially inwardly the outflow end 850 in the expanded configuration.

The present invention is suitable for placement at the aortic valve annulus, as shown in FIG. 85. In that regard, the inflow zone 852 of the non-cylindrical frame 822 is configured, when implanted, to exert a radially outward force against surrounding structures in the expanded configuration of the frame. The radially outward force may push aside existing valve components, if needed, to enlarge the cross-sectional area available for blood flow through the valve. Although the native valve leaflets are shown in FIG. 85 as having been pushed into the left ventricle, one or more leaflets may be pushed into the aorta. The radially outward force may also provide frictional resistance to prosthesis migration that may be caused by blood flow, cardiac muscle contraction and other factors.

Although the valve prosthesis may be implanted using a basic delivery catheter and retaining sheath, as previously described with reference to FIG. 55 for example, when a self-expanding structure is released from a retaining sheath and expanded, it has a tendency to pull out the remaining portions of the frame from between the catheter and sheath, resulting in a "springing out" or "jumping out" effect of self-expanded structures with premature deployment of the device. Referring to FIG. 84, the outflow zone 856 or outflow end 850 of the prosthesis frame 822 may further comprise one or more, and preferably two or more, engagement structures 888 for retaining a portion of the prosthesis frame 822 on the delivery catheter to allow partial release of the prosthesis frame in a controlled manner. The engagement structures 888 may also be useful for engaging a deployed prosthesis frame for the purposes of removing the device or repositioning the fully deployed device.

In some embodiments of the invention, the delivery catheter and retaining sheath may comprise additional features to enhance the implantation of the prosthetic valve. In one embodiment, the retraction of the retaining sheath is actuated proximally on the catheter using a mechanical control, such as a dial or slide. The mechanical control may provide one or more detents or other type of stop mechanism at a point in sheath retraction where further retraction may result in a significant action such as the initial release of the prosthesis frame and/or release of the engagement structures, if any. The detents or stop may provide tactile feedback to the operator (i.e. temporary resistance to further movement) or require altered user intervention (i.e. shift direction or activate a button or latch) to further retract the sheath.

In some embodiments of the invention, the delivery catheter and retaining sheath may comprise mechanical controls having different mechanical advantages for retracting the sheath. In one embodiment, a dial control may be provided on the proximal catheter to slowly withdraw the sheath, thereby allowing fine control of prosthesis release during the initial positioning of the device. Once the device is deployed to the extent where release of the remaining prosthesis would not substantially affect the desired valve location, a slide control may be used to quickly retract the rest of the sheath and to fully release the prosthesis.

As previously described, although the structural members of the prosthesis frame may be configured to provide greater expansion ratios compared to existing stent-type frames, due to the presence of the valve assembly in the prosthesis frame and the limited extent that the prosthetic valve profile in the delivery configuration may be reduced without damage to the valve assembly, the diameter of the delivery catheter loaded with the prosthetic valve may be larger compared to delivery catheters loaded with coronary stents. In some instances, the diameter of the delivery catheter may be sufficiently large to preclude the use of off-the-shelf introducer sheaths or to require a larger-than-desired opening into a blood vessel in order to use a sheath. It is recognized that only the distal portion of such a delivery catheter containing the prosthetic valve may have a larger diameter and that the sections or segments of the delivery catheter and retaining sheath proximal to the prosthetic valve may have a smaller diameter. However, once the enlarged diameter portion of the delivery catheter is initially inserted into an access site, an introducer sheath can no longer be inserted over the delivery catheter. To overcome this limitation, in some embodiments of the invention, an integrated introducer sheath may be provided with the delivery catheter that is capable of sliding along the delivery catheter body proximal to the portion containing the prosthetic valve. Once the prosthetic valve portion of the delivery catheter is inserted, the integrated introducer is then passed into access site along with the reduced diameter portion of the delivery catheter. Once the integrated introducer is fully inserted, the remaining portions of the delivery catheter can slide through the access site using the introducer. The integrated introducer may also have a peel-away feature that is known to those in the art such that it may be removed from the delivery catheter while the distal end of the delivery catheter remains in the body.

Figure 86:
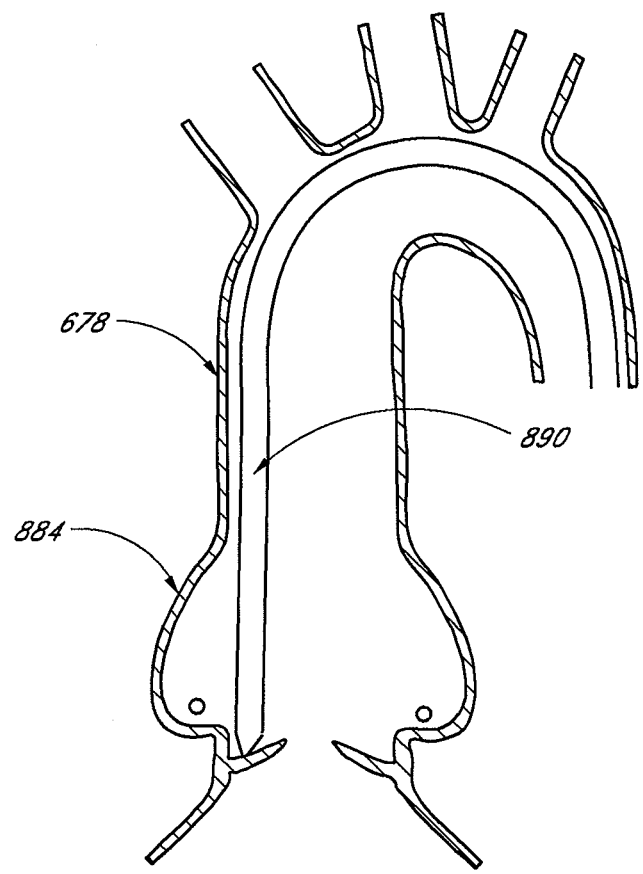
FIG. 86 depicts one embodiment of the invention comprising a delivery catheter inserted from an arterial access site and passed through the aortic arch.

Because the distance from the insertion or access site on the body may be a substantial distance from the implantation site of the prosthetic valve, one or more longitudinal stiffening elements may be provided along the length of the delivery catheter and/or retaining sheath to provide sufficient "pushability" or column strength to adequately manipulate the distal end of the delivery catheter across the substantial distance. Such stiffening, however, may restrict the flexibility of the catheter. For example, when a prosthetic valve is inserted via a femoral artery and through the descending aorta to the aortic arch, the stiffness of the delivery catheter is likely to cause the delivery catheter to follow the path that generates the least amount of mechanical strain on the catheter body. With reference to FIG. 86, that results in a delivery catheter 890 that sits eccentrically in the lumen to one lateral side of the ascending aorta 678 or aortic bulb 884. Such a catheter may be difficult to manipulate and direct more centrally in the aortic lumen or through a stenotic aortic valve having a small central lumen. To provide a delivery catheter 890 with adequate column strength yet having sufficient flexibility to be manipulated with respect to the cross sectional lumen position, the longitudinal stiffening elements may be arranged about 180 degrees apart on the delivery catheter body or retaining sheath. This provides a plane of bending to the delivery catheter that lies between the two spaced apart stiffening elements.

Figure 87A:
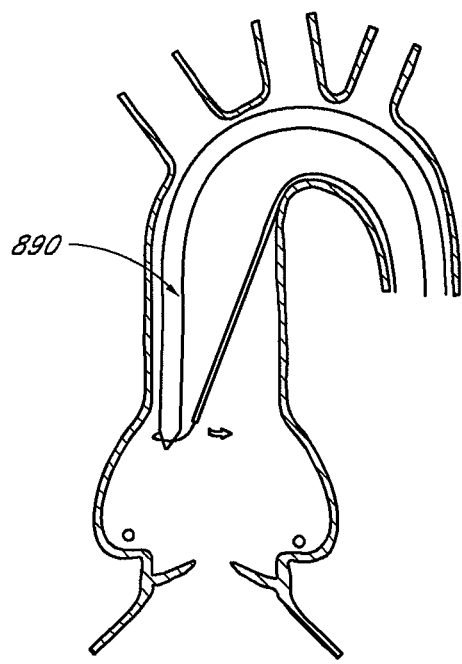
FIG. 87A depicts the use of a snare used to grasp the distal end of delivery catheter.
Figure 87B:
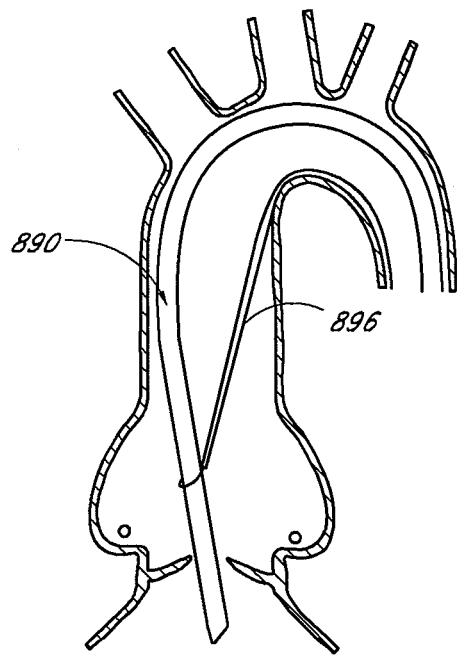
FIG. 87B illustrates the reorientation of the distal end of the delivery catheter toward the aortic valve lumen using the snare.

To manipulate the delivery catheter 890 in the lumen of the cardiovascular system, any of a variety of mechanisms or devices may be used. For example, the delivery catheter and/or retaining sheath may comprise a known steering wire that may be actuated by the user at the proximal catheter end to cause bending of the distal catheter tip. In another embodiment of the invention, as exemplified in FIGS. 87A and 87B, a separate snare 892 may be used to either snare the distal end of the delivery catheter 890 and/or catheter guidewire, which can be pulled to angle or direct the catheter 890 to the desired location or pathway. The snare 892 may be provided in a kit comprising the delivery catheter system and prosthetic valve.

Figure 88A:
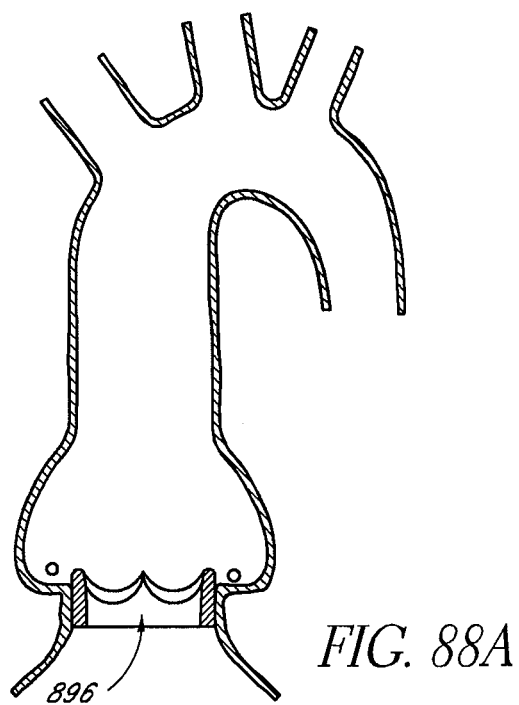
FIG. 88A is a schematic view of a previously surgically implanted aortic valve in a patient.
Figure 88B:
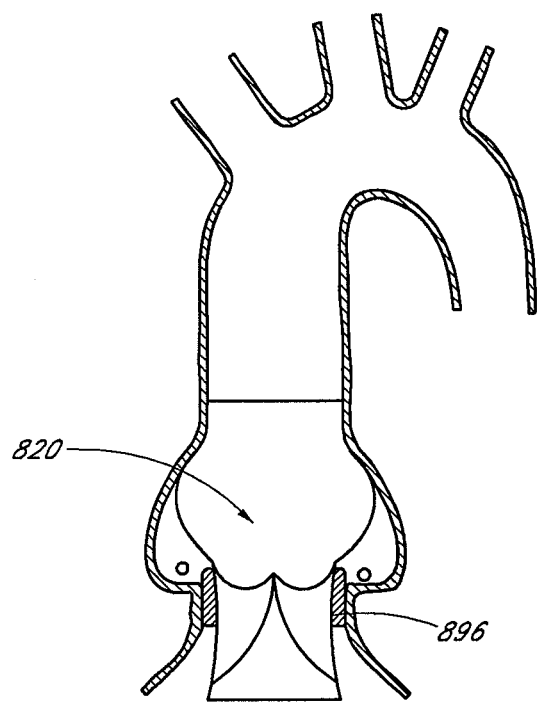
FIG. 88B depicts the implantation of a self-expanding replacement aortic valve into the previously surgically implanted aortic valve.

In one embodiment, depicted by example in FIGS. 88A and 88B, the self-expandable prosthetic valve 894 is implanted about an existing prosthetic valve 896 or prosthetic conduit. The existing prosthetic valve may be a surgically implanted valve 896, as illustrated in FIG. 88A, or a minimally invasively inserted valve. A self-expanding prosthetic valve 896 may be better suited for implantation in patients with existing prosthetic valves 896, as illustrated in FIG. 88B, because a self-expanding prosthetic valve 894 is adapted to exert sufficient radial force against the existing prosthetic valve in order to seal, anchor and/or provide an adequate lumen diameter at the site of the existing prosthetic valve. In comparison, a balloon-expandable prosthetic valve would likely require a degree of overexpansion such that the final configuration of the prosthetic valve, after recoil following deflation of the balloon, is capable of exerting sufficient force and/or having a final predetermined diameter. However, a pre-existing prosthetic valve will prevent or limit the necessary overexpansion needed to implant a balloon expandable prosthesis at the site of an existing prosthesis because the existing prosthesis lacks the compliance of even sclerotic tissue.

As illustrated in FIG. 92, the retrograde delivery (with respect to the direction of blood flow) of the prosthetic valve 820 may be performed peripherally accessing the arterial vasculature and passing the a delivery system catheter 920 retrograde through the aorta to reach the aortic valve. The delivery system catheter 920 typically has a restraining sheath 922 that first releases the inflow end 848 of the prosthetic valve 820. By first releasing the inflow end 848, the prosthetic valve 820 can be anchored to the valve annulus 916 before the remaining portions of the prosthetic valve 820 are released. This initial anchoring effect at the valve annulus 916 reduces the potential displacement or shifting that can occur as the prosthetic valve 820 is released.

Referring to FIG. 93, the prosthetic valve 820 may also be implanted using an antegrade delivery procedure, e.g. by the transseptal route described previously. For antegrade delivery, the prosthetic valve 820 is typically mounted into a delivery catheter 920 in the opposite orientation from retrograde delivery, i.e. the outflow end 850 of the prosthetic valve 820 would be mounted towards the distal tip 924 of the delivery catheter 920 relative to the inflow end 848 of the prosthetic valve 820. Likewise, any structures on the delivery catheter 920 and/or prosthetic valve 820 for retaining the prosthetic valve 820 on the delivery catheter 920 to resist "spring-out" of the self-expanding prosthetic valve 820 is preferably adapted to retain the inflow end 848 of the prosthetic valve 820 when used with a delivery catheter 920 having a traditional pull-back restraining sheath. Although the prosthetic valve 820 may be delivered with a traditional delivery catheter 920 with a pull-back sheath 922, such a catheter 920 loses the advantage of first releasing the inflow end 848 of the prosthetic valve 820 against the valve annulus 916 and instead, the outflow end 850 of the prosthetic valve 820 is first released in the aortic bulb 882. The implantation of the outflow end 850 lacks the initial anchoring characteristic found in the retrogade delivery procedures described above.

Referring to FIGS. 95 and 96, in one embodiment, the disadvantages of the antegrade delivery procedure may be addressed by using a delivery catheter 926 with a restraining sheath 928 that can be pushed forward (FIG. 95) rather than a sheath 922 that is pulled back (FIG. 96). Referring to FIG. 94, a sheath 928 that pushed forward allows the release of the proximal portion of the prosthetic valve 820 first, the inflow end 848 of the prosthetic valve 820 may be released first to anchor to the prosthetic valve 820 at the valve annulus 916 before releasing the rest of the valve 820. An additional advantage of delivering the prosthetic valve 820 using a proximal release catheter 926 is that it allows the use of the same prosthetic valve 820 used in retrograde delivery, because the retaining structures, if any, on the prosthetic valve 820 will still be provided on the outflow end 850 of the prosthetic valve 820.

Referring to FIG. 95, the proximal release catheter 926 comprises a restraining sheath 928 surrounding a retaining space 930 that can hold the compressed prosthetic valve (not shown). The restraining sheath 928 is coupled or integral with a movable inner core 932. The inner core 932 may be displaced distally relative to the outer core 934 of the catheter 926 by user manipulation at the proximal end of the catheter 926. The restraining sheath 928 and/or movable inner core 932 are typically coupled to a tapered distal tip 936 of the catheter 926. The inner core 932 is an elongate member configured to move or slide within a lumen 938 of an outer core 934 of the catheter 926. As the inner core 932 is moved distally, it pushes the distal tip 936 and the restraining sheath 928 distally to expose the proximal portion of the prosthetic valve (not shown). This differs from a traditional delivery catheter 920 shown in FIG. 96, where the restraining sheath 922 is pulled back proximally to first release the most distal portion of the valve.

Referring back to FIG. 95, the outer core 934 of the catheter 926 has a distal end 942 and a proximal end 944, and is configured to fit within the retaining space 930 of the catheter 926 along with the compressed stent. The distal end 942 of the outer core 934 is configured to resist distal displacement of the outflow end of the prosthetic valve and maintain the relative longitudinal position of the prosthetic valve when the restraining sheath 928 is pushed distally. The distal end 942 of the outer core 934 may have a flange or an increased diameter that can abut against the outflow end of the prosthetic valve. In some embodiments, the distal end 942 of the outer core 934 may also comprise a retaining structure 948 for resisting the proximal displacement of the prosthetic valve from spring-out forces that are generated when the proximal end of the prosthetic valve is allowed to expand from the retaining sheath 928. As with the catheter described for retrograde valve delivery, the retaining structures may comprise protrusions or indentations that intercalate with the cell structure of the valve support frame, or interface with complementary retaining structures on the valve support frame.

The proximal end 944 of the outer core 934 is tapered distally and joined to the distal end of the remaining portions of the catheter. The tapered configuration facilitates removal of the distally displaced restraining sheath 928 by reducing trauma to the valve leaflets as the retaining sheath 928 is withdrawn through the lumen of the expanded prosthetic valve. After the prosthetic valve has been implanted, the restraining sheath 928 and catheter tip 936 are located distal to the implanted valve. If the restraining sheath 928 were withdrawn as-is through the lumen of the implanted valve, the proximal end 954 of the restraining sheath 928 could easily catch against the valve leaflets and damage them. This is because the leaflets are configured for antegrade passage of blood through the valve lumen, not for retrograde passage that would facilitate withdrawal of the restraining sheath. To reduce leaflet damage, the outer core 934 of the catheter 926 is pushed distally through implanted valve, facilitated by the tapered proximal end 944 of the outer core 934, until the peripheral portion of the proximal end 944 of the outer core 934 comes in contact with the proximal end 954 of the restraining sheath 928. Once this occurs, the proximal end 944 of the outer core 934 will protect the proximal end 954 of the restraining sheath 928 from snagging against the valve leaflets and the catheter body 926 will maintain the valve leaflets in the open position. The delivery catheter 926 can then be withdrawn through the expanded implant and removed from the patient.

The inner core 932 and the distal tip 936 typically will have a longitudinal lumen 940 along their lengths so the that catheter 926 may be passed over a guidewire to facilitate positioning and implantation of the prosthetic valve. In other embodiments of the invention, the catheter may be configured as a rapid exchange catheter with only a short through lumen through the distal tip of the catheter. In variant embodiment, there may not be a guidewire lumen in the catheter, but the distal tip of the catheter may have a guidewire extending distally. The distal guidewire facilitates insertion of the catheter into a valve orifice by providing a smaller guiding structure to initially insert into the orifice. In some embodiments, the distal guidewire may be steerable independent of the catheter, but in other embodiments, the distal guidewire is steerable by steering the catheter itself.

In addition to antegrade delivery of the prosthetic valve by a transseptal route, the prosthetic valve may also be implanted using a surgical or thoracoscopic route whereby access is provided directly through the myocardium of the heart, e.g. transapical access. This transapical approach may be beneficial compared to traditional open heart surgery because it is a) less invasive than open chest access, b) may be used with a beating heart procedure and c) may be used to treat calcified aortic stenosis that a cardiothoracic surgeon may be reluctant to open. A transmyocardial approach may also provide ease of access to multiple cardiac valves and/or cardiac that may be difficult to reach transluminally. Compared to an endovascular retrograde approach, the transmyocardial approach may a) allow implantation of the prosthetic valves in those with small or tortuous aortic or peripheral vascular access, b) reduce the risk of dislodging emboli when passing a catheter through calcified vasculature, and c) allow access through a calcified and stenotic valve that may be easier with the antegrade approach compared to the retrograde approach because of directional resistance from native valve leaflets.

In one embodiment, the patients is prepped and draped in the usual sterile fashion and with fluoroscopy and/or laparoscopic equipment available to assist with the placement of the device. In other embodiments, imaging from intravenous ultrasound may be used to facilitate implantation. Embolic protection devices may also be inserted prior to valve implantation to provide protection against calcifications that may embolize during the procedure. General anesthesia is achieved and the surgeon begins by making an incision between the patient's ribs to create an access site to the heart. An incision is them made in the pericardium and the myocardium to allow insertion of a guidewire to the implantation site. In some patients, only the right lung is ventilated and the left lung is deflated to improve visibility of the heart during the procedure. In one preferred embodiment, a transapical approach can be used with a proximal release catheter to deliver a replacement valve to the aortic valve site. In other embodiments, the transapical approach may be used to access the mitrial valve, the aorta, or an incision in the right base of the heart is created to provide access the tricuspid and pulmonic valves. Preferably, a pursestring suture is placed about the incision site so hemostasis may be achieved quickly after the procedure. Multiple incisions may be used to provide multiple access sites. A snare may be inserted into the patient from an approach opposite the guidewire to facilitate guidewire insertion. Imaging studies are used during implantation to verify guidewire position. A catheter holding the collapsed prosthetic valve is then passed over the guidewire to the implantation site. Radioopaque or other visualization makers may be provided on the catheter to facilitate valve positioning. Once the delivery catheter position is verified, the inner core of the delivery catheter is pushed forward to advance the restraining sheath and to release the proximal end of the valve against the native valve leaflets or annulus. Once anchored at the annulus, the inner core of the delivery cathete may be pushed forward more until the remaining portions of the valve are released into the aortic bulb. Valve position and proper valve function are checked prior to initiating delivery catheter withdrawal.

The tapered proximal end of the outer core of the delivery catheter is then advanced forward through the valve leaflets while generally maintaining the position of the inner core until the tapered proximal end of the outer core contacts the proximal end of the restraining sheath. Once contacted the outer and inner cores of the delivery catheter can be withdrawn together to protect the proximal end of the restraining sheath from snagging or damaging the prosthetic valve leaflets. As the delivery catheter is withdrawn from the heart, the pursestring suture is tighted to reduce blood leakage into the thoracic cavity. After the delivery catheter is removed from the body, a chest tube may inserted into the thoracic cavity to maintain inflation of the lungs until any air leaks, if any, have healed. Valve function is verified by echocardiogram or by catheter-based pressure readings before the closing the thoracotomy incision(s).

Figure 89:
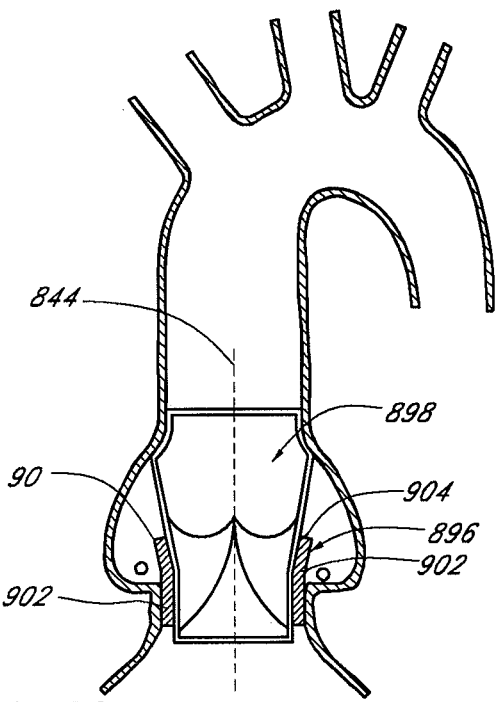
FIG. 89 is a schematic view of a patient with a previously surgically implanted aortic valve with deflected commissure posts and a replacement valve implanted within.
Figure 90:
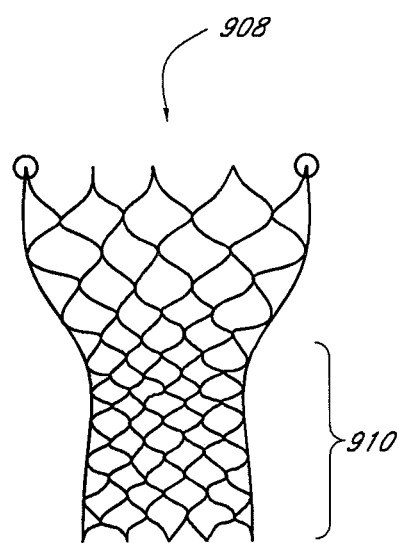
FIG. 90 is a schematic view of an expandable prosthetic valve with a tapered inflow section.

In a further embodiment of the invention, depicted in FIG. 89, an expandable prosthetic valve 898 may be configured for implantation in an existing prosthetic valve 896 or prosthetic conduit such that in addition to pushing aside the valve leaflets of the existing prosthetic valve 896, one or more of the commissure posts 902 of the existing prosthetic valve 896 are deformed or deflected away in order to increase the cross-sectional area of the bloodflow through the expandable prosthetic valve 898. In some embodiments, a balloon catheter or other expansion structure is first applied to one or more of the commissure posts 902 prior to implantation of the expandable prosthetic valve 898 in order to plastically deform the commissure posts 902 and/or to increase the compliance of the commissure posts 902 for expansion by the expandable prosthetic valve 898. In some embodiments, the expandable prosthetic valve 898 is configured to expand with sufficient force to deflect or deform one or more commissure posts 902 without prior application of a balloon catheter. The expandable prosthetic valve 898 may or may not require rotational or angular alignment with the existing prosthetic valve 896 to enhance outward deflection of the commissure posts 902. Angular alignment may be performed by radiography, angiography, intravascular ultrasound or other visualization methods.

Typically the commissure posts 902 are outwardly deflected in a generally radial direction. Not all of the commissure posts 902 need to be deflected or deflected to the same degree or direction. In some embodiments, the ends 904 of one or more commissures posts 902 may be deflected by about 1 mm or more, by about 1.5 mm or more, or preferably by about 2 mm or more. The deflection of the commissure posts may also be measure the degree of deflection. In some embodiments, the commissure posts 902 may be deflected by about 3 degrees or more, about 5 degrees or more, about 7 degrees or more, about 10 degrees or more, or about 20 degrees or more. In embodiments where the commissure posts 902 of the existing prosthetic valve 896 are oriented in a radially inward direction at rest with respect to the longitudinal axis 844 of the expandable prosthetic valve 898, one or more commissures posts 902 may be deflected to a generally parallel direction or a radially outward direction with respect to the longitudinal axis 844.

Although the shape of the expandable prosthetic valve used in patients where the commissure posts are been deformed or deflected may be similar in shape to the non-cylindrical prosthetic valves described above, in some embodiments the expandable prosthetic valves 908 may have a tapered section 910 configured to wedge against the valve leaflets and/or commissure posts 902 of the existing prosthetic valve 896 and deflect them outwardly.

Figure 91:
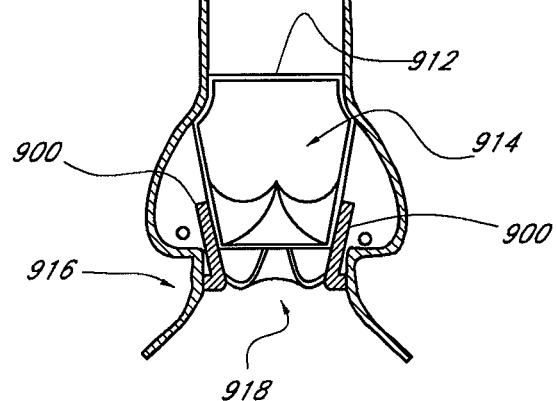
FIG. 91 is a schematic view of a patient with a self-expanding replacement aortic valve anchored about the leaflets of the existing valve leaflets.

As illustrated in FIG. 91, the valve frame 912 of expandable prosthetic valve 914 may or may not be configured or dimensioned to anchor or contact the annulus region 916 of the existing native valve 918 when implanted, as the contact against the valve leaflets 900 may be sufficient to anchor the expandable prosthetic valve 914 in place and/or to seal the expandable prosthetic valve 914 against leakage. Likewise, some embodiments of the invention not configured for implantation in an existing prosthetic valve 896 may be similarly configured to anchor/seal at the valve leaflets of the native valve rather that at the annular region of the existing prosthetic valve. It is popularly believed that anchoring against the annulus of the native valve or prosthetic valve is necessary for anchoring of a non-surgically attached prosthetic valve due to the rigidity of the annulus or annular region, but angiographic studies performed with embodiments of the invention suggest that anchoring and or sealing of the expandable prosthetic valve 908 may primarily occur at the valve leaflets. If anchoring at the valve annulus is unnecessary or secondary, a shorter valve frame may be used with minimally invasive or percutaneously inserted prosthetic valves, which may improve the manueverability of the prosthetic valve 908 when loaded on a delivery catheter, thereby facilitating implantation of such devices and reducing the time required to perform the implantation procedure.

The present invention may be embodied in other specific forms without departing from its spirit or essential characteristics. The described embodiments are to be considered in all respects only as illustrative, and not restrictive and the scope of the invention is, therefore, indicated by the appended claims rather than by the foregoing description. For all of the embodiments described above, the steps of the methods need not be performed sequentially. All changes that come within the meaning and range of equivalency of the claims are to be embraced within their scope.

What is claimed is:

1. A replacement cardiac valve system, comprising:
a delivery catheter comprising:
  a catheter body having an exterior surface;
  a distal flange located at a distal end of the catheter body and extending radially outward from the exterior surface of the catheter body;
  a retaining structure located proximally from the distal flange and extending radially outward from the exterior surface of the catheter body,
  wherein a receptacle is formed between the distal flange and the retaining structure; and
  a restraining sheath movably coupled to the distal end of the catheter body; and
an expandable heart valve having an inflow end and an outflow end, collapsible into the restraining sheath and coupled to the retaining structure of the delivery catheter at the outflow end of the expandable heart valve,
wherein the restraining sheath is configured to move between a proximal closed position that restrains the expandable heart valve and a distal exposed position that first exposes the inflow end of the expandable heart valve,
wherein the retaining structure is configured to restrict proximal longitudinal displacement of the expandable heart valve as the restraining sheath moves between the proximal closed position and the distal exposed position, and
wherein the distal flange is configured to restrict distal longitudinal displacement of the expandable heart valve.

2. The replacement cardiac valve system according to claim 1, wherein the delivery catheter further comprises a taper segment proximal to the restraining sheath.

3. The replacement cardiac valve system according to claim 1, wherein the restraining sheath is configured to move to a release position that exposes the retaining structure.

4. The replacement cardiac valve system according to claim 1, wherein the delivery catheter further comprises a taper segment distal to the restraining sheath.

5. The replacement cardiac valve system according to claim 1, wherein the retaining structure includes at least one protrusion component that is complementary to a receptacle component on the expandable heart valve.

6. A kit comprising:
a self expandable heart valve prosthesis having an inflow end and an outflow end; and
a catheter for delivering the heart valve prosthesis, the catheter comprising:
  an elongate body;
  a distal portion having an exterior surface, a section around which the heart valve prosthesis can be mounted, and a distal flange located at a distal end of the elongate body and extending radially outward from the exterior surface configured to restrict distal longitudinal displacement of the self expandable heart valve prosthesis; and
  a sheath having a proximal end, and being movable over a prosthesis mounting section in a distal direction from a position substantially covering the prosthesis mounting section to a position substantially uncovering the prosthesis mounting section, such that, in use, movement of the proximal end of the sheath first exposes the inflow end of the heart valve prosthesis placed in the prosthesis mounting section; and
  a retaining structure located proximally from the distal flange and extending radially outward from the exterior surface of the distal portion, configured to restrict proximal longitudinal displacement of the heart valve prosthesis as the sheath moves between the position substantially covering the prosthesis mounting section and the position substantially uncovering the prosthesis mounting section, wherein a receptacle is formed between the distal flange and the retaining structure, and wherein the outflow end of the heart valve prosthesis is coupled to the retaining structure.

7. The kit according to claim 6, wherein the distal portion of the catheter comprises a zone of reduced cross-section to form the prosthesis mounting section.

8. The kit according to claim 7, wherein the prosthesis mounting section comprises a proximal end, and wherein the catheter further comprises a projection adjacent the proximal end of the mounting section configured to cooperate with the proximal end of the sheath to minimize interference between the proximal end of the sheath and a deployed prosthesis when, in use, the catheter is withdrawn through the deployed prosthesis.

9. The kit according to claim 8, wherein the projection comprises an area of greater cross-section than that of the mounting section, a cross section of the projection extending around the catheter approximating a cross-section of the proximal end of the sheath.

10. The kit according to claim 9, wherein the projection comprises a sloping surface extending from adjacent the prosthesis mounting section towards an outer surface of the catheter.

11. The kit according to claim 6, wherein the catheter further comprises a distal tip, the tip being formed integrally with the sheath.

12. The kit according to claim 6, wherein the catheter further comprises a guidewire lumen extending along the longitudinal axis of the catheter.

13. The kit according to claim 6, further comprising a guidewire.

14. The kit according to claim 6, wherein the retaining structure includes at least one protrusion component that is complementary to a receptacle component on the heart valve prosthesis.

* * * * *